US008168658B2

(12) United States Patent
Grimm et al.

(10) Patent No.: US 8,168,658 B2
(45) Date of Patent: May 1, 2012

(54) INHIBITORS OF HISTONE DEACETYLASE

(75) Inventors: Jonathan B. Grimm, Newton, MA (US); Jed L. Hubbs, Cambridge, MA (US); Thomas Miller, Brookline, MA (US); Karin M. Otte, Newton Centre, MA (US); Phieng Siliphaivanh, Newton, MA (US); Matthew G. Stanton, Medfield, MA (US); Kevin Wilson, West Newton, MA (US); David Witter, Norfolk, MA (US); Hua Zhou, Waltham, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 697 days.

(21) Appl. No.: 12/224,466

(22) PCT Filed: Feb. 23, 2007

(86) PCT No.: PCT/US2007/004724
§ 371 (c)(1),
(2), (4) Date: Aug. 27, 2008

(87) PCT Pub. No.: WO2007/100657
PCT Pub. Date: Sep. 7, 2007

(65) Prior Publication Data
US 2009/0069250 A1    Mar. 12, 2009

Related U.S. Application Data

(60) Provisional application No. 60/777,714, filed on Feb. 28, 2006.

(51) Int. Cl.
A61K 31/4412     (2006.01)
C07D 409/12      (2006.01)

(52) U.S. Cl. ..................................... 514/336; 546/280.4
(58) Field of Classification Search .................. 514/336; 546/280.4
See application file for complete search history.

(56) References Cited

U.S. PATENT DOCUMENTS

| | | | |
|---|---|---|---|
| 4,670,438 A | 6/1987 | Austel et al. | |
| 4,766,130 A | 8/1988 | Austel et al. | |
| 4,923,869 A | 5/1990 | Prucher et al. | |
| 5,026,705 A | 6/1991 | Prucher et al. | |
| 5,369,108 A | 11/1994 | Breslow et al. | |
| 5,700,811 A | 12/1997 | Breslow et al. | |
| 5,932,616 A | 8/1999 | Breslow et al. | |
| 6,069,143 A | 5/2000 | Ali et al. | |
| 6,087,367 A | 7/2000 | Breslow et al. | |
| 6,174,905 B1 | 1/2001 | Suzuki et al. | |
| 6,407,131 B1 | 6/2002 | Quada, Jr. et al. | |
| 6,506,783 B1 | 1/2003 | Camden et al. | |
| 6,511,990 B1 | 1/2003 | Breslow et al. | |
| 6,541,661 B1 | 4/2003 | Delorme et al. | |
| 6,653,309 B1 | 11/2003 | Saunders et al. | |
| 6,710,065 B1 | 3/2004 | Camden et al. | |
| 6,864,275 B1 | 3/2005 | Camden et al. | |
| 6,984,654 B2 | 1/2006 | Camden et al. | |
| 7,169,801 B2 | 1/2007 | Bressi et al. | |
| 2003/0139404 A1 | 7/2003 | Haag et al. | |
| 2003/0207883 A1 | 11/2003 | Renhowe et al. | |
| 2004/0110832 A1 | 6/2004 | Mjalli et al. | |
| 2004/0142953 A1 | 7/2004 | Delorme et al. | |
| 2004/0186148 A1 | 9/2004 | Shankar et al. | |
| 2004/0192744 A1 | 9/2004 | Haag et al. | |
| 2005/0288282 A1 | 12/2005 | Delorme et al. | |
| 2006/0084667 A1 | 4/2006 | Auvin et al. | |
| 2009/0062297 A1 | 3/2009 | Heidebrecht et al. | |
| 2009/0082308 A1 | 3/2009 | Hubbs et al. | |
| 2009/0105264 A1 | 4/2009 | Hamblett et al. | |
| 2009/0221669 A1 | 9/2009 | Hamblett et al. | |
| 2010/0324092 A1 | 12/2010 | Heidebrecht et al. | |

FOREIGN PATENT DOCUMENTS

| | | |
|---|---|---|
| EP | 1378510 A1 | 1/2004 |
| EP | 1541574 A1 | 6/2005 |
| EP | 1547585 A1 | 6/2005 |
| JP | 11302173 | 11/1999 |
| JP | 2001131130 | 11/1999 |
| JP | 11335375 | 12/1999 |
| WO | 9800144 A1 | 1/1998 |
| WO | 9850031 A1 | 11/1998 |
| WO | 9955663 A1 | 11/1999 |
| WO | 0071510 A2 | 11/2000 |
| WO | 01/30780 A2 | 5/2001 |
| WO | 01/38322 A1 | 5/2001 |
| WO | 0151456 A2 | 7/2001 |

(Continued)

OTHER PUBLICATIONS

Chen, et al., Chemistry—A European Journal, 10(19), pp. 4790-4797 (2004).

(Continued)

*Primary Examiner* — Taofiq A Solola
(74) *Attorney, Agent, or Firm* — Li Su; David A. Muthard

(57) ABSTRACT

The present invention relates to a novel class of compounds. These compounds can inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the compounds of the instant invention and safe dosing regimens of these pharmaceutical compositions, which are easy to follow, and which result in a therapeutically effective amount of these compounds in vivo.

7 Claims, No Drawings

FOREIGN PATENT DOCUMENTS

| | | | |
|---|---|---|---|
| WO | 0164642 | A2 | 9/2001 |
| WO | 0200647 | A1 | 1/2002 |
| WO | 0209648 | A2 | 2/2002 |
| WO | 02/100819 | A1 | 12/2002 |
| WO | 03004472 | A1 | 1/2003 |
| WO | 03/013484 | A2 | 2/2003 |
| WO | 03/024448 | A2 | 3/2003 |
| WO | 03/075929 | A1 | 9/2003 |
| WO | 03/076395 | A1 | 9/2003 |
| WO | 03/076422 | A1 | 9/2003 |
| WO | 03/087057 | A1 | 10/2003 |
| WO | 03/092686 | A1 | 11/2003 |
| WO | 2004/035525 | A1 | 4/2004 |
| WO | 2004/058234 | A2 | 7/2004 |
| WO | 2004/069823 | A1 | 8/2004 |
| WO | 2005/009971 | A1 | 2/2005 |
| WO | 2005/030704 | A1 | 4/2005 |
| WO | 2005/030705 | A1 | 4/2005 |
| WO | 2005053609 | A2 | 6/2005 |
| WO | 2005/092899 | A1 | 10/2005 |
| WO | 2005121073 | A1 | 12/2005 |
| WO | 2006/001958 | A2 | 1/2006 |
| WO | 2006/027346 | A2 | 3/2006 |
| WO | 2006115845 | A1 | 11/2006 |
| WO | 2007087129 | A2 | 8/2007 |
| WO | 2007118137 | A1 | 10/2007 |
| WO | 2008010985 | A2 | 1/2008 |

OTHER PUBLICATIONS

Jaboin, et al., Cancer Research, 62(21), pp. 6108-6115 (2002).

Niwas, et al., Indian Journal of Chemistry, Section B: Organic Chemistry Including Medicinal Chemistry, 24B(7), pp. 754-760 (1985).

Wilson, KJ et al., Bioorganic & Medicinal Chemistry Letters, vol. 18 (2008), pp. 1859-1863, "Phenylglycine and phenylalanine derivatives as potent and selective HDAC1 inhibitors (SHI-1)".

INHIBITORS OF HISTONE DEACETYLASE

PRIORITY CLAIM

This application is a §371 application of PCT/US07/004724 that was filed on Feb. 23, 2007, which claims priority from the U.S. Provisional Application No. 60/777,714, filed on Feb. 28, 2006, now expired.

FIELD OF THE INVENTION

The present invention relates to a novel class of compounds. These compounds can inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases.

BACKGROUND OF THE INVENTION

The inhibition of HDACs can repress gene expression, including expression of genes related to tumor suppression. Inhibition of histone deacetylase can lead to the histone deacetylase-mediated transcriptional repression of tumor suppressor genes. For example, inhibition of histone deacetylase can provide a method for treating cancer, hematological disorders, such as hematopoiesis, and genetic related metabolic disorders. More specifically, transcriptional regulation is a major event in cell differentiation, proliferation, and apoptosis. There are several lines of evidence that histone acetylation and deacetylation are mechanisms by which transcriptional regulation in a cell is achieved (Grunstein, M., *Nature*, 389: 349-52 (1997)). These effects are thought to occur through changes in the structure of chromatin by altering the affinity of histone proteins for coiled DNA in the nucleosome. There are five types of histones that have been identified. Histones H2A, H2B, H3 and H4 are found in the nucleosome, and H1 is a linker located between nucleosomes. Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone. This affinity causes DNA to be tightly bound to the histone and renders the DNA inaccessible to transcriptional regulatory elements and machinery.

The regulation of acetylated states occurs through the balance of activity between two enzyme complexes, histone acetyl transferase (HAT) and histone deacetylase (HDAC).

The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

It has been shown in several instances that the disruption of HAT or HDAC activity is implicated in the development of a malignant phenotype. For instance, in acute promyelocytic leukemia, the oncoprotein produced by the fusion of PML and RAR alpha appears to suppress specific gene transcription through the recruitment of HDACs (Lin, R. J. et al., *Nature* 391:811-14 (1998)). In this manner, the neoplastic cell is unable to complete differentiation and leads to excess proliferation of the leukemic cell line.

U.S. Pat. Nos. 5,369,108, 5,932,616, 5,700,811, 6,087,367 and 6,511,990 disclose hydroxamic acid derivatives useful for selectively inducing terminal differentiation, cell growth arrest or apoptosis of neoplastic cells. In addition to their biological activity as antitumor agents, these hydroxamic acid derivatives have recently been identified as useful for treating or preventing a wide variety of thioredoxin (TRX)-mediated diseases and conditions, such as inflammatory diseases, allergic diseases, autoimmune diseases, diseases associated with oxidative stress or diseases characterized by cellular hyperproliferation (U.S. application Ser. No. 10/369,094, filed Feb. 15, 2003). Further, these hydroxamic acid derivatives have been identified as useful for treating diseases of the central nervous system (CNS) such as neurodegenerative diseases and for treating brain cancer (See, U.S. application Ser. No. 10/273,401, filed Oct. 16, 2002).

In view of the wide variety of applications for compounds containing hydroxamic acid moieties, the development of new inhibitors having improved properties, for example, increased potency or increased bioavailability is highly desirable.

SUMMARY OF THE INVENTION

The present invention relates to a novel class of compounds. These compounds, which can be used to treat cancer, inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the compounds of the instant invention, and safe, dosing regimens of these pharmaceutical compositions, which are easy to follow, and which result in a therapeutically effective amount of these compounds in vivo.

The present invention relates to compounds represented by Formula I and pharmaceutically acceptable salts, solvates and hydrates thereof, as detailed herein.

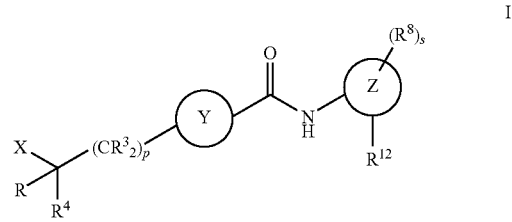

The foregoing and other objects, features and advantages of the invention will be apparent from the following more particular description of embodiments of the invention.

DETAILED DESCRIPTION OF THE INVENTION

The present invention relates to a novel class of compounds. The compounds of the instant invention can inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating cancer in a subject. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases.

The present invention relates to compounds represented by Formula I.

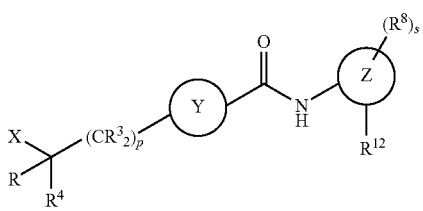

I wherein
X is 1) —$(CR^2{}_2)_nC(O)OR^1$,
2) —$(CR^2{}_2)_nC(O)NR^1{}_2$,
3) —$(CR^2{}_2)_nC(O)R^1$,
4) —$(CR^2{}_2)_nOC(O)NR^1{}_2$,
5) —$(CR^2{}_2)_n$aryl, wherein aryl is optionally substituted with one or more substituents,
6) —$(CR^2{}_2)_nC(O)NR^1(CR^2{}_2)_mNR^1{}_2$,
7) —$(CR^2{}_2)_nC(O)NR^1(CR^2{}_2)_mNR^1C(O)R^1$,
8) —$(CR^2{}_2)_nC(O)NR^1(CR^2{}_2)_nOR^1$, or
9) —$(CR^2{}_2)_nC(O)NR^1(CR^2{}_2)_nC(O)NR^1{}_2$;
Y is unsubstituted or substituted aryl or unsubstituted or substituted heteroaryl;
Z is aryl or heteroaryl;
R is H or unsubstituted or substituted $C_1$-$C_6$ alkyl;
$R^1$ is independently selected from H, $C_1$-$C_6$ alkyl, —$(CR^2{}_2)_n$aryl, and —$(CR^2{}_2)_n$heterocyclyl;
wherein said alkyl, aryl or heterocyclyl is optionally substituted with one or more substituents;
$R^2$ and $R^3$ are independently selected from H, unsubstituted or substituted $C_1$-$C_6$ alkyl, and $(CR^2{}_2)_n$aryl;
$R^4$ is
1) —$(CR^2{}_2)_nNR^5{}_2$,
2) —$(CR^2{}_2)_nNR^5C(O)R^5$,
3) —$(CR^2{}_2)_nNR^5C(O)OR^5$,
4) —$(CR^2{}_2)_n$heterocyclyl,
5) —$(CR^2{}_2)_nNR^5S(O)_2R^5$, or
6) —$(CR^2{}_2)_nNR^5C(O)NR^5{}_2$;
wherein heterocyclyl is optionally substituted with one or more substituents;
optionally, when R is unsubstituted or substituted $C_1$-$C_6$ alkyl and $R^4$ is not —$(CR^2{}_2)_n$heterocyclyl, R and $R^4$ may be cyclized to form a ring system;
$R^5$ is independently selected from H, $C_1$-$C_6$ alkyl, —$(CR^2{}_2)_n$aryl, and —$(CR^2{}_2)_n$heterocyclyl, wherein alkyl, aryl or heterocyclyl may be optionally substituted with one or more substituents;
$R^8$ is unsubstituted or substituted aryl or unsubstituted or substituted heteroaryl;
$R^{12}$ is $NH_2$, $NR^5C(O)R^5$, $NR^5C(O)OR^5$, OH, or NH-Boc;
m is 1, 2 or 3;
n is independently 0, 1, 2, 3 or 4;
p is 0, 1, 2, 3, or 4;

s is 0, 1 or 2;
or a stereoisomer or a pharmaceutically acceptable salt thereof.

In another embodiment, the present invention relates to compounds represented by Formula I wherein:
Y is phenyl, thienyl, or pyridinyl, wherein phenyl, thienyl or pyridinyl is optionally substituted with one or two substituents selected from $R^7$;
Z is phenyl, pyrazolyl, thienyl or pyridinyl;
$R^2$ and $R^3$ are independently selected from H and unsubstituted or substituted $C_1$-$C_6$ alkyl;
$R^7$ is independently selected from unsubstituted or substituted $C_1$-$C_6$ alkyl, $OR^5$, —$(CR^2{}_2)_n$aryl, CN, $CF_3$ and halo;
and all other substituents and variables are as defined above in Formula I,
or a stereoisomer or a pharmaceutically acceptable salt thereof.

A further embodiment of the invention is a compound of Formula II,

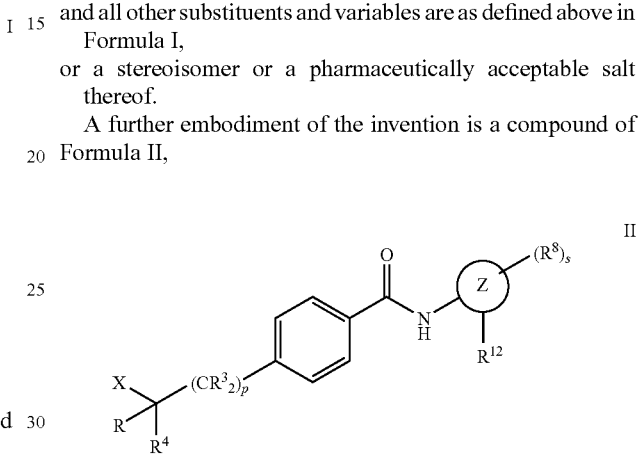

II wherein
X is 1) —$(CR^2{}_2)_nC(O)OR^1$,
2) —$(CR^2{}_2)_nC(O)NR^1{}_2$,
3) —$(CR^2{}_2)_nC(O)R^1$,
4) —$(CR^2{}_2)_nOC(O)NR^1{}_2$,
5) —$(CR^2{}_2)_n$aryl, wherein aryl is optionally substituted with one to three substituent selected from $R^7$,
6) —$(CR^2{}_2)_nC(O)NR^1(CR^2{}_2)_mNR^1{}_2$,
7) —$(CR^2{}_2)_nC(O)NR^1(CR^2{}_2)_mNR^1C(O)R^1$,
8) —$(CR^2{}_2)_nC(O)NR^1(CR^2{}_2)_nOR^1$, or
9) —$(CR^2{}_2)_nC(O)NR^1(CR^2{}_2)_nC(O)NR^1{}_2$;
Z is phenyl or pyrazolyl;
R is H or unsubstituted or substituted $C_1$-$C_6$ alkyl;
$R^1$ is independently selected from H, $C_1$-$C_6$ alkyl, —$(CR^2{}_2)_n$aryl, and —$(CR^2{}_2)_n$heterocyclyl;
wherein said alkyl, aryl or heterocyclyl is optionally substituted with one to three substituent selected from $R^7$;
$R^2$ and $R^3$ are independently selected from H, unsubstituted or substituted $C_1$-$C_6$ alkyl, and $(CR^2{}_2)_n$aryl;
$R^4$ is
1) —$(CR^2{}_2)_nNR^5{}_2$,
2) —$(CR^2{}_2)_nNR^5C(O)R^5$,
3) —$(CR^2{}_2)_nNR^5C(O)OR^5$,
4) —$(CR^2{}_2)_n$heterocyclyl,
5) —$(CR^2{}_2)_nNR^5S(O)_2R^5$, or
6) —$(CR^2{}_2)_nNR^5C(O)NR^5{}_2$;
wherein heterocyclyl is optionally substituted with one to three substituent selected from $R^7$;
$R^5$ is independently selected from H, $C_1$-$C_6$ alkyl, —$(CR^2{}_2)_n$aryl, and —$(CR^2{}_2)_n$heterocyclyl, wherein alkyl, aryl or heterocyclyl may be optionally substituted with one to three substituent selected from $R^7$;
$R^7$ is independently selected from unsubstituted or substituted $C_1$-$C_6$ alkyl, $OR^5$, —$(CR^2{}_2)_n$aryl, CN, $CF_3$ and halo;

R[8] is unsubstituted or substituted phenyl or unsubstituted or substituted thienyl;
R[12] is NH$_2$, OH, or NH-Boc;
m is 1, 2 or 3;
n is independently 0, 1, 2, 3 or 4;
p is 0, 1, 2, or 3;
s is 0, or 1;
or a stereoisomer or a pharmaceutically acceptable salt thereof.

A further embodiment of the invention is a compound of Formula III,

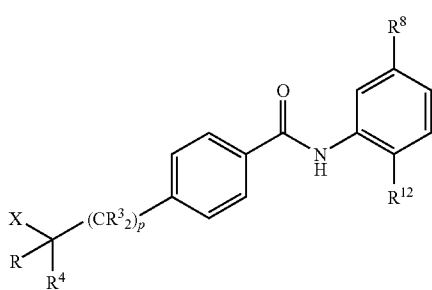

wherein
X is 1) —(CR$^2$$_2$)$_n$C(O)OR$^1$,
2) —(CR$^2$$_2$)$_n$C(O)NR$^1$$_2$,
3) —(CR$^2$$_2$)$_n$C(O)R$^5$, or
4) —(CR$^2$$_2$)$_n$aryl, wherein aryl is optionally substituted with one to three substituent selected from R$^7$;
R is H or unsubstituted or substituted C$_1$-C$_6$ alkyl;
R$^1$ is independently selected from H, C$_1$-C$_6$ alkyl, —(CR$^2$$_2$)$_n$aryl, and —(CR$^2$$_2$)$_n$heterocyclyl;
  wherein said alkyl, aryl or heterocyclyl is optionally substituted with one to three substituent selected from R$^7$;
R$^2$ and R$^3$ are independently selected from H, unsubstituted or substituted C$_1$-C$_6$ alkyl, and (CR$^2$$_2$)$_n$aryl;
R$^4$ is
1) —(CR$^2$$_2$)$_n$NR$^5$$_2$,
2) —(CR$^2$$_2$)$_n$NR$^5$C(O)R$^5$,
3) —(CR$^2$$_2$)$_n$NR$^5$C(O)OR$^5$,
4) —(CR$^2$$_2$)$_n$heterocyclyl,
5) —(CR$^2$$_2$)$_n$NR$^5$S(O)$_2$R$^5$, or
6) —(CR$^2$$_2$)$_n$NR$^5$C(O)NR$^5$$_2$;
  wherein heterocyclyl is optionally substituted with one to three substituent selected from R$^7$;
R$^5$ is independently selected from H, C$_1$-C$_6$ alkyl, —(CR$^2$$_2$)$_n$aryl, and —(CR$^2$$_2$)$_n$heterocyclyl, wherein alkyl, aryl or heterocyclyl may be optionally substituted with one to three substituent selected from R$^7$;
R$^7$ is independently selected from unsubstituted or substituted C$_1$-C$_6$ alkyl, OR$^5$, —(CR$^2$$_2$)$_n$aryl, CN, CF$_3$ and halo;
R$^8$ is phenyl or thienyl;
R$^{12}$ is NH$_2$;
n is independently 0, 1, 2, 3 or 4;
p is 0, 1, 2, or 3;
or a stereoisomer or a pharmaceutically acceptable salt thereof.

Specific embodiments depicting non-limiting Examples of the compounds of the instant invention are provided in the Experimental Section hereinbelow.

Specific examples of the compounds of the instant invention include:
amino[4-({[2-amino-5-(2-thienyl)phenyl]amino}carbonyl)phenyl]acetic acid;
ethyl amino [4-({[2-amino-5-(2-thienyl)phenyl]amino}carbonyl)phenyl]acetate;
4-[1-amino-2-(methylamino)-2-oxoethyl]-N-[2-amino-5-(2-thienyl)phenyl]benzamide;
N-[2-amino-5-(2-thienyl)phenyl]-4-(1,2-diamino-2-oxoethyl)benzamide;
4-{1-amino-2-oxo-2-[(2,2,2-trifluoroethyl)amino]ethyl}-N-[2-amino-5-(2-thienyl)phenyl]benzamide;
4-{1-amino-2-[(2-methoxyphenyl)amino]-2-oxoethyl}-N-(4-amino-1-phenyl-1H-pyrazol-3-yl)benzamide;
4-[1-amino-2-(isoxazol-3 ylamino)-2-oxoethyl]-N-(4-amino-1-phenyl-1H-pyrazol-3-yl)benzamide;
4-[1-amino-2-oxo-2-(pyridin-2-ylamino)ethyl]-N-(4-amino-1-phenyl-1H-pyrazol-3-yl)benzamide;
4-{1-amino-2-[(4-methyl-1,3-thiazol-2-yl)amino]-2-oxoethyl}-N-(4-amino-1-phenyl-1H-pyrazol-3-yl)benzamide;
4-{1-amino-2-[(3-methoxyphenyl)amino]-2-oxoethyl}-N-(4-amino-1-phenyl-1H-pyrazol-3-yl)benzamide;
4-{1-amino-2-[(4-cyanopyridin-2-yl)amino]-2-oxoethyl}-N-(4-amino-1-phenyl-1H-pyrazol-3-yl)benzamide;
4-[1-amino-2-(2,3-dihydro-1,4-benzodioxin-6-ylamino)-2-oxoethyl]-N-(4-amino-1-phenyl-1H-pyrazol-3-yl)benzamide;
ethyl [4-({[2-amino-5-(2-thienyl)phenyl]amino}carbonyl)phenyl]{[(pyridin-3-ylmethoxy)carbonyl]amino}acetate;
[4-({[2-amino-5-(2-thienyl)phenyl]amino}carbonyl)phenyl]{[(pyridin-3-ylmethoxy)carbonyl]amino}acetic acid;
pyridin-3-ylmethyl [1-[4-({[2-amino-5-(2-thienyl)phenyl]amino}-carbonyl)phenyl]-2-(methylamino)-2-oxoethyl]carbamate;
pyridin-3-ylmethyl {2-amino-1-[4-({[2-amino-5-(2-thienyl)phenyl]amino}carbonyl)phenyl]-2-oxoethyl}carbamate;
pyridin-3-ylmethyl [1-[4-({[2-amino-5-(2-thienyl)phenyl]amino}carbonyl)phenyl]-2-(ethylamino)-2-oxoethyl]carbamate;
pyridin-3-ylmethyl [1-[4-({[2-amino-5-(2-thienyl)phenyl]amino}carbonyl)phenyl]-2-(isopropylamino)-2-oxoethyl]carbamate;
pyridin-3-ylmethyl [1-[4-({[2-amino-5-(2-thienyl)phenyl]amino}carbonyl)phenyl]-2-(dimethylamino)-2-oxoethyl]carbamate;
(acetylamino)[4-({[2-amino-5-(2-thienyl)phenyl]amino}carbonyl)phenyl]acetic acid;
4-[1-(acetylamino)-2-oxo-2-pyrrolidin-1-ylethyl]-N-[2-amino-5-(2-thienyl)phenyl]benzamide;
4-[1-(acetylamino)-2-amino-2-oxoethyl]-N-[2-amino-5-(2-thienyl)phenyl]benzamide;
4-[1-(acetylamino)-2-(methylamino)-2-oxoethyl]-N-[2-amino-5-(2-thienyl)phenyl]benzamide;
4-[1-(acetylamino)-2-(dimethylamino)-2-oxoethyl]-N-[2-amino-5-(2-thienyl)phenyl]benzamide;
4-[1-(acetylamino)-2-(isopropylamino)-2-oxoethyl]-N-[2-amino-5-(2-thienyl)phenyl]benzamide;
4-[1-(acetylamino)-2-(ethylamino)-2-oxoethyl]-N-[2-amino-5-(2-thienyl)phenyl]benzamide;
Tert-butyl [2-({4-[1-(acetylamino)-2-(methylamino)-2-oxoethyl]benzoyl}amino)-4-(2-thienyl)phenyl]carbamate;
N-[2-amino-5-(2-thienyl)phenyl]-4-[2-(methylamino)-2-oxo-1-pyrrolidin-1-ylethyl]benzamide;
[4-({[2-amino-5-(2-thienyl)phenyl]amino}carbonyl)phenyl](pyrrolidin-1-yl)acetic acid;
N-[2-amino-5-(2-thienyl)phenyl]-4-[2-(isopropylamino)-1-(4-methylpiperidin-1-yl)-2-oxoethyl]benzamide;
N-(2-amino-5-thien-2-ylphenyl)-4-{1-azetidin-1-yl-2-[(4-methylphenyl)amino]-2-oxoethyl}benzamide;
N-(2-amino-5-thien-2-ylphenyl)-4-[1-(diethylamino)-2-(isopropylamino)-2-oxoethyl]benzamide;

N-(2-amino-5-thien-2-ylphenyl)-4-[1-azetidin-1-yl-2-(isopropylamino)-2-oxoethyl]benzamide;
N-(2-amino-5-thien-3-ylphenyl)-5-[2-[(4-chlorophenyl)amino]-1-(4-methylpiperazin-1-yl)-2-oxoethyl]thiophene-2-carboxamide;
N-(2-amino-5-thien-2-ylphenyl)-5-[2-[(4-chlorophenyl)amino]-1-(4-methylpiperazin-1-yl)-2-oxoethyl]thiophene-2-carboxamide;
N-(2-aminophenyl)-4-[1-(benzoylamino)-2-(benzylamino)-2-oxoethyl]benzamide;
N-(2-aminophenyl)-4-[1,2-bis(benzylamino)-2-oxoethyl]benzamide;
N-(2-aminophenyl)-4-{2-(benzylamino)-2-oxo-1-[(2-phenylethyl)amino]ethyl Benzamide;
N-(2-aminophenyl)-4-{1-(benzoylamino)-2-[(4-chlorophenyl)amino]-2-oxoethyl}benzamide;
N-(2-aminophenyl)-4-{2-[(4-chlorophenyl)amino]-2-oxo-1-[(phenylacetyl)amino]ethyl}benzamide;
N-(2-aminophenyl)-4-{2-[(4-chlorophenyl)amino]-2-oxo-1-[(3-phenylpropanoyl)amino]ethyl}benzamide;
N-(2-aminophenyl)-4-{1-(benzoylamino)-2-[(4-methylphenyl)amino]-2-oxoethyl}benzamide;
N-(2-aminophenyl)-4-[1-(benzoylamino)-2-(2-naphthylamino)-2-oxoethyl]benzamide;
N-(2-aminophenyl)-4-{2-[(4-methylphenyl)amino]-2-oxo-1-[(phenylacetyl)amino]ethyl}benzamide;
N-(2-aminophenyl)-4-{2-[(4-methoxyphenyl)amino]-2-oxo-1-[(phenylacetyl)amino]ethyl}benzamide;
N-(2-aminophenyl)-4-{2-(2-naphthylamino)-2-oxo-1-[(phenylacetyl)amino]ethyl}benzamide;
N-(2-aminophenyl)-4-{2-[(4-methylphenyl)amino]-2-oxo-1-[(3-phenylpropanoyl)amino]ethyl}benzamide;
N-(2-aminophenyl)-4-{2-[(4-methoxyphenyl)amino]-2-oxo-1-[(3-phenylpropanoyl)amino]ethyl}benzamide;
N-(2-aminophenyl)-4-{2-(2-naphthylamino)-2-oxo-1-[(3-phenylpropanoyl)amino]ethyl}benzamide;
N-(2-aminophenyl)-4-[2-(benzylamino)-1-(4-methylpiperazin-1-yl)-2-oxoethyl]-benzamide;
N-(2-aminophenyl)-4-[2-[(4-chlorophenyl)amino]-1-(4-methylpiperazin-1-yl)-2-oxoethyl]benzamide;
N-(2-aminophenyl)-4-[2-[(4-chlorophenyl)amino]-1-(4-methylpiperazin-1-yl)-2-oxoethyl]benzamide;
N-(2-aminophenyl)-4-[1-(4-methylpiperazin-1-yl)-2-(2-naphthylamino)-2-oxoethyl]benzamide;
N-(2-aminophenyl)-4-{2-[(4-chlorophenyl)amino]-1-[(3S)-3-methylpiperazin-1-yl]-2-oxoethyl}benzamide;
N-(2-aminophenyl)-4-[2-(2-naphthylamino)-2-oxo-1-piperazin-1-ylethyl]benzamide;
N-(2-aminophenyl)-4-[2-(2-naphthylamino)-2-oxo-1-(4-phenylpiperazin-1-yl)ethyl]benzamide;
N-(2-aminophenyl)-4-{2-(2-naphthylamino)-2-oxo-1-[4-(2-phenylethyl)piperazin-1-yl]ethyl}benzamide;
N-(2-aminophenyl)-4-[1-morpholin-4-yl-2-(2-naphthylamino)-2-oxoethyl]benzamide;
N-(2-aminophenyl)-6-{2-[(4-chlorophenyl)amino]-2-oxo-1-[(3-phenylpropanoyl)-amino]ethyl}nicotinamide;
N-(2-aminophenyl)-6-[1-(4-methylpiperazin-1-yl)-2-(2-naphthylamino)-2-oxoethyl]nicotinamide;
N-(4-aminobiphenyl-3-yl)-4-[2-[(4-chlorophenyl)amino]-1-(4-methylpiperazin-1-yl)-2-oxoethyl]benzamide;
N-(4-aminobiphenyl-3-yl)-4-[2-[(4-chlorophenyl)amino]-1-(4-methylpiperazin-1-yl)-2-oxoethyl]benzamide;
N-(4-aminobiphenyl-3-yl)-6-[1-(4-methylpiperazin-1-yl)-2-(2-naphthylamino)-2-oxoethyl]nicotinamide;
N-(4-aminobiphenyl-3-yl)-6-[2-(benzylamino)-1-(4-methylpiperazin-1-yl)-2-oxoethyl]nicotinamide;
N-(4-aminobiphenyl-3-yl)-6-[2-[(4-methylphenyl)amino]-1-(4-methylpiperazin-1-yl)-2-oxoethyl]nicotinamide;
N-(4-aminobiphenyl-3-yl)-6-[2-[(4-chlorophenyl)amino]-1-(4-methylpiperazin-1-yl)-2-oxoethyl]nicotinamide;
N-(2-aminophenyl)-4-[3-[(4-chlorophenyl)amino]-2-(4-methylpiperazin-1-yl)-3-oxopropyl]benzamide;
N-(2-aminophenyl)-4-[2-(4-methylpiperazin-1-yl)-3-(2-naphthylamino)-3-oxopropyl]benzamide;
N-(4-aminobiphenyl-3-yl)-4-[3-[(4-chlorophenyl)amino]-2-(4-methylpiperazin-1-yl)-3-oxopropyl]benzamide;
N-(4-aminobiphenyl-3-yl)-4-[3-(benzylamino)-2-(4-methylpiperazin-1-yl)-3-oxopropyl]benzamide;
N-(4-aminobiphenyl-3-yl)-4-[3-[(4-methoxyphenyl)amino]-2-(4-methylpiperazin-1-yl)-3-oxopropyl]benzamide;
N-(4-aminobiphenyl-3-yl)-4-[3-[(4-methylphenyl)amino]-2-(4-methylpiperazin-1-yl)-3-oxopropyl]benzamide;
N-(4-aminobiphenyl-3-yl)-4-[2-(4-methylpiperazin-1-yl)-3-(2-naphthylamino)-3-oxopropyl]benzamide;
4-{[(2-Aminophenyl)amino]carbonyl}-Nα-benzoyl-N-(4-chlorophenyl)phenyl-alaninamide;
N-(4-aminobiphenyl-3-yl)-4-[4-[(4-chlorophenyl)amino]-3-(4-methylpiperazin-1-yl)-4-oxobutyl]benzamide;
N-(4-aminobiphenyl-3-yl)-4-[4-(benzylamino)-3-(4-methylpiperazin-1-yl)-4-oxobutyl]benzamide;
N-(4-aminobiphenyl-3-yl)-4-[3-(4-methylpiperazin-1-yl)-4-(2-naphthylamino)-4-oxobutyl]benzamide;
N-(4-aminobiphenyl-3-yl)-4-[4-[(4-methylphenyl)amino]-3-(4-methylpiperazin-1-yl)-4-oxobutyl]benzamide;
N-(4-aminobiphenyl-3-yl)-4-[4-[(4-methoxyphenyl)amino]-3-(4-methylpiperazin-1-yl)-4-oxobutyl]benzamide;
Benzyl [(1S)-1-[4-({[2-amino-5-(2-thienyl)phenyl]amino}carbonyl)benzyl]-2-(ethylamino)-2-oxoethyl}carbamate;
Benzyl [(1S)-1-[4-({[2-amino-5-(3-thienyl)phenyl]amino}carbonyl)benzyl]-2-(ethylamino)-2-oxoethyl}carbamate;
Benzyl [(1S)-1-[4-({[2-amino-5-(2-thienyl)phenyl]amino}carbonyl)benzyl]-2-(methylamino)-2-oxoethyl]carbamate;
Benzyl [(1S)-1-[4-({[2-amino-5-(3-thienyl)phenyl]amino}carbonyl)benzyl]-2-(methylamino)-2-oxoethyl]carbamate;
Benzyl [(1S)-1-[4-({[2-amino-5-(2-thienyl)phenyl]amino}carbonyl)benzyl]-2-(4-methylpiperazin-1-lyl)-2-oxoethyl]carbamate;
Benzyl [(1S)-1-[4-({[2-amino-5-(2-thienyl)phenyl]amino}carbonyl)benzyl]-2-morpholin-4-yl-2-oxoethyl]carbamate;
Benzyl [(1S)-1-[4-({[2-amino-5-(2-thienyl)phenyl]amino}carbonyl)benzyl]-2-{[2-(dimethylamino)ethyl]amino}-2-oxoethyl]carbamate;
Benzyl [(1S)-1-[4-({[2-amino-5-(2-thienyl)phenyl]amino}carbonyl)benzyl]-2-(benzylamino)-2-oxoethyl]carbamate;
Benzyl {(1S)-2-amino-1-[4-({[2-amino-5-(2-thienyl)phenyl]amino}carbonyl)benzyl]-2-oxoethyl}carbamate;
(2S)-3-[4-({[2-amino-5-(2-thienyl)phenyl]amino}carbonyl)phenyl]-2-{[(benzyloxy)carbonyl]amino}propanoic acid;
Benzyl [(1S)-1-[4-({[2-amino-5-(2-thienyl)phenyl]amino}carbonyl)benzyl]-2-(dimethylamino)-2-oxoethyl]carbamate;
Benzyl [(1S)-1-[4-({[2-amino-5-(2-thienyl)phenyl]amino}carbonyl)benzyl]-2-(isopropylamino)-2-oxoethyl]carbamate;

Benzyl [(1S)-1-[4-({[2-amino-5-(3-thienyl)phenyl]amino}carbonyl)benzyl]-2-oxo-2-(propylamino)ethyl]carbamate;
Benzyl [(1S)-1-[4-({[2-amino-5-(3-thienyl)phenyl]amino}carbonyl)benzyl]-2-(cyclopropylamino)-2-oxoethyl]carbamate;
Benzyl {(1S)-1-[4-({[2-amino-5-(2-thienyl)phenyl]amino}carbonyl)benzyl]-2-[(2-methoxyethyl)amino)-2-oxoethyl}carbamate;
Benzyl ((1S)-1-[4-({[2-amino-5-(2-thienyl)phenyl]amino}carbonyl)benzyl]-2-{[2-(dimethylamino)-2-oxoethyl]amino}-2-oxoethyl)carbamate;
Benzyl {(1S)-1-[4-({[2-amino-5-(2-thienyl)phenyl]amino}carbonyl)benzyl]-2-[[2-(dimethylamino)-2-oxoethyl](methyl)amino]-2-oxoethyl}carbamate;
Benzyl {(1S)-2-{[2-(acetylamino)ethyl]amino}-1-[4-({[2-amino-5-(2-thienyl)phenyl]amino}carbonyl)benzyl]-2-oxoethyl}carbamate;
Benzyl {(1S)-2-({2-[acetyl(methyl)amino]ethyl}amino)-1-[4-({[2-amino-5-(2-thienyl)phenyl]amino}carbonyl)benzyl]-2-oxoethyl}carbamate;
Benzyl [1(S)-(4-{[4-amino-1-phenyl-1H-pyrazol-3-yl)amino]carbonyl}benzyl)-2-(methylamino)-2-oxoethyl]carbamate;
4-[(2S)-2-(acetylamino)-3-(methylamino)-3-oxopropyl]-N-2-amino-5-(2-thienyl)phenyl]benzamide;
4-[(2S)-2-(acetylamino)-3-(4-methylpiperzin-1-yl)-3-oxopropyl]-N-2-amino-5-(2-thienyl)phenyl]benzamide;
4-[(2S)-2-(acetylamino)-3-morpholin-4-yl-3-oxopropyl]-N-2-amino-5-(2-thienyl)phenyl]benzamide;
4-[(2S)-2-(acetylamino)-3-{[2-(dimethylamino)ethyl]amino}-3-oxopropyl]-N-(2-amino-5-(2-thienyl)phenyl]benzamide;
4-[(2S)-2-(acetylamino)-3-(ethylamino)-3-oxopropyl]-N-[2-amino-5-(2-thienyl)phenyl]benzamide;
4-[(2S)-2-(acetylamino)-3-(benzylamino)-3-oxopropyl]-N-[2-amino-5-(2-thienyl)phenyl]benzamide;
N-[2-amino-5-(2-thienyl)phenyl]-4-{(2S)-2-[(methylsulfonyl)amino]-3-morpholin-4-yl-3-oxopropyl}benzamide;
N-[2-amino-5-(2-thienyl)phenyl]-4-{(2S)-3-(ethylamino)-2-[(methylsulfonyl)amino]-3-oxopropyl}benzamide;
N-[2-amino-5-(2-thienyl)phenyl]-4-{(2S)-3-(benzylamino)-2-[(methylsulfonyl)amino]-3-oxopropyl}benzamide;
pyridin-3-ylmethyl[(1S)-1-[4-({[2-amino-5-(2-thienyl)phenyl]amino}carbonyl)benzyl]-2-(ethylamino)-2-oxoethyl]carbamate;
pyridin-3-ylmethyl [(1S)-1-[4-({[2-amino-5-(2-thienyl)phenyl]amino}carbonyl)benzyl]-2-(methylamino)-2-oxoethyl]carbamate;
N-[(1S)-1-[4-({[2-amino-5-(3-thienyl)phenyl]amino}carbonyl)benzyl]-2-oxo-2-(propylamino)ethyl]thiophene-2-carboxamide;
4-[(2S)-2-amino-3-(ethylamino)-3-oxopropyl]-N-[2-amino-5-(2-thienyl)phenyl]benzamide;
4-[(2S)-2-amino-3-(methylamino)-3-oxopropyl]-N-[2-amino-5-(2-thienyl)phenyl]benzamide;
4-((2S)-2-amino-3-{[2-(dimethylaminoethyl]amino}-3-oxopropyl)-N-[2-amino-5-(2-thienyl)phenyl]benzamide;
4-{(2S)-2-amino-3-[(2-methoxyethyl)amino]-3-oxopropyl}-N-[2-amino-5-(2-thienyl)phenyl]benzamide;
2-amino-3-[4-({[2-amino-5-(3-thienyl)phenyl]amino}carbonyl)phenyl]propanoic acid;
Ethyl 3-[4-({[2-amino-5-(2-thienyl)phenyl]amino}carbonyl)phenyl]-2-(dimethylamino)propanoate;
4-[1-(acetylamino)-2-amino-2-oxoethyl]-N-[2-(acetylamino)-5-(2-thienyl)phenyl]benzamide;
N-[2-amino-5-(2-thienyl)phenyl]-4-{2-(methylamino)-1-[(methylsulfonyl)amino]-2-oxoethyl}benzamide;
N-[2-amino-5-(2-thienyl)phenyl]-4-(2-(methylamino)-1-{[(methylamino)carbonyl]amino}-2-oxoethyl)benzamide;
4-{1-[(Acetylamino)methyl]-2-anilino-2-oxoethyl}-N-[2-amino-5-(3-thienyl)phenyl]benzamide;
N-[2-Amino-5-(3-thienyl)phenyl]-4-[2-anilino-1-({[(methylamino)carbonyl]amino}methyl)-2-oxo-ethyl]benzamide;
N-[2-Amino-5-(3-thienyl)phenyl]-4-{2-anilino-1-[(dimethylamino)methyl]-2-oxoethyl}benzamide;
4-{1-[(acetylamino)methyl]-2-anilino-2-oxoethyl}-N-[2-amino-5-(3-thienyl)phenyl]benzamide;
4-[1-[(acetylamino)methyl]-2-(methylamino)-2-oxoethyl]-N-[2-amino-5-(3-thienyl)phenyl]benzamide;
4-[1-[(acetylamino)methyl]-2-(dimethylamino)-2-oxoethyl]-N-[2-amino-5-(3-thienyl)phenyl]benzamide;
4-{1-[(acetylamino)methyl]-2-morpholin-4-yl-2-oxoethyl}-N-[2-amino-5-(3-thienyl)phenyl]benzamide;
N-[2-amino-5-(3-thienyl)phenyl]-4-{2-anilino-1-[(dimethylamino)methyl]-2-oxoethyl}benzamide;
N-[2-amino-5-(3-thienyl)phenyl]-4-[1-[(dimethylamino)methyl]-2-(methylamino)-2-oxoethyl]benzamide;
N-[2-amino-5-(3-thienyl)phenyl]-4-(2-anilino-1-{[(methylsulfonyl)amino]methyl}-2-oxoethyl)benzamide;
N-[2-amino-5-(3-thienyl)phenyl]-4-(2-(methylamino)-1-{[(methylsulfonyl)amino]methyl}-2-oxoethyl)benzamide;
N-[2-amino-5-(3-thienyl)phenyl]-4-(2-(dimethylamino)-1-{([(methylsulfonyl)amino]methyl}-2-oxoethyl)benzamide;
N-[2-amino-5-(3-thienyl)phenyl]-4-[2-anilino-1-({[(methylamino)carbonyl]amino}methyl)-2-oxoethyl]benzamide;
N-[2-amino-5-(3-thienyl)phenyl]-4-[2-(methylamino)-1-({[(methylamino)carbonyl]amino}methyl)-2-oxoethyl]benzamide;
N-[2-amino-5-(3-thienyl)phenyl]-4-[2-(dimethylamino)-1-({[(methylamino)carbonyl]amino}methyl)-2-oxoethyl]benzamide;
[4-({[2-[(tert-butoxycarbonyl)amino]-5-(2-thienyl)phenyl]amino}carbonyl)phenyl] (pyrrolidin-1-yl)acetic acid;

or a stereoisomer or a pharmaceutically acceptable salt thereof.

Chemical Definitions

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. The cycloalkyl is optionally bridged (i.e., forming a bicyclic moiety), for example with a methylene, ethylene or propylene bridge. The bridge may be optionally substituted or branched. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on. In an embodiment, if the number of carbon atoms is not specified, "alkyl" refers to $C_1$-$C_{12}$ alkyl and in a further embodiment, "alkyl" refers to $C_1$-$C_6$ alkyl. In an embodiment, if the number of carbon atoms is not specified, "cycloalkyl" refers to $C_3$-$C_{10}$ cycloalkyl and in a further embodiment, "cycloalkyl" refers to $C_3$-$C_7$ cycloalkyl. In an embodiment, examples of "alkyl" include methyl, ethyl, n-propyl, i-propyl, n-butyl, i-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

When used in the phrases "alkylaryl", "alkylcycloalkyl" and "alkylheterocyclyl" the term "alkyl" refers to the alkyl portion of the moiety and does not describe the number of atoms in the aryl and heteroaryl portion of the moiety. In an embodiment, if the number of carbon atoms is not specified, "alkyl" of "alkylaryl", "alkylcycloalkyl" and "alkylheterocyclyl" refers to $C_1$-$C_{12}$ alkyl and in a further embodiment, the term refers to $C_1$-$C_6$ alkyl.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms; Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

In one embodiment, as used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In another embodiment, "aryl" is an aromatic ring of 5 to 14 carbons atoms, and includes a carbocyclic aromatic group fused with a 5- or 6-membered cycloalkyl group such as indan. Examples of carbocyclic aromatic groups include, but are not limited to, phenyl, naphthyl, e.g., 1-naphthyl and 2-naphthyl; anthracenyl, e.g., 1-anthracenyl, 2-anthracenyl; phenanthrenyl; fluorenonyl, e.g., 9-fluorenonyl, indanyl and the like. A carbocyclic aromatic group is optionally substituted with a designated number of substituents, described below.

The term heteroaryl, as used herein, represents a stable monocyclic, bicyclic or tricyclic ring of up to 7 atoms in each ring, wherein at, least one ring is aromatic and contains from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment can be via the aromatic ring, the non-aromatic ring, or via the heteroatom containing ring.

In another embodiment, "heteroaryl" is a monocyclic, bicyclic or tricyclic aromatic ring of 5- to 14-ring atoms of carbon and from one to four heteroatoms selected from O, N, or S. Examples of heteroaryl include, but are not limited to pyridyl, e.g., 2-pyridyl (also referred to as α-pyridyl), 3-pyridyl (also referred to as β-pyridyl) and 4-pyridyl (also referred to as (γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazoyl, 4-oxazoyl and 5-oxazoyl; isoxazoyl; pyrrolyl; pyridazinyl; pyrazinyl and the like. Heterocyclic aromatic (or heteroaryl) as defined above may be optionally substituted with a designated number of substituents, as described below for aromatic groups.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g., 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g., 2-benzofuranyl and 3-benzofuranyl; dibenzofuranyl, e.g., 2,3-dihydrobenzofuranyl; dibenzothiophenyl; benzothienyl, e.g., 2-benzothienyl and 3-benzothienyl; indolyl, e.g., 2-indolyl and 3-indolyl; benzothiazolyl, e.g., 2-benzothiazolyl; benzooxazolyl, e.g., 2-benzooxazolyl; benzimidazolyl, e.g., 2-benzoimidazolyl; isoindolyl, e.g., 1-isoindolyl and 3-isoindolyl; benzotriazolyl; purinyl; thianaphthenyl, pyrazinyland the like. Fused polycyclic aromatic ring systems may optionally be substituted with a designated number of substituents, as described herein.

The term "heterocycle" or "heterocyclyl" as used herein is intended to mean a 3- to 14-membered monocyclic, bicyclic or tricyclic aromatic or nonaromatic heterocycle containing from 1 to 4 heteroatoms selected from the group consisting of O, N, S or P. A nonaromatic heterocycle may be fused with an aromatic aryl group such as phenyl or aromatic heterocycle.

"Heterocyclyl" therefore includes the above mentioned heteroaryls, as well as dihydro and tetrathydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, "heterocycle" (also referred to herein as "heterocyclyl"), is a monocyclic, bicyclic or tricyclic saturated or unsaturated ring of 5- to 14-ring atoms of carbon and from one to four heteroatoms selected from O, N, S or P. Examples of heterocyclic rings include, but are not limited to: pyrrolidinyl, piperidinyl, morpholinyl, thiamorpholinyl, piperazinyl, dihydrofuranyl, tetrahydrofuranyl, dihydropyranyl, tetrahydrodropyranyl, dihydroquinolinyl, tetrahydroquinolinyl, dihydroisoquinolinyl, tetrahydroisoquinolinyl, dihydropyrazinyl, tetrahydropyrazinyl, dihydropyridyl, tetrahydropyridyl, pyrazolyl, pyridazinyl, pyridyl, pyrimidyl, pyrrolyl, quinazolinyl, quinolyl and the like.

An "alkylaryl group" (arylalkyl) is an alkyl group substituted with an aromatic group, preferably a phenyl group. A preferred alkylaryl group is a benzyl group. Suitable aromatic groups are described herein and suitable alkyl groups are described herein. Suitable substituents for an alkylaryl group are described herein.

An "alkylheterocyclyl" group is an alkyl group substituted with a heterocyclyl group. Suitable heterocyclyl groups are described herein and suitable alkyl groups are described herein. Suitable substituents for an alkylheterocyclyl group are described herein.

An "alkylcycloalkyl group" is an alkyl group substituted with a cycloalkyl group. Suitable cycloalkyl groups are described herein and suitable alkyl groups are described herein. Suitable substituents for an alkycycloalkyl group are described herein.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

As used herein, an "arylalkylamino group" is an arylalkyl group that is attached to a compound via a nitrogen on the alkyl portion of the arylalkyl.

An "alkylsulfonyl group" as used herein, is an alkyl group that is attached to a compound via the sulfur of a sulfonyl group.

As used herein, many moieties or groups are referred to as being either "substituted or unsubstituted". When a moiety is referred to as substituted, it denotes that any portion of the moiety that is known to one skilled in the art as being available for substitution can be substituted. The phrase "optionally substituted with one or more substituents" means one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl groups (which can also be substituted, with one or more substituents), alkoxy groups (which can be substituted), a halogen or halo group (F, Cl, Br, I), hydroxy, nitro, oxo, —CN, —$CF_3$, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—NHR, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), alkylsulfonyl (which can be substituted), aryl (which can be substituted), cycloalkyl (which can be substituted) alkylaryl (which can be substituted), heterocyclyl (which can be substituted), alkylheterocyclyl (which can be substituted), alkylcycloalkyl (which can be substituted), and aryloxy.

In an embodiment, X is —$(CR^2_2)_nC(O)OR^1$, —$(CR^2_2)_nC(O)NR^1_2$, —$(CR^2_2)_nC(O)R^5$, or —$(CR^2_2)_n$aryl, wherein aryl is optionally substituted. In another embodiment, X is —$(CR^2_2)_nC(O)OR^1$, —$(CR^2_2)_nC(O)NR^1_2$, or —$(CR^2_2)_nC(O)R^5$.

In an embodiment, R is H.

In an embodiment, $R^3$ is H or unsubstituted or substituted $C_1$-$C_6$ alkyl.

In an embodiment, $R^4$ is —$(CR^2_2)_nNR^5_2$, —$(CR^2_2)_nNR^5C(O)R^5$, —$(CR^2_2)_nNR^5C(O)OR^5$, —$(CR^2_2)_n$heterocyclyl, —$(CR^2_2)_nNR^5S(O)_2R^5$, or —$(CR^2_2)_nNR^5C(O)NR^5_2$, wherein heterocyclyl is optionally substituted. In another embodiment, $R^4$ is —$(CR^2_2)_nNR^5_2$, —$(CR^2_2)_nNR^5C(O)R^5$, —$(CR^2_2)_nNR^5C(O)OR^5$, or —$(CR^2_2)_n$heterocyclyl, wherein heterocyclyl is optionally substituted.

In an embodiment, $R^5$ is H, unsubstituted or substituted $C_1$-$C_6$ alkyl, —$(CR^2_2)_n$aryl, or —$(CR^2_2)_n$heterocyclyl, wherein alkyl, aryl or heterocyclyl may be optionally substituted.

In an embodiment, $R^7$ is independently selected from unsubstituted or substituted $C_1$-$C_6$ alkyl, $OR^5$, —$(CR^2_2)_n$aryl, CN, $CF_3$ and halo.

In an embodiment, $R^8$ is phenyl or thienyl. In another embodiment, $R^8$ is thienyl. In another embodiment, $R^8$ is phenyl.

In an embodiment, $R^{12}$ is $NH_2$, $NHC(O)R^5$, or NH-Boc. In another embodiment, $R^{12}$ is $NH_2$ or NH-Boc. In another embodiment, $R^{12}$ is $NH_2$.

In an embodiment, n is 0, 1, 2, 3 or 4. In another embodiment, n is 0, 1, or 2. In another embodiment, n is 1, 2, 3 or 4.

In an embodiment, p is 0, 1, 2 or 3. In another embodiment, p is 0, 1 or 2.

In an embodiment, s is 0 or 1. In another embodiment, s is 1.

In an embodiment, Y is phenyl, thienyl or pyridyl; Z is phenyl or pyrazolyl; $R^8$ is thienyl or phenyl; s is 1; $R^{12}$ is $NH_2$; R is H; X is $-(CR^2{}_2)_nC(O)OR^1$, $-(CR^2{}_2)_nC(O)NR^1{}_2$, or $-(CR^2{}_2)_nC(O)R^5$; and $R^4$ is $-(CR^2{}_2)_nNR^5{}_2$, $-(CR^2{}_2)_n NR^5C(O)R^5$, $-(CR^2{}_2)_nNR^5C(O)OR^5$, or $-CR^2{}_2)_n$heterocyclyl, wherein heterocyclyl is optionally substituted.

In an embodiment, Y is phenyl, Z is phenyl, s is 1, $R^8$ is thienyl, $R^{12}$ is $NH_2$; R is H; p is 0, X is $-(CR^2{}_2)_nC(O)NR^1{}_2$, $R^1$ is H or $C_1$-$C_6$ alkyl, $R^4$ is $-(CR^2{}_2)_nNR^5{}_2$, and $R^5$ is H or $C_1$-$C_6$ alkyl, Stereochemistry Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the HDAC inhibitors of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

This invention is also intended to encompass pro-drugs of the compounds of the instant invention disclosed herein. A prodrug of any of the compounds can be made using well-known pharmacological techniques.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

Pharmaceutically Acceptable Salts

The compounds of the instant invention described herein can, as noted above, be prepared in the form of their pharmaceutically acceptable salts. Pharmaceutically acceptable salts are salts that retain the desired biological activity of the parent compound and do not impart undesired toxicological effects. Examples of such salts are acid addition salts, organic and inorganic acids, for example, acid addition salts which may, for example, be hydrochloric acid, sulphuric acid, methanesulphonic acid, fumaric acid, maleic acid, succinic acid, acetic acid, benzoic acid, oxalic acid, citric acid, tartaric acid, carbonic acid, trifluoroacetic acid, formic acid, phosphoric acid and the like. Pharmaceutically acceptable salts can also be prepared from by treatment with inorganic bases, for example, sodium, potassium, ammonium, calcium, or ferric hydroxides, and such organic bases as isopropylamine, trimethylamine, 2-ethylamino ethanol, histidine, procaine, and the like. Pharmaceutically acceptable salts can also salts formed from elemental anions such as chlorine, bromine and iodine.

The active compounds disclosed can, as noted above, also be prepared in the form of their hydrates. The term "hydrate" includes but is not limited to hemihydrate, monohydrate, dihydrate, trihydrate, tetrahydrate and the like.

The active compounds disclosed can, as noted above, also be prepared in the form of a solvate with any organic or inorganic solvent, for example alcohols such as methanol, ethanol, propanol and isopropanol, ketones such as acetone, aromatic solvents and the like.

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

As used herein, "a," an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Methods of Treatment

The invention also relates to methods of using the compounds of the instant invention. As demonstrated herein, the compounds of the present invention are useful for the treatment of cancer. In addition, there is a wide range of other diseases for which substituted nicotinamides may be useful. Non-limiting examples are thioredoxin (TRX)-mediated diseases as described herein, and diseases of the central nervous system (CNS) as described herein.

1. Treatment of Cancer

As demonstrated herein, the compounds of the present invention are useful for the treatment of cancer. Accordingly, in one embodiment, the invention relates to a method of treating cancer in a subject in need of treatment comprising administering to said subject a therapeutically effective amount of the compounds of the instant invention.

The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions and methods of the invention include, but are not limited to: Cardiac: sarcoma (angiosarcoma, fibrosarcoma, rhabdomyosarcotna, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In an embodiment, the instant compounds are useful in the treatment of cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burlitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, colorectal, rectal and colon), lung cancer, breast cancer, pancreatic cancer, melanoma and other skin cancers, stomach cancer, brain tumors, liver cancer and thyroid cancer.

2. Treatment of Thioredoxin (TRX)-mediated Diseases

In another embodiment, the compounds of the instant invention are used in a method of treating a thioredoxin (TRX)-mediated disease or disorder in a subject in need thereof, comprising administering to the subject a therapeutically effective amount of one or more of the compounds of the instant invention.

Examples of TRX-mediated diseases include, but are not limited to, acute and chronic inflammatory diseases, autoimmune diseases, allergic diseases, diseases associated with oxidative stress, and diseases characterized by cellular hyperproliferation.

Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemohorragic shock; hyperalgesia: inflammatory bowel disease; multiple sclerosis; myopathies (e.g., muscle protein metabolism, esp in sepsis); osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes. Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

3. Treatment of Diseases of the Central Nervous System (CNS)

In another embodiment, the compounds of the instant invention are used in a method of treating a disease of the central nervous system in a subject in need thereof comprising administering to the subject a therapeutically effective amount of any one or more of the compounds of the instant invention.

In a particular embodiment, the CNS disease is a neurodegenerative disease. In a further embodiment, the neurodegenerative disease is an inherited neurodegenerative disease, such as those inherited neurodegenerative diseases that are polyglutamine expansion diseases. Generally, neurodegenerative diseases can be grouped as follows:

I. Disorders characterized by progressive dementia in the absence of other prominent neurologic signs, such as Alzheimer's disease; Senile dementia of the Alzheimer type; and Pick's disease (lobar atrophy).

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy).

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome.

IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders).

V. Syndrome of central autonomic nervous system failure (Shy-Drager syndrome).

VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia.

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy.

VIII. Syndromes of progressive visual loss such as pigmentary degeneration of the retina (retinitis pigmentosa), and hereditary optic atrophy (Leber's disease).

Definitions:

The term "treating" in its various grammatical forms in relation to the present invention refers to preventing (i.e., chemoprevention), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

Treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

As used herein, the term "therapeutically effective amount" is intended to encompass any amount that will achieve the desired therapeutic or biological effect. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

In the present invention, when the compounds are used to treat or prevent cancer, the desired biological response is partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

Furthermore, in the present invention, when the compounds are used to treat and/or prevent thioredoxin (TRX)-mediated diseases and conditions, a therapeutically effective amount is an amount that regulates, for example, increases, decreases or maintains a physiologically suitable level of TRX in the subject in need of treatment to elicit the desired therapeutic effect. The therapeutic effect is dependent upon the specific TRX-mediated disease or condition being treated. As such, the therapeutic effect can be a decrease in the severity of symptoms associated with the disease or disorder and/or inhibition (partial or complete) of progression of the disease or disease.

Furthermore, in the present invention, when the compounds are used to treat and/or prevent diseases or disorders of the central nervous system (CNS), a therapeutically effective amount is dependent upon the specific disease or disorder being treated. As such, the therapeutic effect can be a decrease in the severity of symptoms associated with the disease or disorder and/or inhibition (partial or complete) of progression of the disease or disorder.

In addition, a therapeutically effective amount can be an amount that inhibits histone deacetylase.

Further, a therapeutically effective amount, can be an amount that selectively induces terminal differentiation, cell growth arrest and/or apoptosis of neoplastic cells, or an amount that induces terminal differentiation of tumor cells.

The method of the present invention is intended for the treatment or chemoprevention of human patients with cancer. However, it is also likely that the method would be effective in the treatment of cancer in other subjects. "Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

Histone Deacetylases and Histone Deacetylase Inhibitors

As demonstrated herein, the compounds of the present invention show improved activity as histone deacetylase (HDAC) inhibitors. Accordingly, in one embodiment, the invention relates to a method of inhibiting the activity of histone deacetylase comprising contacting the histone deacetylase with an effective amount of one or more of the compounds of the instant invention.

Histone deacetylases (HDACs), as that term is used herein, are enzymes that catalyze the removal of acetyl groups from lysine residues in the amino terminal tails of the nucleosomal core histones. As such, HDACs together with histone acetyl transferases (HATs) regulate the acetylation status of histones. Histone acetylation affects gene expression and inhibitors of HDACs, such as the hydroxamic acid-based hybrid polar compound suberoylanitide hydroxamic acid (SAHA) induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class I HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of NAD dependent enzymes that are related to the yeast SIR2 proteins and are not inhibited by hydroxamic acid-based HDAC inhibitors.

Histone deacetylase inhibitors or HDAC inhibitors, as that term is used herein are compounds that are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes. It is also to be understood that the compounds of the present invention are capable of inhibiting any of the histone deacetylases set forth above, or any other histone deacetylases.

For example, in patients receiving HDAC inhibitors, the accumulation of acetylated histones in peripheral mononuclear cells as well as in tissue treated with HDAC inhibitors can be determined against a suitable control.

HDAC inhibitory activity of a particular compound can be determined in vitro using, for example, an enzymatic assays which shows inhibition of at least one histone deacetylase. Further, determination of the accumulation of acetylated histones in cells treated with a particular composition can be determinative of the HDAC inhibitory activity of a compound.

Assays for the accumulation of acetylated histones are well known in the literature. See, for example, Marks, P. A. et al., J. Natl. Cancer Inst., 92:1210-1215, 2000, Butler, L. M. et al., Cancer Res. 60:5165-5170 (2000), Richon, V. M. et al., Proc. Natl. Acad. Sci., USA, 95:3003-3007, 1998, and Yoshida, M. et al., J. Biol. Chem., 265:17174-17179, 1990.

For example, an enzymatic assay to determine the activity of an HDAC inhibitor compound can be conducted as follows. Briefly, the effect of an HDAC inhibitor compound on affinity purified human epitope-tagged (Flag) HDAC1 can be assayed by incubating the enzyme preparation in the absence of substrate on ice for about 20 minutes with the indicated amount of inhibitor compound. Substrate ([$^3$H]acetyl-labelled murine erythroleukemia cell-derived histone) can be added and the sample can be incubated for 20 minutes at 37° C. in a total volume of 30 µL. The reaction can then be stopped and released acetate can be extracted and the amount of radioactivity release determined by scintillation counting. An alternative assay useful for determining the activity of an HDAC inhibitor compound is the "HDAC Fluorescent Activity Assay; Drug Discovery Kit-AK-500" available from BIO-MOL Research Laboratories, Inc., Plymouth Meeting, Pa.

In vivo studies can be conducted as follows. Animals, for example, mice, can be injected intraperitoneally with an HDAC inhibitor compound. Selected tissues, for example, brain, spleen, liver etc, can be isolated at predetermined times, post administration. Histones can be isolated from tissues essentially as described by Yoshida et al., J. Biol. Chem. 265:17174-17179, 1990. Equal amounts of histones (about 1 µg) can be electrophoresed on 15% SDS-polyacrylamide gels and can be transferred to Hybond-P filters (available from Amersham). Filters can be blocked with 3% milk and can be probed with a rabbit purified polyclonal anti-acetylated histone H4 antibody ($\alpha$Ac-H4) and anti-acetylated histone H3 antibody ($\alpha$Ac-H3) (upstate Biotechnology, Inc.). Levels of acetylated histone can be visualized using a horse-radish peroxidase-conjugated goat anti-rabbit antibody (1:5000) and the SuperSignal chemiluminescent substrate (Pierce). As a loading control for the histone protein, parallel gels can be run and stained with Coomassie Blue (CB).

In addition, hydroxamic acid-based HDAC inhibitors have been shown to up regulate the expression of the $p21^{WAF1}$ gene. The $p21^{WAF1}$ protein is induced within 2 hours of culture with HDAC inhibitors in a variety of transformed cells using standard methods. The induction of the $p21^{WAF1}$ gene is associated with accumulation of acetylated histones in the chromatin region of this gene. Induction of $p21^{WAF1}$ can therefore be recognized as involved in the GI cell cycle arrest caused by HDAC inhibitors in transformed cells.

Combination Therapy

The compounds of the present invention can be administered alone or in combination with other therapies suitable for the disease or disorder being treated. Where separate dosage formulations are used, the compounds of the instant invention and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the compounds of the instant invention and the other therapeutic agent are realized by the patient at substantially the same time. In an embodiment, such beneficial effect is achieved when the target blood level concentrations of each active drug are maintained at substantially the same time.

The instant compounds may also be useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The instant compounds are particularly useful when co-administered with radiation therapy.

In an embodiment, the instant compounds may also be useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, diethylstibestral, tamoxifen, raloxifene, idoxifene, LY353381, LY117081, toremifene, fluoxymestero, lfulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

Other hormonal agents include: aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

"Androgen receptor modulators" refers to compounds which interfere or inhibit the binding of androgens to the receptor, regardless of mechanism. Examples of androgen receptor modulators include finasteride and other 5$\alpha$-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9cis-retinoic acid, $\alpha$-difluoromethyl-ornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptanmine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamio)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-amiopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino) ethyl)acridine-4-carboxamide, 6-[[2-(dimethylamino)ethyl] amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678 and WO 03/39460 and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamiflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofar, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-beptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, 11-acetyl-8-(carbamoyloxymethyl)-4-formyl-6-methoxy-14-oxa-1,11-diazatetracyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S.

Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec, Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs shown as described by Bume-Jensen and Hunter, Nature, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytoline receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134, 142, 5,380,738, 5,393,790, 5,466,823, 5,633,272, and 5,932, 598.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]-methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v \beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 91.16-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with gene therapy for the treatment of cancer. For an overview of genetic-strategies to treating cancer see Hall et al. (*Am J Hum Genet.* 61:785-789, 1997) and Kufe et al (*Cancer Medicine*, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), Duc-4, NF-1, NF-2, RB, WT1, BRCA1, BRCA2, a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92121677, 92122569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95126338, 95/28418, 95/30674, 95/30687, 95/33474, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

In an embodiment, the neurokinin-1 receptor antagonist for use in conjunction with the compounds of the present invention is selected from: 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, bacillus Calmette-Guerin, octreotide, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to anastrozole, letrozole and exemestane.

A compound of the instant invention may also be useful for treating or preventing cancer in combination with siRNA therapeutics.

A compound of the instant invention may also be useful for treating or preventing cancer in combination with compounds which induce terminal differentiation of the neoplastic cells. Suitable differentiation agents include the compounds disclosed in any one or more of the following references.

a) Polar compounds (Marks et al (1987); Friend, C., Scher, W., Holland, J. W., and Sato, T. (1971) *Proc. Natl. Acad. Sci.* (USA) 68: 378-382; Tanaka, M., Levy, J., Terada, M., Breslow, R., Rifkind, R. A., and Marks, P. A. (1975) *Proc. Natl. Acad. Sci.* (USA) 72: 1003-1006; Reuben, R. C., Wife, R. L., Breslow, R., Rifkind, R. A., and Marks, P. A. (1976) *Proc. Natl. Acad. Sci.* (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (USA) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919);

c) Steroid hormones (Lotem, J. and Sachs, L. (1975) *Int. J. Cancer* 15: 731-740);

d) Growth factors (Sachs, L. (1978) *Nature* (Lond.) 274: 535, Metcalf, D. (1985) *Science,* 229: 16-22);

e) Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res. Comm.* 109: 348-354);

f) Tumor promoters (Huberman, E. and Callaham, M. F. (1979) *Proc. Natl. Acad. Sci.* (USA) 76: 1293-1297; Lottem, J. and Sachs, L. (1979) *Proc. Natl. Acad. Sci.* (USA) 76: 5158-5162); and g) inhibitors of DNA or RNA synthesis (Schwartz, E. L. and Sartorelli, A. C. (1982) *Cancer Res.* 42: 2651-2655, Terada, M., Epner, E., Nudel, U., Salmon, J., Fibach, E., Rifkind, R. A., and Marks, P. A. (1978) *Proc. Natl. Acad. Sci.* (USA) 75: 2795-2799; Morin, M. J. and Sartorelli, A. C. (1984) *Cancer Res* 44: 2807-2812; Schwartz, E. L., Brown, B. J., Nierenberg, M., Marsh, J. C., and Sartorelli, A. C. (1983) *Cancer Res.* 43: 2725-2730; Sugano, H., Furusawa, M., Kawaguchi, T., and Ikawa, Y. (1973) *Bibl. Hematol.* 39: 943-954; Ebert, P. S., Wars, I., and Buell, D. N. (1976) *Cancer Res.* 36: 1809-1813; Hayashi, M., Okabe, J., and Hozumi, M. (1979) Gann 70:235-238).

A compound of the instant invention may also be useful for treating or preventing cancer in combination with γ-secretase inhibitors.

Also included in the scope of the claims is a method of treating cancer that comprises administering a therapeutically effective amount of a compound of Formula I in combination with radiation therapy and/or in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The use of all of these approaches in combination with the compounds of Formula I and II, as described herein, are within the scope of the present invention.

Dosages and Dosing Schedules

The dosage regimen utilizing the compounds of the present invention can be selected in accordance with a variety of factors including type, species, age, weight, sex and the type of cancer being treated; the severity (i.e., stage) of the disease to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

For oral administration, suitable daily dosages are for example between about 5-4000 mg/m$^2$ administered orally once-daily, twice-daily or three times-daily, continuous (every day) or intermittently (e.g., 3-5 days a week). For example, when used to treat the desired disease, the dose of the compounds of the instant invention can range between about 2 mg to about 2000 mg per day.

The compound of the instant invention may be administered once daily (QD), or divided into multiple daily doses such as twice daily (BID), and three times daily (TID). For administration once a day, a suitably prepared medicament would therefore contain all of the needed daily dose. For administration twice a day, a suitably prepared medicament would therefore contain half of the needed daily dose. For administration three times a day, a suitably prepared medicament would therefore contain one third of the needed daily dose.

In addition, the administration can be continuous, i.e., every day, or intermittently. The terms "intermittent" or "intermittently" as used herein means stopping and starting at either regular or irregular intervals. For example, intermittent administration of an HDAC inhibitor may be administration one to six days per week or it may mean administration in cycles (e.g., daily administration for two to eight consecutive weeks, then a rest period with no administration for up to one week) or it may mean administration on alternate days.

Typically, an intravenous formulation may be prepared which contains a concentration of the compounds of the instant invention of between about 1.0 mg/mL to about 10 mg/mL. In one example, a sufficient volume of intravenous formulation can be administered to a patient in a day such that the total dose for the day is between about 10 and about 1500 mg/m$^2$.

Subcutaneous formulations, preferably prepared according to procedures well known in the art at a pH in the range between about 5 and about 12, also include suitable buffers and isotonicity agents, as described below. They can be formulated to deliver a daily dose of HDAC inhibitor in one or more daily subcutaneous administrations, e.g., one, two or three times each day.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

It should be apparent to a person skilled in the art that the various modes of administration, dosages and dosing schedules described herein merely set forth specific embodiments and should not be construed as limiting the broad scope of the invention. Any permutations, variations and combinations of the dosages and dosing schedules are included within the scope of the present invention.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

Pharmaceutical Compositions

The compounds of the invention, and derivatives, fragments, analogs, homologs pharmaceutically acceptable salts or hydrate thereof, can be incorporated into pharmaceutical compositions suitable for oral administration, together with a pharmaceutically acceptable carrier or excipient. Such compositions typically comprise a therapeutically effective amount of any of the compounds above, and a pharmaceutically acceptable carrier. In one embodiment, the effective amount is an amount effective to selectively induce terminal differentiation of suitable neoplastic cells and less than an amount which causes toxicity in a patient.

Any inert excipient that is commonly used as a carrier or diluent may be used in the formulations of the present invention, such as for example, a gum, a starch, a sugar, a, cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

In one embodiment, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to a compound of the instant invention and the inert carrier or diluent, a hard gelatin capsule.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field. Preferred examples of such carriers or diluents include, but are not limited to, water, saline, finger's solutions, dextrose solution, and 5% human serum albumin. Liposomes and non-aqueous vehicles such as fixed oils may also be used., The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included id a container, pack, or dispenser together with instructions for administration.

The compounds of the present invention may be administered intravenously on the first day of treatment, with oral administration on the second day and all consecutive days thereafter.

The compounds of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In the certain embodiments, the amount of the compound that is administered to the patient is less than the amount that causes a concentration of the compound in the patient's plasma to equal or exceed the toxic level of the compound. In one embodiment, the concentration of the compound in the patient's plasma is maintained at about 10 nM. In another embodiment, the concentration of the compound in the patient's plasma is maintained at about 25 nM. In another embodiment, the concentration of the compound in the patient's plasma is maintained at about 50 nM. In another embodiment, the concentration of the compound in the patient's plasma is maintained at about 100 mM. In another embodiment, the concentration of the compound in the patient's plasma is maintained at about 500 nM. In another embodiment, the concentration of the compound in the patient's plasma is maintained at about 1000 nM. In another embodiment, the concentration of the compound in the patient's plasma is maintained at about 2500 nM. In another embodiment, the concentration of the compound in the patient's plasma is maintained at about 5000 nM. The optimal amount of the compound that should be administered to the patient in the practice of the present invention will depend on the particular compound used and the type of cancer being treated.

The instant invention also includes a pharmaceutical composition useful for treating or preventing cancer that comprises a therapeutically effective amount of a compound of Formula I and a second compound selected from: an estrogen receptor modulator, an androgen receptor modulator, a retinoid receptor modulator, a cytotoxic/cytostatic agent, an anti-proliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

In Vitro Methods:

The present invention also provides methods of using the compounds of the present invention for inducing terminal differentiation, cell growth arrest and/or apoptosis of neoplastic cells thereby inhibiting the proliferation of such cells. The methods can be practiced in vivo or in vitro.

In one embodiment, the present invention provides in vitro methods for selectively inducing terminal differentiation, cell growth arrest and/or apoptosis of neoplastic cells, thereby inhibiting proliferation of such cells, by contacting the cells with an effective amount of any one or more of the compounds of the instant invention described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the compounds of the instant invention described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the compounds of the instant invention described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the compounds of the instant invention described herein.

In another embodiment, the invention relates to an in vitro method of inducing terminal differentiation of tumor cells in a tumor comprising contacting the cells with an effective amount of any one or more of the compounds of the instant invention described herein.

In one embodiment, the methods of selectively inducing terminal differentiation, cell growth arrest and/or apoptosis of neoplastic cells, and of inhibiting HDAC will comprise contacting the cells in vivo, i.e., by administering the compounds to a subject harboring neoplastic cells or tumor cells in need of treatment.

Thus, the present invention provides in vivo methods for selectively inducing terminal differentiation, cell growth arrest and/or apoptosis of neoplastic cells in a subject, thereby inhibiting proliferation of such cells in the subject, by administering to the subject an effective amount of any one or more of the compounds of the instant invention described herein.

In a particular embodiment, the present invention relates to a method of selectively inducing terminal differentiation of neoplastic cells and thereby inhibiting proliferation of such cells in a subject. The method comprises administering to the subject an effective amount of one or more of the compounds of the instant invention described herein.

In another embodiment, the invention relates to a method of selectively inducing cell growth arrest of neoplastic cells and thereby inhibiting proliferation of such cells in a subject. The method comprises administering to the subject an effective amount of one or more of the compounds of the instant invention described herein.

In another embodiment, the invention relates to a method of selectively inducing apoptosis of neoplastic cells and thereby inhibiting proliferation of such cells in a subject. The method comprises administering to the subject an effective amount of one or more of the compounds of the instant invention described herein.

In another embodiment, the invention relates to a method of treating a patient having a tumor characterized by proliferation of neoplastic cells. The method comprises administering to the patient one or more of the compounds of the instant invention described herein. The amount of compound is effective to selectively induce terminal differentiation, induce cell growth arrest and/or induce apoptosis of such neoplastic cells and thereby inhibit their proliferation.

The invention is illustrated in the following generic schemes and the examples in the Experimental Details Section that follows. This section is set forth to aid in an understanding of the invention but is not intended to, and should not be construed to limit in any way the invention as set forth in the claims which follow thereafter.

A. Compounds from 4-(1-amino-2-ethoxy-2-oxoethyl)benzoic Acid

Schemes 1 and 1A illustrate the use of 4-(1-amino-2-ethoxy-2-oxoethyl)benzoic acid to generate amides, carbamates and primary amines with an α-carboxy substituent.

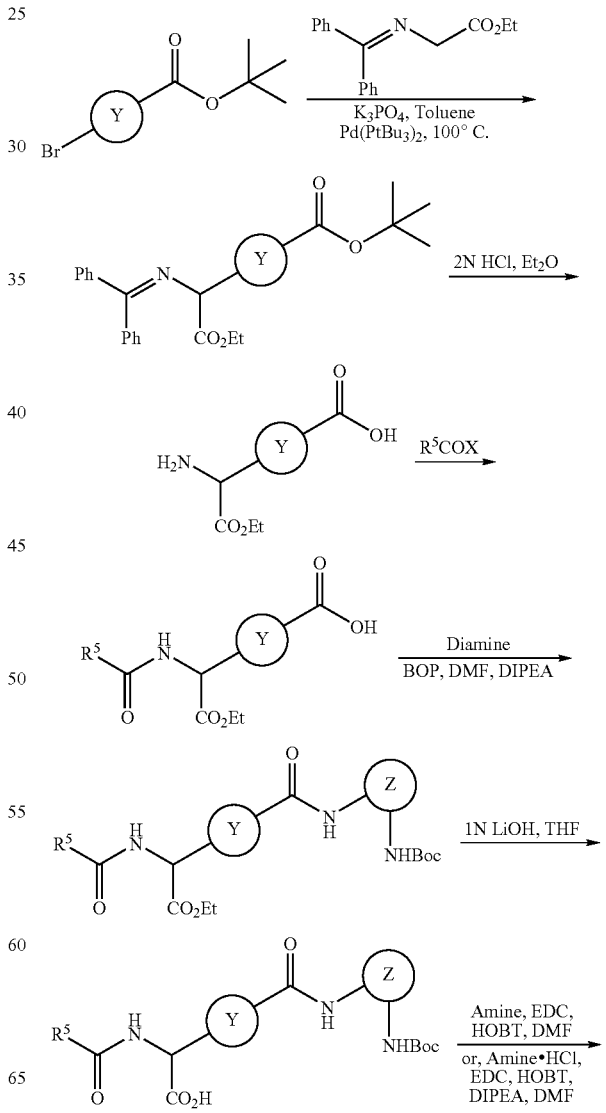

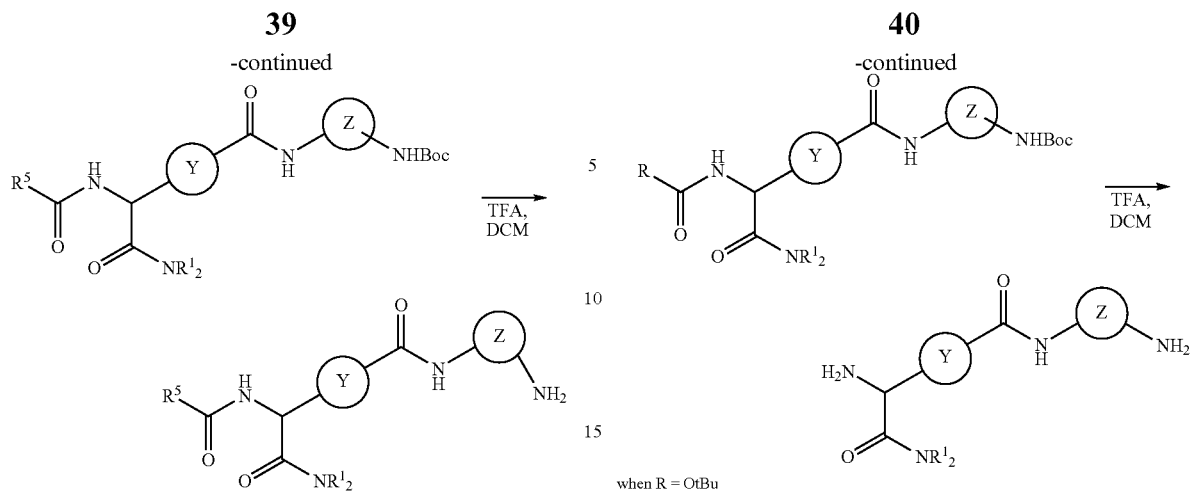
SCHEME 1A
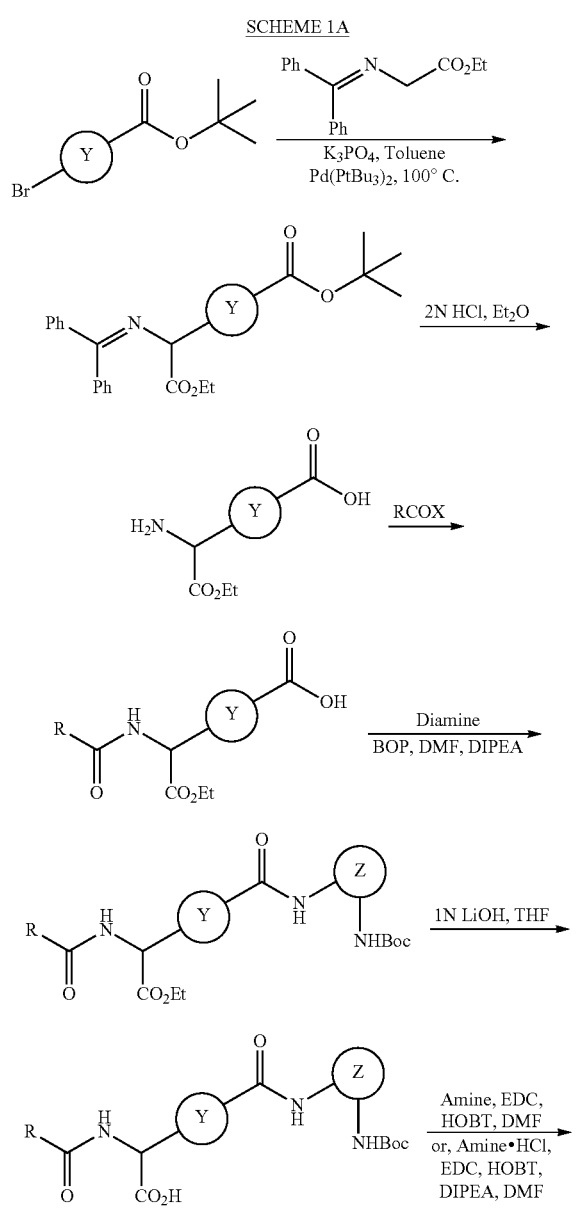
B. Compounds from 4-carboxyphenylboronic Acid
Scheme 2 illustrates the use of 4-carboxyphenylboronic acid to generate amines with an α-carboxy substituent.
SCHEME 2
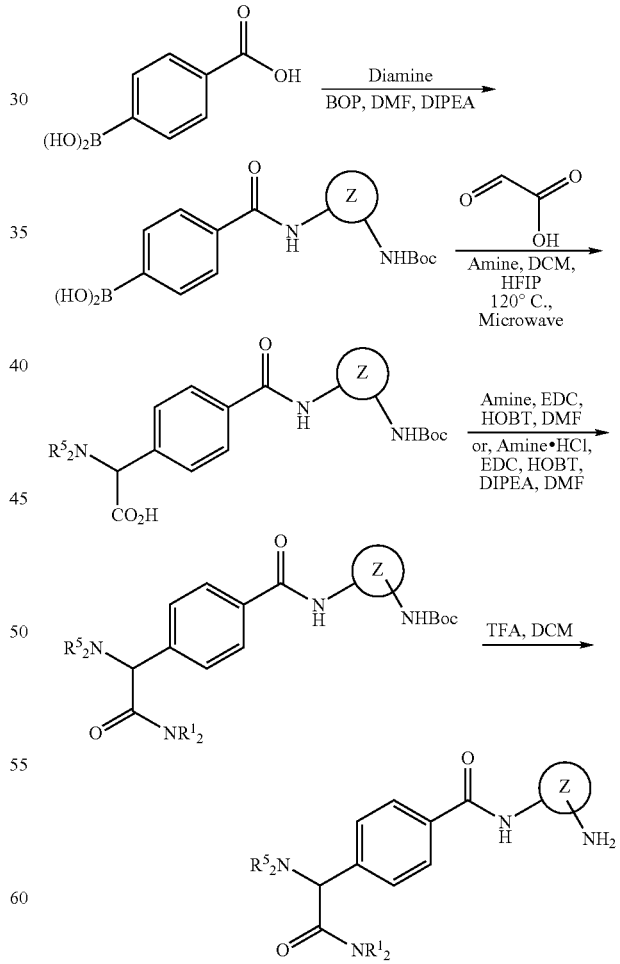
C. Compounds from Aldehydes Using Ugi Chemistry
Scheme 3 illustrates the use of aldehydes to generate amines and amides with an α-carboxy substituent.

SCHEME 3

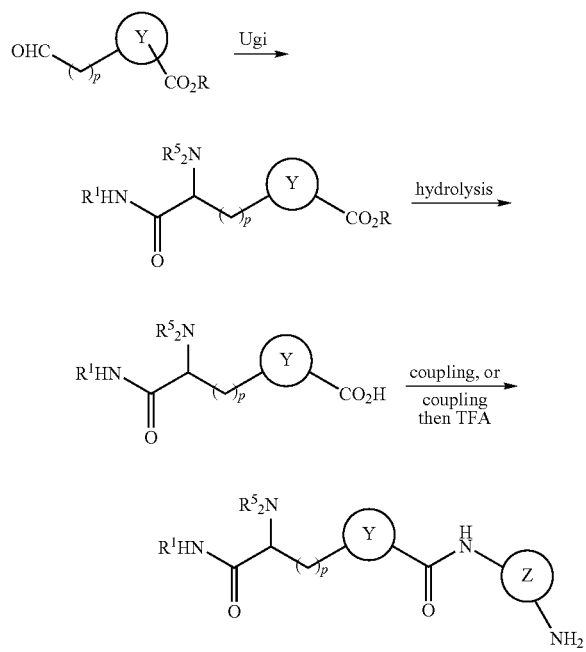

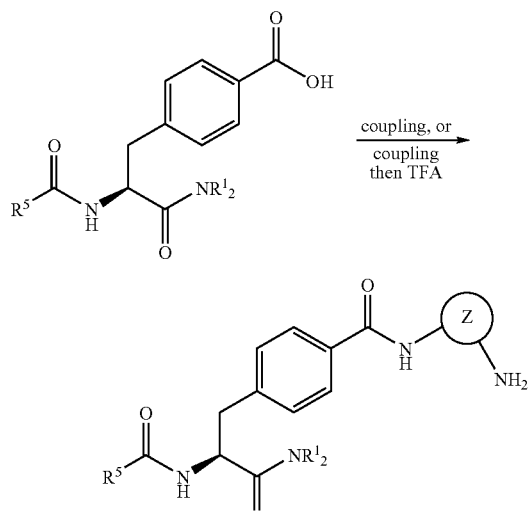

D. Compounds from 4-carboxyphenyl Alanine

Scheme 4 illustrates the use of substituted 4-carboxyphenyl alanine to generate amines, amides and carbamates with an α-carboxy substituent.

SCHEME 4

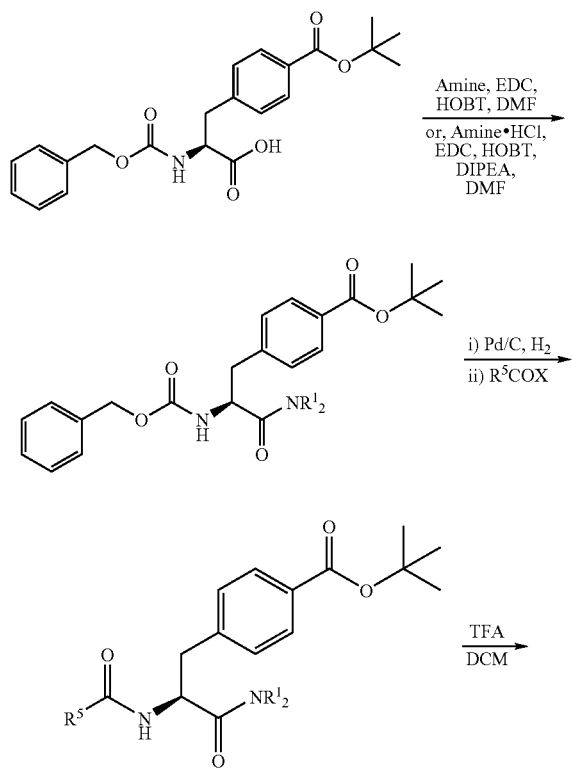

E. Compounds from 4-carboxybenzyl Bromide

Schemes 5 and 5A illustrate the use of substituted 4-carboxybenzyl bromide to generate amines with an α-carboxy substituent.

SCHEME 5

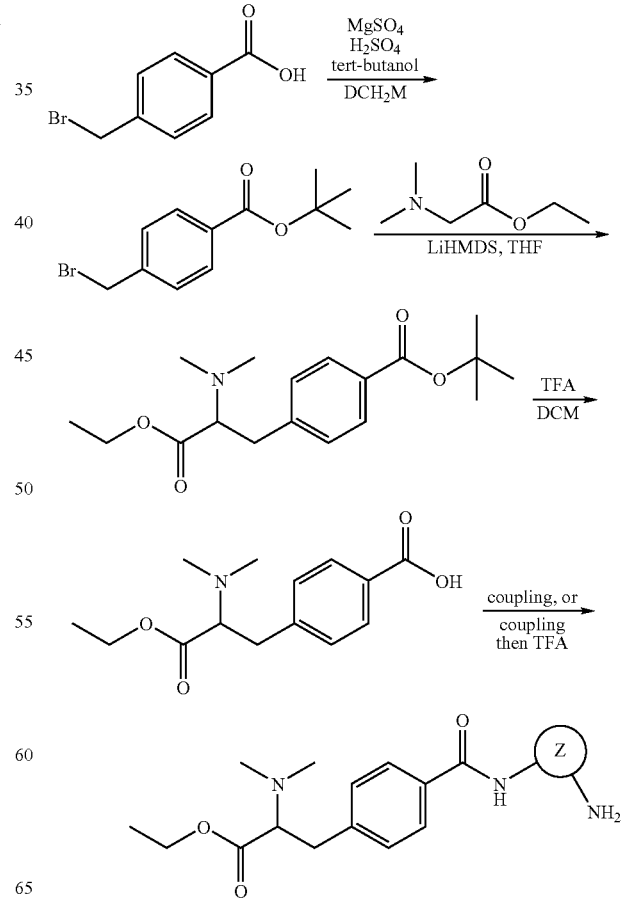

SCHEME 5A
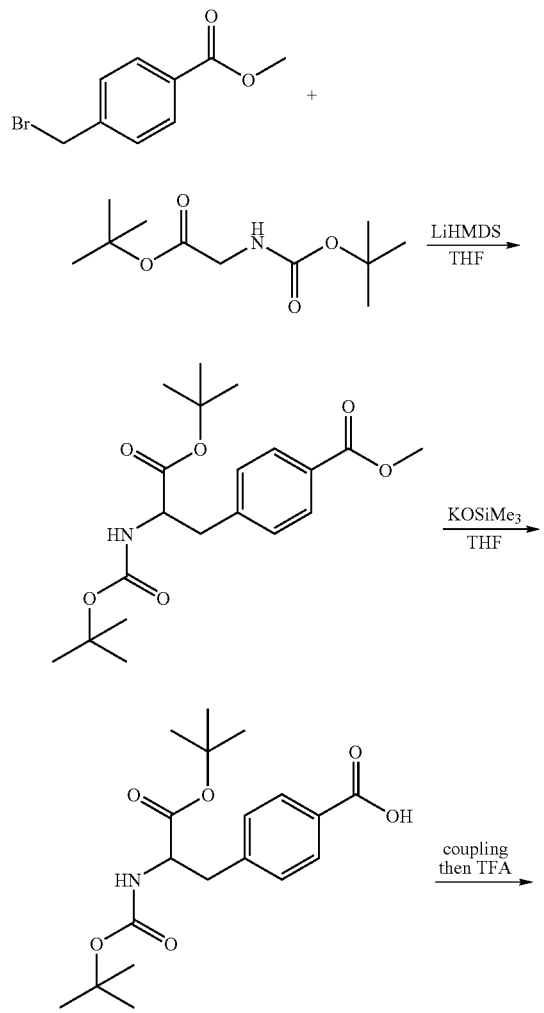
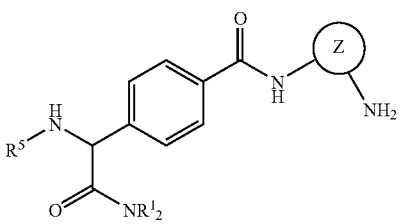
G Compounds from 3-amino-2-phenylpropanoic Acids
Schemes 7-9 illustrate the use of 3-amino-2-phenylpropanoic acids to generate amides.
SCHEME 7
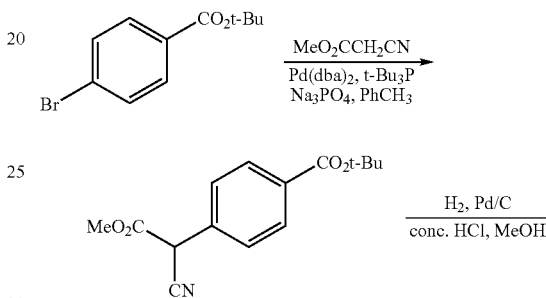
F. Compounds from Phenylglycine Derivatives
Scheme 6 illustrates the use of phenylglycine derivatives to generate amides, sulfonamides, ureas and carbamates with an α-carboxy substituent.
SCHEME 6
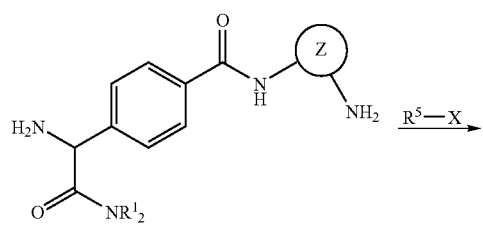
SCHEME 8
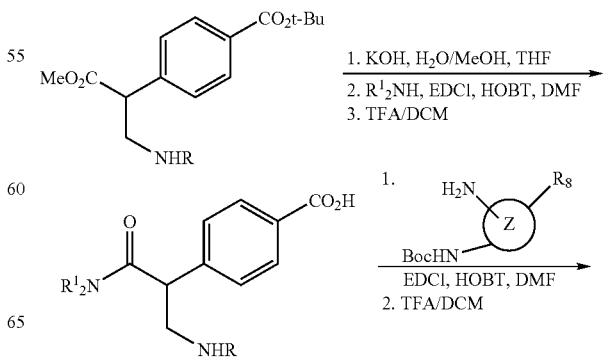
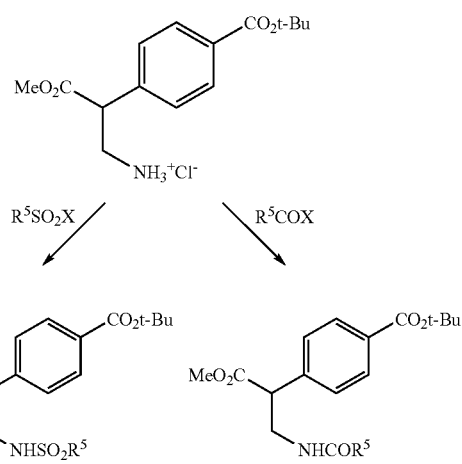

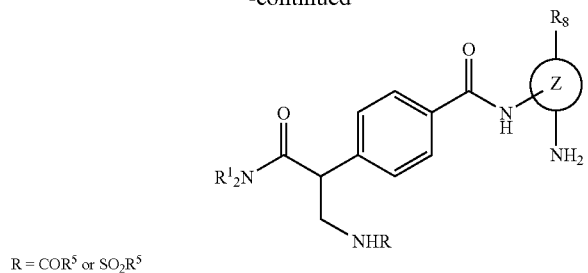
SCHEME 9
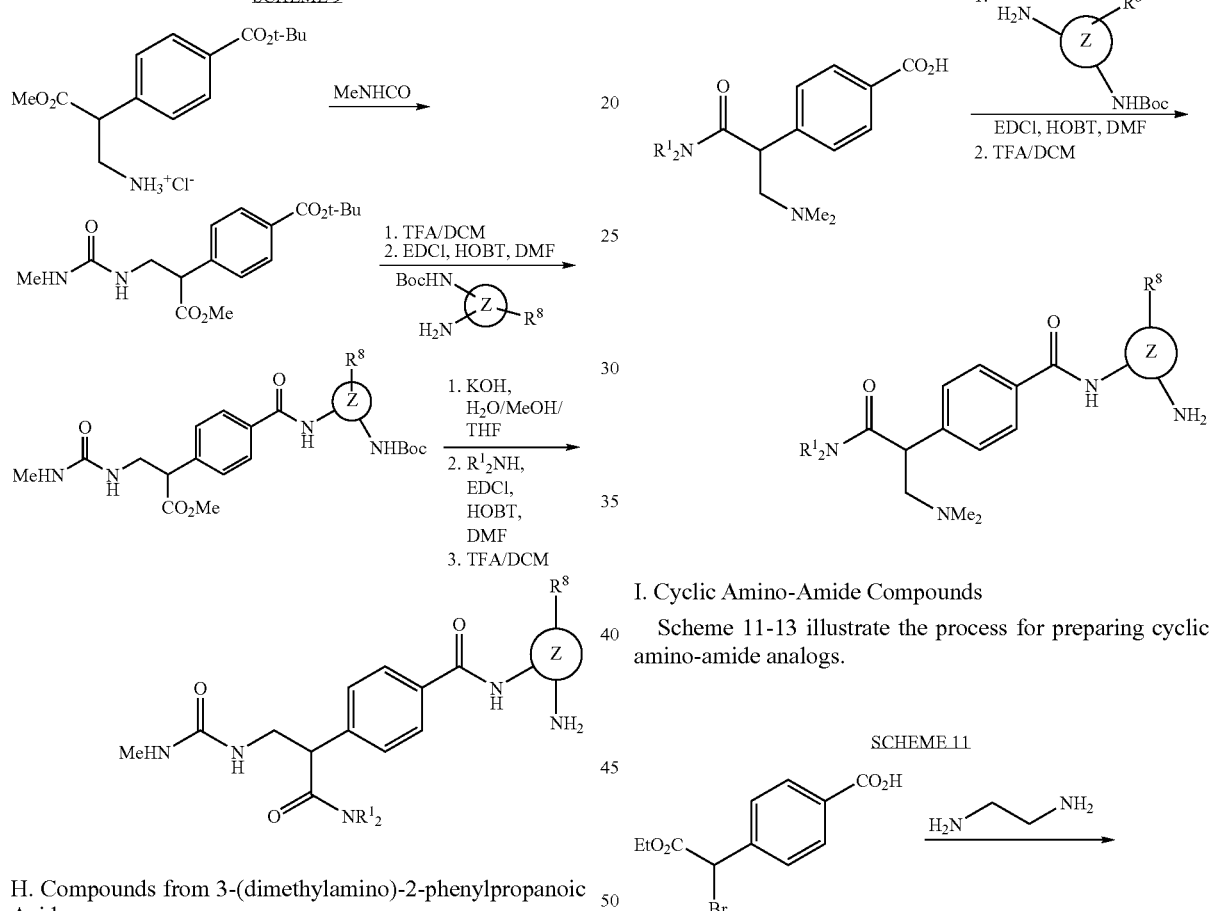
H. Compounds from 3-(dimethylamino)-2-phenylpropanoic Acids
Scheme 10 illustrates the use of 3-(dimethylamino)-2-phenylpropanoic acids to generate amides.
SCHEME 10
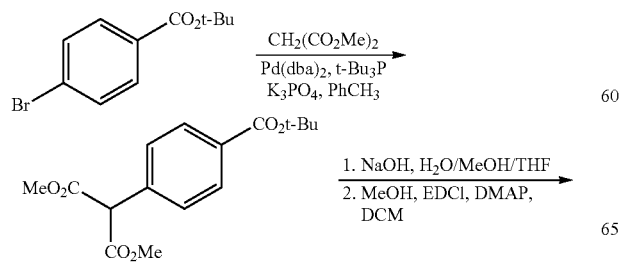
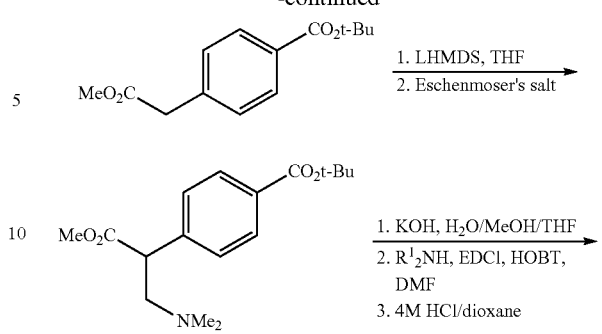
I. Cyclic Amino-Amide Compounds
Scheme 11-13 illustrate the process for preparing cyclic amino-amide analogs.
SCHEME 11
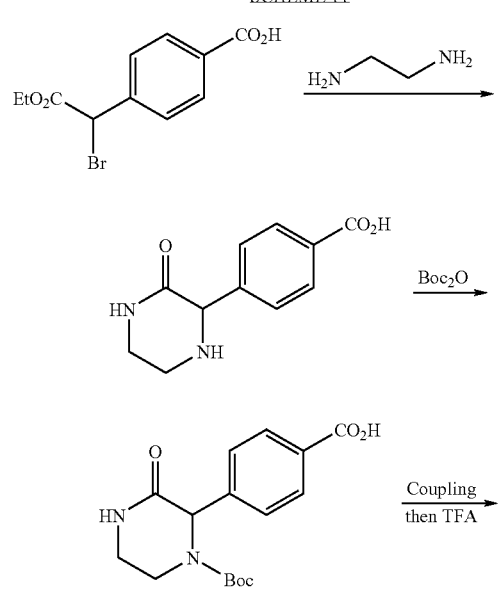

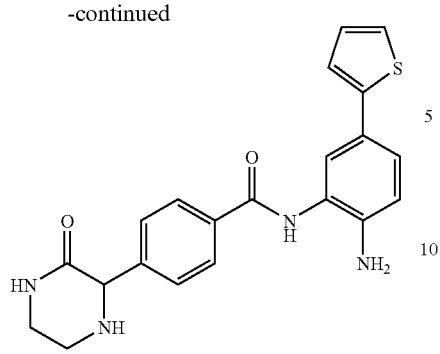

SCHEME 12

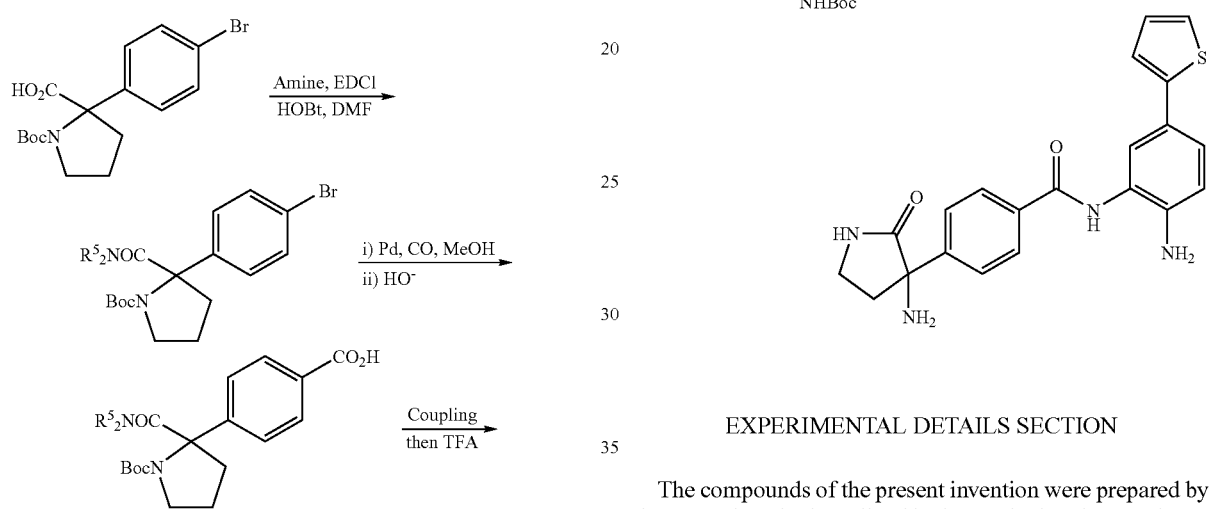

SCHEME 13

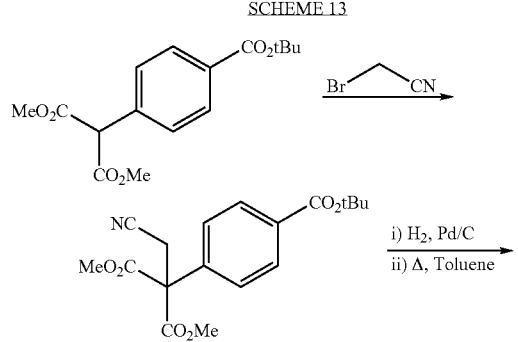

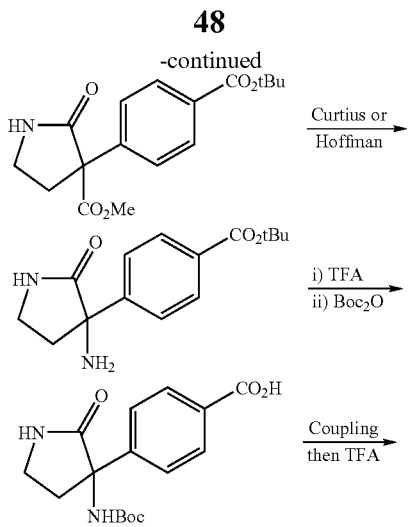

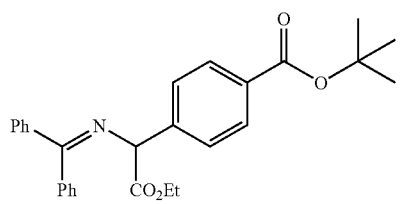

EXPERIMENTAL DETAILS SECTION

The compounds of the present invention were prepared by the general methods outlined in the synthetic schemes above.

Example 1

Step A: Tert-butyl 4-{1-[(diphenylmethylene)amino]-2-ethoxy-2-oxoethyl}benzoate. Tert-butyl 4-bromobenzoate (10.3 g, 40.1 mmol), ethyl N-(diphenylmethylene)glycinate (14.99 g, 56.1 mmol), potassium phosphate (25.5 g, 120 mmol) and bis(tri-t-butylphosphine)palladium(0) (0.409 g, 0.801 mmol) were stirred in toluene (120 mL) at 100° C. under nitrogen for 3 days. Room temperature was attained and the mixture filtered through Celite and concentrated in vacuo. The residue was purified by MPLC to give the desired product as a yellow oil. $^1$H NMR (DMSO-$d_6$, 600 MHz) δ 7.86 (d, J=7.8 Hz, 2H), 7.58 (m, 2H), 7.51 (m, 3H), 7.48 (d, J=7.8 Hz, 2H), 7.45 (m, 1H), 7.41 (t, J=7.5 Hz, 2H), 7.08 (m, 1H), 5.08 (s, 1H), 4.00 (m, 2H), 1.51 (s, 9H), 1.05 (t, J=6.9 Hz, 3H).

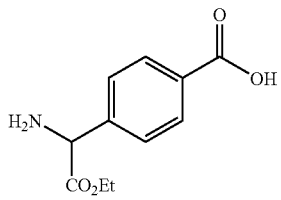

Step B: 4-(1-amino-2-ethoxy-2-oxoethyl)benzoic acid. Tert-butyl 4-{1-[(diphenylmethylene)amino]-2-ethoxy-2-oxoethyl}benzoate (17.4 g, 39.2 mmol) and 2N HCl (200 mL, 400 mmol) were stirred in diethyl ether (200 mL) at room temperature overnight. The aqueous phase was separated and concentrated in vacuo. The HCl salt was dissolved in water and 35 mL of 2N NaOH was added. The volume was reduced in vacuo and the resulting precipitate collected by filtration to give to give the desired product as a white solid. $^1$H NMR (DMSO-$d_6$, 600 MHz) δ 7.88 (d, J=8.1 Hz, 2H), 7.47 (d, J=8.1 Hz, 2H), 4.60 (s, 1H), 4.04 (m, 2H), 1.09 (t, J=7.2 Hz, 3H). MS: cal'd 224 (MH+), exp 224 (MH+).

Example 2

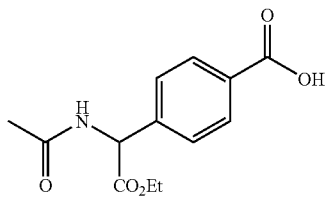

4-[1-(acetylamino)-2-ethoxy-2-oxoethyl]benzoic acid. 4-(1-amino-2-ethoxy-2-oxoethyl)benzoic acid, as described in Example 1, Step B, (0.94 g, 2.79 mmol) and DIPEA (1.509 mL, 8.64 mmol) were suspended in THF (4 mL) and acetic anhydride (0.289 mL, 3.07 mmol) was added. The mixture was stirred at room temperature overnight. 2N HCl was added and the products extracted into EtOAc. The combined organic extracts were washed with brine, dried over MgSO$_4$ and concentrated in vacuo. The residue was purified by prep-HPLC to give the desired product as a white powder. $^1$H NMR (DMSO-$d_6$, 600 MHz) δ 13.00 (br s, 1H), 8.77 (d, J=7.2 Hz, 1H), 7.92 (d, J=8.4 Hz, 2H), 7.47 (d, J=8.4 Hz, 2H), 5.45 (d, J=7.2 Hz, 1H), 4.07 (m, 2H), 1.88 (s, 3H), 1.09 (t, J=7.2 Hz, 3H). MS: cal'd 266 (MH+), exp 266 (MH+).

Example 3

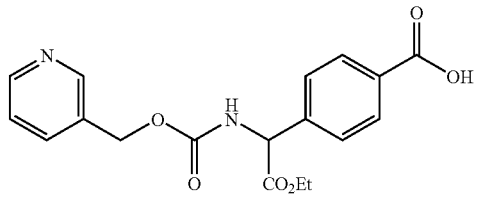

4-(2-ethoxy-2-oxo-1-{[(pyridin-3-ylmethoxy)carbonyl]amino}ethyl)benzoic acid. CDI (312 mg, 1.926 mmol) was suspended in THF (2 mL) and a solution of 3-pyridinemethanol (210 mg, 1.926 mmol) in THF (2 mL) was added. After 40 minutes the resulting solution was added to a suspension of 4-(1-amino-2-ethoxy-2-oxoethyl)benzoic acid, as described in Example 1, Step B, (430 mg, 1.926 mmol), DBU (0.290 mL, 1.926 mmol) and triethylamine (0.268 ml, 1.926 mmol) in THF (8 mL). The mixture was stirred at room temperature for 24 hours. The solvent was removed in vacuo and water was added. The mixture was acidified to pH 5 with 2N HCl and extracted with EtOAc. The organic phase was dried over MgSO$_4$ and concentrated in vacuo. The residue was purified by prep-HPLC to give the TFA salt of the desired product as a colorless gum. $^1$H NMR (DMSO-$d_6$, 600 MHz) δ 8.71 (s, 1H), 8.66 (d, J=5.3 Hz, 1H), 8.44 (d, J=7.9 Hz, 1H), 8.09 (d, J=7.9 Hz, 1H), 7.90 (d, J=8.4 Hz, 2H), 7.68 (dd, J=7.9 and 5.3 Hz, 1H), 7.50 (d, J=8.4 Hz, 2H), 5.33 (d, J=7.9 Hz, 1H), 5.15 (AB q, J=13.2 Hz, 2H), 4.07 (m, 2H), 1.08 (t, J=7.0 Hz, 3H). MS: cal'd 359 (MH+), exp 359 (MH+).

Example 4

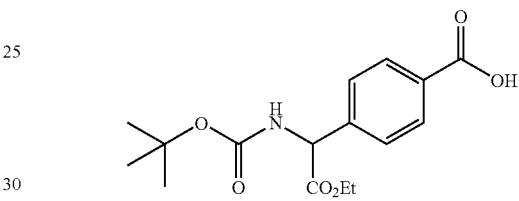

Step A: 4-{1-[(tert-butoxycarbonyl)amino]-2-ethoxy-2-oxoethyl}benzoic acid. 4-(1-amino-2-ethoxy-2-oxoethyl)benzoic acid, as described in Example 1, Step B, (0.8 g, 3.58 mmol) and DIPEA (1.377 mmol, 7.88 mmol) were suspended in THF (8 mL) and BOC$_2$O (0.915 mL, 3.94 mmol) was added. The solution was stirred at room temperature for 2 days. The reaction mixture was diluted with EtOAc, washed with 2N HCl and brine, dried over MgSO$_4$ and concentrated in vacuo to give the desired product as a colorless gum. $^1$H NMR (DMSO-$d_6$, 600 MHz) δ 12.95 (br s, 1H), 7.88 (d, J=8.4 Hz, 2H), 7.84 (d, J=8.4 Hz, 1H), 7.48 (d, J=8.4 Hz, 2H), 5.25 (d, J=8.4 Hz, 1H), 4.06 (m, 2H), 1.36 (s, 9H), 1.09 (t, J=7.2 Hz, 3H). MS: cal'd 324 (MH+), exp 224 (MH+).

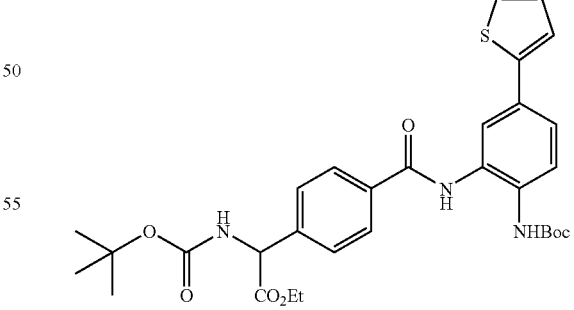

Step B: Ethyl [(tert-butoxycarbonyl)amino][4-({2-[(tert-butoxycarbonyl)amino]-5-(2-thienyl)phenyl]amino}carbonyl)phenyl]acetate. 4-{1-[(tert-butoxycarbonyl)amino]-2-ethoxy-2-oxoethyl}benzoic acid (1.2 g, 3.71 mmol), tert-butyl [2-amino-4-(2-thienyl)phenyl]carbamate (1.293 g, 4.45 mmol), BOP (2.462 g, 5.57 mmol) and DIPEA (0.972 mL, 5.57 mmol) were stirred in DMF (10 ml) at room temperature for 3 days. Saturated NaHCO$_3$ was added and the products extracted into EtOAc. The combined organic extracts were washed with brine, dried over MgSO$_4$ and concentrated in vacuo. The residue was purified by prep-HPLC to give the desired product as a pale yellow powder. $^1$H NMR (DMSO-d$_6$, 600 MHz) δ 9.89 (s, 1H), 8.71 (br s, 1H), 7.93 (d, J=8.4 Hz, 2H), 7.87 (d, J=8.4 Hz, 1H), 7.83 (d, J=1.8 Hz, 1H), 7.60 (d, J=8.4 Hz, 1H), 7.54 (d, J=8.4 Hz, 2H), 7.50 (m, 2H), 7.42 (d, J=3.6 Hz, 1H), 7.10 (dd, J=5.4 and 3.6 Hz, 1H), 5.27 (d, J=8.4 Hz, 1H), 4.08 (m, 2H), 1.43 (s, 9H), 1.38 (s, 9H), 1.11 (t, J=7.2 Hz, 3H). MS: cal'd 596 (MH+), exp 440, 484, 496 (MH+).

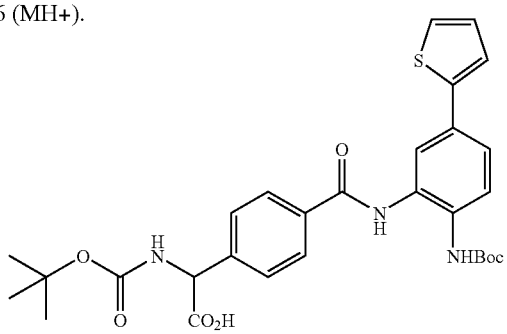

Step C: [(Tert-butoxycarbonyl)amino][4-({[2-[(tert-butoxycarbonyl)amino]-5-(2-thienyl)phenyl]amino}carbonyl)phenyl]acetic acid. Ethyl [(tert-butoxycarbonyl)amino][4-({[2-[(tert-butoxycarbonyl)amino]-5-(2-thienyl)phenyl]amino}carbonyl)phenyl]acetate (1.08 g, 1.813 mmol) and 1N lithium hydroxide (3.99 mL, 3.99 mmol) were stirred in THF (16 mL) at room temperature for 2 days. The reaction was diluted with water, 2 mL of 2N HCl was added and the products extracted into EtOAc. The combined organic extracts were washed with brine, dried over MgSO$_4$ and concentrated in vacuo to give the desired product as a pale yellow powder. $^1$H NMR (DMSO-d$_6$, 600 MHz) δ 12.90 (br s, 1H), 9.90 (s, 1H), 8.72 (s, 1H), 7.94 (d, J=8.4 Hz, 2H), 7.81 (d, J=1.2 Hz, 1H), 7.72 (d, J=8.4 Hz, 1H), 7.62 (d, J=8.4 Hz, 1H), 7.57 (d, J=8.4 Hz, 2H), 7.51 (m, 2H), 7.44 (d, J=3.6 Hz, 1H), 7.12 (dd, J=5.1 and 3.6 Hz, 1H), 5.23 (d, J=8.4 Hz, 1H), 1.45 (s, 9H), 1.39 (s, 9H). MS: cal'd 568 (MH+), exp 412, 456, 468 (MH+).

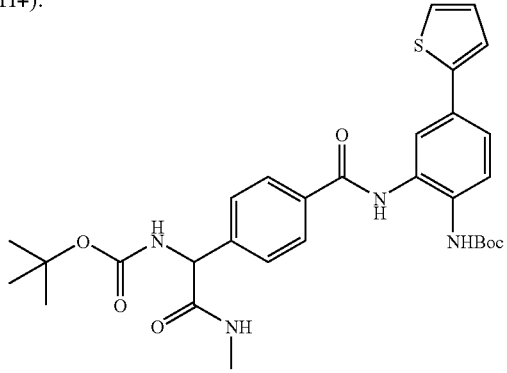

Step D: Tert-butyl [2-({4-[1-[(tert-butoxycarbonyl)amino]-2-(methylamino)-2-oxoethyl]-benzoyl}amino)-4-(2-thienyl)phenyl]carbamate. [(Tert-butoxycarbonyl)amino][4-({[2-[(tert-butoxycarbonyl)amino]-5-(2-thienyl)phenyl]amino}carbonyl)phenyl]acetic acid (100 mg, 0.176 mmol), methylamine hydrochloride (23.79 mg, 0.352 mmol), HOBT (35.7 mg, 0.264 mmol), DIPEA (0.092 mL, 0.528 mmol) and EDC (50.7 mg, 0.264 mmol) were stirred in DMF (1 mL) at room temperature for 3 days. The reaction mixture was purified directly by prep-HPLC to give the desired product as a white solid. $^1$H NMR (DMSO-d$_6$, 600 MHz) δ 9.86 (s, 1H), 8.69 (s, 1H), 8.14 (q, J=4.2 Hz, 1H), 7.90 (d, J=8.4 Hz, 2H), 7.79 (d, J=1.8 Hz, 1H), 7.60 (d, J=8.4 Hz, 1H), 7.51 (d, J=8.4 Hz, 2H), 7.49 (m, 2H), 7.42 (dd, J=3.6 and 1.2 Hz, 1H), 7.38 (d, J=7.8 Hz, 1H), 7.10 (dd, J=4.8 and 3.6 Hz, 1H), 5.19 (d, J=8.4 Hz, 1H), 2.55 (d, J=4.2 Hz, 3H), 1.43 (s, 9H), 1.36 (s, 9H). MS: cal'd 581 (MH+), exp 425, 469 (MH+).

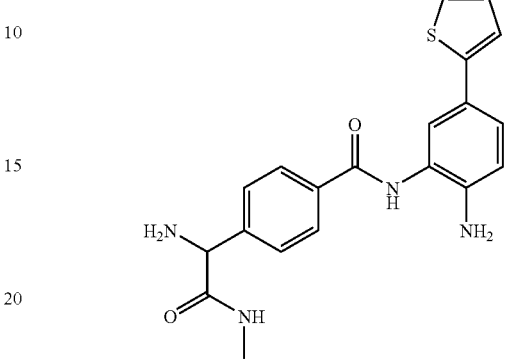

Step E: 4-[1-amino-2-(methylamino)-2-oxoethyl]-N-[2-amino-5-(2-thienyl)phenyl]-benzamide. Tert-butyl [2-({4-[1-[(tert-butoxycarbonyl)amino]-2-(methylamino)-2-oxoethyl]benzoyl}amino)-4-(2-thienyl)phenyl]carbamate (70 mg, 0.121 mmol) was stirred in DCM (1 mL)/TFA (0.5 mL) at room temperature for 1 hour. The solvent was removed in vacuo and the residue triturated in Et$_2$O to give the TFA salt of the desired product as a blue-green solid. $^1$H NMR (DMSO-d$_6$, 600 MHz) δ 9.83 (s, 1H), 8.72 (br s, 3H), 8.50 (q, J=4.2 Hz, 1H), 8.04 (d, J=8.4 Hz, 2H), 7.61 (d, J=8.4 Hz, 2H), 7.47 (d, J=1.2 Hz, 1H), 7.35 (d, J=4.8 Hz, 1H), 7.32 (dd, J=8.1 and 2.1 Hz, 1H), 7.24 (d, J=3.6 Hz, 1H), 7.03 (dd, J=4.8 and 3.6 Hz, 1H), 6.84 (d, J=8.4 Hz, 1H), 4.97 (br s, 1H), 2.61 (d, J=4.2 Hz, 3H). MS: cal'd 381 (MH+), exp 381 (MH+).

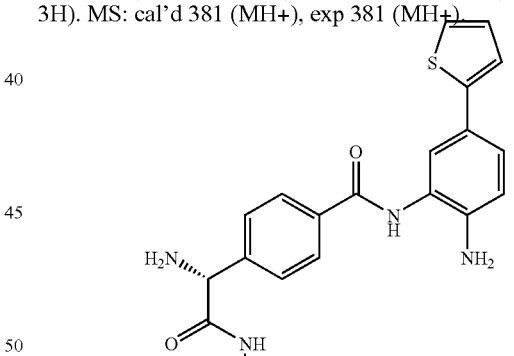

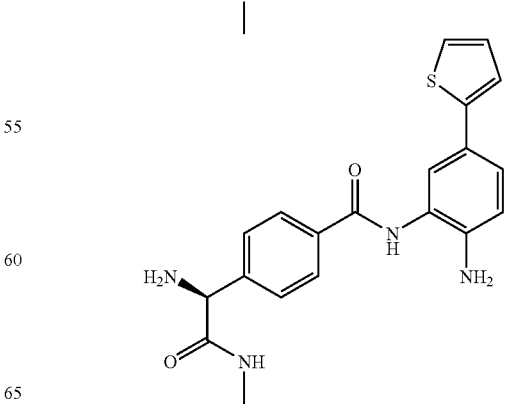

Step F: 4-[(1R)-1-amino-2-(methylamino)-2-oxoethyl]-N-[2-amino-5-(2-thienyl)phenyl]benzamide and 4-[(1S)-1-amino-2-(methylamino)-2-oxoethyl]-N-[2-amino-5-(2-thienyl)phenyl]benzamide. 4-[1-amino-2-(methylamino)-2-oxoethyl]-N-[2-amino-5-(2-thienyl)phenyl]benzamide was separated into its enantiomers by chiral HPLC: Chiralpak AD column 250×20 mm, mobile phase heptane/IPA 65/35, flow rate 12 mL/min. Peak 1 retention time 24.7 mins; MS: cal'd 381 (MH+), exp 381 (MH+). Peak 2 retention time 28.5 mins; MS: cal'd 381 (MH+), exp 381 (MH+).

Additional analogs were prepared in procedures similar to those described Examples 1-4 above.

| Cpd # | Structure | Name | MS | Salt forms |
|---|---|---|---|---|
| 4-1 | | amino[4-({[2-amino-5-(2-thienyl)phenyl]amino}-carbonyl)phenyl]acetic acid | cal'd 368 (MH$^+$), exp 368 (MH$^+$) | TFA |
| 4-2 | | ethyl amino[4-({[2-amino-5-(2-thienyl)phenyl]amino} carbonyl)phenyl]acetate | cal'd 396 (MH$^+$), exp 396 (MH$^+$) | Free base |
| 4-3 | | 4-[1-amino-2-(methylamino)-2-oxoethyl]-N-[2-amino-5-(2-thienyl)phenyl]benzamide | cal'd 381 (MH$^+$), exp 381 (MH$^+$) | Free base, TFA, HCl |

-continued

| Cpd # | Name | MS | Salt forms |
|---|---|---|---|
| 4-4 | N-[2-amino-5-(2-thienyl)phenyl]-4-(1,2-diamino-2-oxoethyl)benzamide | cal'd 367 (MH+), exp 367 (MH+) | Free base, TFA |
| 4-5 | 4-{1-amino-2-oxo-2-[(2,2,2-trifluoroethyl)amino]-ethyl}-N-[2-amino-5-(2-thienyl)phenyl]benzamide | cal'd 449 (MH+), exp 449 (MH+) | Free base |
| 4-5 | 4-{1-amino-2-[(2-methoxyphenyl)amino]-2-oxoethyl}-N-(4-amino-1-phenyl-1H-pyrazol-3-yl)benzamide | cal'd 457 (MH+), exp 457 (MH+) | HCl |
| 4-6 | 4-[1-amino-2-(isoxazol-3-ylamino)-2-oxoethyl]-N-(4-amino-1-phenyl-1H-pyrazol-3-yl)benzamide | cal'd 418 (MH+), exp 418 (MH+) | HCl |

-continued

| Cpd # | Name | MS | Salt forms |
|---|---|---|---|
| 4-7 | 4-[1-amino-2-oxo-2-(pyridin-2-ylamino)ethyl]-N-(4-amino-1-phenyl-1H-pyrazol-3-yl)benzamide | cal'd 428 (MH$^+$), exp 428 (MH$^+$) | HCl |
| 4-8 | 4-{1-amino-2-[(4-methyl-1,3-thiazol-2-yl)amino]-2-oxoethyl}-N-(4-amino-1-phenyl-1H-pyrazol-3-yl)benzamide | cal'd 448 (MH$^+$), exp 448 (MH$^+$) | HCl |
| 4-9 | 4-{1-amino-2-[(3-methoxyphenyl)amino]-2-oxoethyl}-N-(4-amino-1-phenyl-1H-pyrazol-3-yl)benzamide | cal'd 457 (MH$^+$), exp 457 (MH$^+$) | HCl |
| 4-10 | 4-{1-amino-2-[(4-cyanopyridin-2-yl)amino]-2-oxoethyl}-N-(4-amino-1-phenyl-1H-pyrazol-3-yl)benzamide | cal'd 453 (MH$^+$), exp 453 (MH$^+$) | HCl |

-continued

| Cpd # | | Name | MS | Salt forms |
|---|---|---|---|---|
| 4-11 | 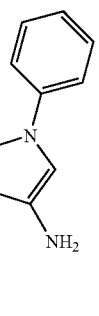 | 4-[1-amino-2-(2,3-dihydro-1,4-benzodioxin-6-ylamino)-2-oxoethyl]-N-(4-amino-1-phenyl-1H-pyrazol-3-yl)benzamide | cal'd 485 (MH+), exp 485 (MH+) | HCl |
| 4-12 | 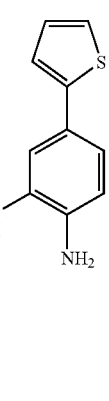 | ethyl [4-({[2-amino-5-(2-thienyl)phenyl]amino}-carbonyl)phenyl]{[(pyridin-3-ylmethoxy)carbonyl]-amino}acetate | cal'd 531 (MH+), exp 531 (MH+) | Free base |
| 4-13 | 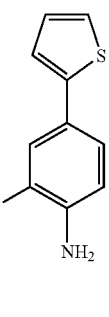 | [4-({[2-amino-5-(2-thienyl)phenyl]amino}-carbonyl)phenyl]{[(pyridin-3-ylmethoxy)carbonyl]-amino}acetic acid | cal'd 503 (MH+), exp 503 (MH+) | TFA |
| 4-14 | 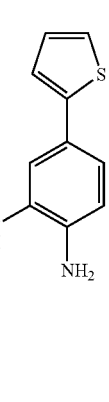 | pyridin-3-ylmethyl [1-[4-({[2-amino-5-(2-thienyl)phenyl]amino}-carbonyl)phenyl]-2-(methylamino)-2-oxoethyl]carbamate | cal'd 516 (MH+), exp 516 (MH+) | Free base, TFA |

| Cpd # | Name | MS | Salt forms |
|---|---|---|---|
| 4-15 | pyridin-3-ylmethyl {2-amino-1-[4-({[2-amino-5-(2-thienyl)phenyl]amino}carbonyl)phenyl]-2-oxoethyl}carbamate | cal'd 502 (MH+), exp 502 (MH+) | Free base |
| 4-16 | pyridin-3-ylmethyl [1-[4-({[2-amino-5-(2-thienyl)phenyl]amino}-carbonyl)phenyl]-2-(ethylamino)-2-oxoethyl]carbamate | cal'd 530 (MH+), exp 530 (MH+) | Free base |
| 4-17 | pyridin-3-ylmethyl [1-[4-({[2-amino-5-(2-thienyl)phenyl]amino}-carbonyl)phenyl]-2-(isopropylamino)-2-oxoethyl]carbamate | cal'd 544 (MH+), exp 544 (MH+) | Free base |
| 4-17 | pyridin-3-ylmethyl [1-[4-({[2-amino-5-(2-thienyl)phenyl]amino}-carbonyl)phenyl]-2-(dimethylamino)-2-oxoethyl]carbamate | cal'd 530 (MH+), exp 530 (MH+) | Free base |

| Cpd # | Name | MS | Salt forms |
|---|---|---|---|
| 4-18 | (acetylamino)[4-({[2-amino-5-(2-thienyl)phenyl]amino}carbonyl)phenyl]acetic acid | cal'd 410 (MH$^+$), exp 410 (MH$^+$) | TFA |
| 4-19 | 4-[1-(acetylamino)-2-oxo-2-pyrrolidin-1-ylethyl]-N-[2-amino-5-(2-thienyl)phenyl]benzamide | cal'd 463 (MH$^+$), exp 463 (MH$^+$) | TFA |
| 4-20 | 4-[1-(acetylamino)-2-amino-2-oxoethyl]-N-[2-amino-5-(2-thienyl)phenyl]benzamide | cal'd 409 (MH$^+$), exp 409 (MH$^+$) | TFA |
| 4-21 | 4-[1-(acetylamino)-2-(methylamino)-2-oxoethyl]-N-[2-amino-5-(2-thienyl)phenyl]-benzamide | cal'd 423 (MH$^+$), exp 423 (MH$^+$) | TFA, Free base |

-continued

| Cpd # | Name | MS | Salt forms |
|---|---|---|---|
| 4-22 | 4-[1-(acetylamino)-2-(dimethylamino)-2-oxoethyl]-N-[2-amino-5-(2-thienyl)phenyl]-benzamide | cal'd 437 (MH+), exp 437 (MH+) | TFA |
| 4-23 | 4-[1-(acetylamino)-2-(isopropylamino)-2-oxoethyl]-N-[2-amino-5-(2-thienyl)phenyl]-benzamide | cal'd 451 (MH+), exp 451 (MH+) | TFA |
| 4-24 | 4-[1-(acetylamino)-2-(ethylamino)-2-oxoethyl]-N-[2-amino-5-(2-thienyl)phenyl]-benzamide | cal'd 437 (MH+), exp 437 (MH+) | TFA |
| 4-25 | Tert-butyl [2-({4-[1-(acetylamino)-2-(methylamino)-2-oxoethyl]benzoyl}-amino)-4-(2-thienyl)phenyl] carbamate | cal'd 523 (MH+), exp 423 (MH+) | Free base |

Example 5

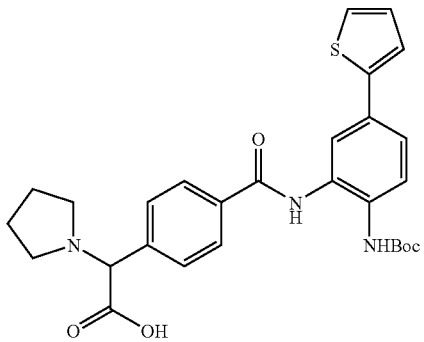

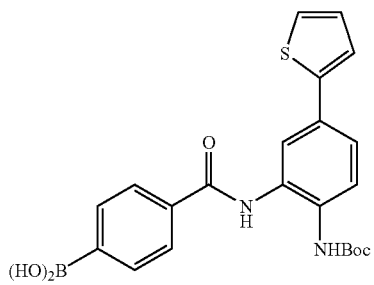

Step A: [4-({[2-[(tert-butoxycarbonyl)amino]-5-(2-thienyl)phenyl]amino}carbonyl)-phenyl]boronic acid. Prepared from 4-carboxyphenylboronic acid via the procedure described in Example 4, Step B. MS: cal'd 439 (MH+), exp 339, 383 (MH+).

Step B: [4-({[2-[(tert-butoxycarbonyl)amino]-5-(2-thienyl)phenyl]amino}carbonyl)phenyl](pyrrolidin-1-yl)acetic acid. Glyoxilic acid monohydrate (0.042 g, 0.456 mmol) was suspended in DCM (2.1 mL)/HFIP (0.2 mL) and pyrrolidine (0.038 mL, 0.456 mmol) and [4-({[2-[(tert-butoxycarbonyl)amino]-5-(2-thienyl)phenyl]amino}carbonyl)phenyl]boronic acid (0.2 g, 0.456 mmol) were added. The reaction was stirred at room temperature overnight. The mixture was transferred to a microwave vial and heated to 120° C. for 30 minutes in the microwave. The solvent was removed in vacuo and the residue triturated in methanol to give the desired product as a pale yellow powder. $^1$H NMR (DMSO-$d_6$, 600 MHz) δ 9.95 (s, 1H), 8.74 (br s, 1H), 7.95 (d, J=8.4 Hz, 2H), 7.79 (d, J=1.8 Hz, 1H), 7.60 (d, J=8.4 Hz, 2H), 7.49 (m, 2H), 7.43 (d, J=2.4 HZ, 1H), 7.11 (dd, J=5.4 and 3.6 Hz, 1H), 4.33 (s, 1H), 3.06 (m, 2H), 2.79 (m, 2H), 1.84 (m, 4H), 1.43 (s, 9H). MS: cal'd 522 (MH+), exp 522 (MH+).

The following compounds were made using the techniques described above and in Example 4.

| Cpd# | | Name | MS |
|---|---|---|---|
| 5-2 | | N-[2-amino-5-(2-thienyl)phenyl]-4-[2-(methylamino)-2-oxo-1-pyrrolidin-1-ylethyl]benzamide (isolated as free base) | cal'd 435 (MH$^+$), exp 435 (MH$^+$) |
| 5-3 | | [4-({[2-amino-5-(2-thienyl)phenyl]amino}carbonyl)phenyl]-(pyrrolidin-1-yl)acetic acid (isolated as TFA salt) | cal'd 422 (MH$^+$), exp 422 (MH$^+$) |

Example 6

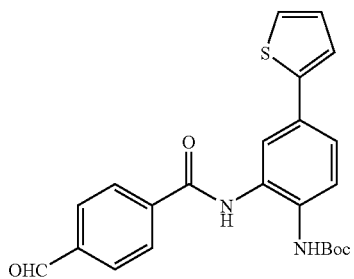

Step A: Tert-butyl [2-[(4-formylbenzoyl)amino]-4-(2-thienyl)phenyl]carbamate. Methyl 4-[({2-[(tert-butoxycarbonyl)amino]-5-thien-2-ylphenyl}amino)carbonyl]benzoate (1.7 g, 3.76 mmol) was made 0.1 M in anhydrous THF and cooled to 0° C. To this stirring suspension was added LiBH$_4$ (0.55 g, 25.20 mmol), 2M in anhydrous THF. The resulting solution was slowly warmed to ambient temperature stirred for 14 hours. The reaction was then cooled to 0° C. and carefully quenched with saturated aqueous NH$_4$Cl. The mixture was diluted with water and extracted with ethyl acetate two times. The combined organic layers were washed with brine then dried over anhydrous magnesium sulfate and concentrated in vacuo. The residue was diluted with DCM and purified by MPLC to give tert-butyl 2-{[4-(hydroxymethyl)benzoyl]amino}-4-thien-2-ylphenylcarbamate.

The product from above (0.52 g, 1.23 mmol) was made 0.15 M in DCM and to this stirring solution was added Dess-Martin Periodinate (0.52 g, 1.23 mmol). The reaction mixture was stirred at ambient temperature for 1 hour then quenched with aqueous sodium-thiosulfate. After stirring for 15 minutes the mixture was partitioned between EtOAc and saturated aqueous sodium bicarbonate. The organic layer was washed again with saturated aqueous sodium bicarbonate, then with brine, dried over anhydrous magnesium sulfate and concentrated in vacuo. The residue was purified by MPLC to give the desired product. $^1$H NMR (DMSO-d$_6$, 600 MHz) δ10.10 (s, 1H), 10.06 (s, 1H), 8.77 (s, 1H), 8.15 (d, J=8.2 Hz, 2H), 8.05 (d, J=8.2 Hz, 2H), 7.79 (d, J=1.8 Hz, 1H), 7.63 (d, J=8.5 Hz, 1H), 7.51 (m, 2H), 7.44 (m, 1H), 7.11 (m, 1H), 1.43 (s, 9H).

6-1

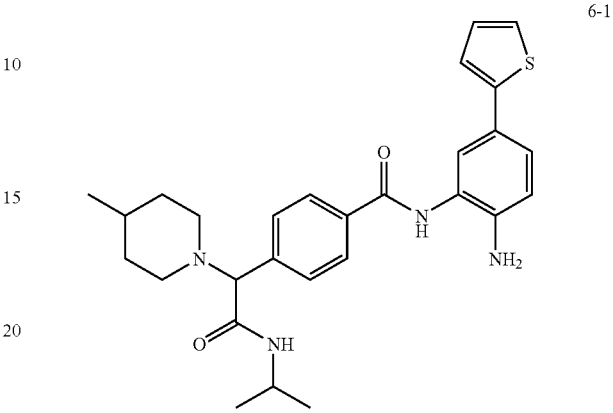

Step B: N-[2-amino-5-(2-thienyl)phenyl]-4-[2-(isopropylamino)-1-(4-methylpiperidin-1-yl)-2-oxoethyl]benzamide. Tert-butyl 2-[(4-formylbenzoyl)amino]-4-thien-2-ylphenylcarbamate (20.0 mg, 0.047 mmol) was made 2.0 M in anhydrous trifluoroethanol and to this stirring solution was added N-methylpiperazine (4.7 mg, 0.047 mmol), 2-isocyanopropane (4.9 mg, 0.071 mmol), and acetic acid (2.8 mg, 0.047 mmol). The resulting mixture was stirred at ambient temperature for 14 hours. The reaction mixture was diluted with TFA and stirred at ambient temperature for 30 minutes. The reaction mixture was then purified by reverse phase chromatography to yield the desired product as the TFA salt. MS: cal'd 491 (MH+), exp 491 (MH+).

Additional analogs were prepared in procedures similar to those described in the above example. The following compounds were isolated as TFA salts.

| Cpd# | | Name | MS |
|---|---|---|---|
| 6-2 | | N-(2-amino-5-thien-2-ylphenyl)-4-{1-azetidin-1-yl-2-[(4-methylphenyl)amino]-2-oxoethyl}benzamide | cal'd 497 (MH+), exp 497 (MH+) |

-continued

| Cpd# | Name | MS |
|---|---|---|
| 6-3 | N-(2-amino-5-thien-2-ylphenyl)-4-[1-(diethylamino)-2-(isopropylamino)-2-oxoethyl]benzamide | cal'd 465 (MH$^+$), exp 465 (MH$^+$) |
| 6-4 | N-(2-amino-5-thien-2-ylphenyl)-4-[1-azetidin-1-yl-2-(isopropylamino)-2-oxoethyl]benzamide | cal'd 449 (MH$^+$), exp 449 (MH$^+$) |

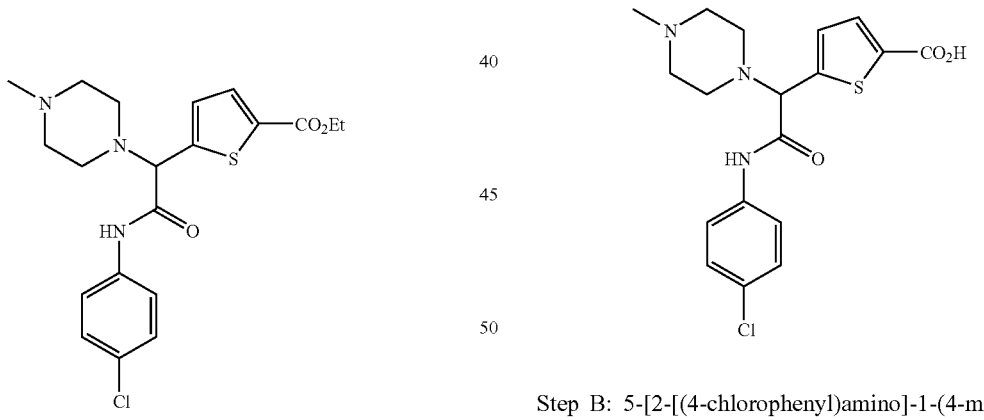

Example 7

Step A: Ethyl 5-[2-[(4-chlorophenyl)amino]-1-(4-methylpiperazin-1-yl)-2-oxoethyl]thiophene-2-carboxylate.
Ethyl 5-formylthiophene-2-carboxylate (0.50 g, 2.71 mmol) was made 2.25 M in anhydrous trifluoroethanol and to this stirring solution was added N-methylpiperazine (0.33 g, 3.26 mmol), 1-chloro-4-isocyanobenzene (0.45 g, 3.26 mmol) and acetic acid (0.20 g, 3.26 mmol). The resulting mixture was stirred at ambient temperature overnight. The reaction mixture was concentrated in vacuo then purified by MPLC to give the desired product. MS: cal'd 422, 424 (MH+), exp 422, 424 (MH+).

Step B: 5-[2-[(4-chlorophenyl)amino]-1-(4-methylpiperazin-1-yl)-2-oxoethyl]thiophene-2-carboxylic acid. Ethyl 5-[2-[(4-chlorophenyl)amino]-1-(4-methylpiperazin-1-yl)-2-oxoethyl]thiophene-2-carboxylate (0.56 g, 1.33 mmol) was made 0.5 M in dioxane and to this stirring solution was added 3 equivalents 3M LiOH (1.33 mL, 3.98 mmol). The resulting mixture was stirred at ambient temperature for 3 hours. The mixture was adjusted to pH 6 with 1 M HCl then concentrated in vacuo to give the desired product. MS: cal'd 394, 396 (MH+), exp 394, 396 (MH+).

Additional analogs were prepared in procedures similar to those described above and in Example 4. The following compounds were prepared as the free base (parent) form.

| Cpd # | | Name | MS |
|---|---|---|---|
| 7-1 | | N-(2-amino-5-thien-3-ylphenyl)-5-[2-[(4-chlorophenyl)amino]-1-(4-methylpiperazin-1-yl)-2-oxoethyl]thiophene-2-carboxamide | cal'd 566, 568 (MH+), exp 566, 568 (MH+) |
| 7-2 | | N-(2-amino-5-thien-2-ylphenyl)-5-[2-[(4-chlorophenyl)amino]-1-(4-methylpiperazin-1-yl)-2-oxoethyl]thiophene-2-carboxamide | cal'd 566, 568 (MH+), exp 566, 568 (MH+) |

Example 8

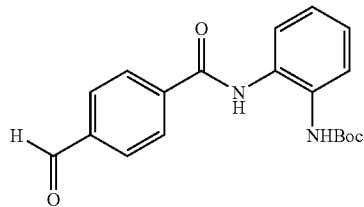

Step A: tert-butyl {2-[(4-formylbenzoyl)amino]phenyl}carbamate. 4-Formylbenzoic acid (1.50 g, 10.0 mmol), tert-butyl (2-aminophenyl)carbamate (2.08 g, 10.0 mmol), EDC (1.92 g, 10.0 nmol) and HOBt (1.35 g, 10.0 mmol) were dissolved in DMF and the solution was heated at 70° C. for 4 h. The solution was diluted with 200 mL of EtOAc and the organic solution was washed twice with 150 mL of water, then sequentially with 150 mL each of 1 N HCl, NaHCO₃ (sat'd), and brine. The solution was dried over MgSO₄, concentrated, then purified by flash chromatography (12-100% ethyl acetate in hexanes) to give the desired product, MS cal'd 341 (MH+), exp 341 (MH+).

Step B: N-(2-aminophenyl)-4-{1-(benzoylamino)-2-[(4-methoxyphenyl)amino]-2-oxoethyl}benzamide. The compound from Step A above (50 mg, 0.147 mmol), 2,4-dimethoxybenzylamine (26.5 mL, 0.176 mmol), 4-methoxyphenylisocyanide (19.6 mg, 0.147 mmol), and benzoic acid (17.9 mg, 0.147 mmol) were dissolved in 50 µL of trifluoroethanol (TFE) and heated at 50° C. for 3 h. The solution was purified by flash chromatography (12-100% EtOAc in hexanes) to give tert-butyl {2-[(4-{1-(benzoylamino)-2-[(4-methoxyphenyl)amino]-2-oxoethyl}benzoyl)amino]phenyl}carbamate, which was dissolved in 1 mL of CH₂Cl₂ and 1 mL of TFA was added. The solution was allowed to stir for 1 h, the solvents were evaporated and the residue was triturated twice with 5 mL of Et₂O to give the desired product as a yellow powder. $^1$H NMR (600 MHz, CD₃OD) δ 8.06 (d, J=8.2 Hz, 2H), 7.89 (d, J=7.3 Hz, 2H), 7.76 (d, J=8.5 Hz, 2H), 7.56 (t, J=7.4 Hz, 1H), 7.44-7.49 (m, 4H), 7.31-7.38 (m, 4H), 6.87 (d, J=7.1 Hz, 2H), 5.91 (s, 1H), 3.75 (s, 3H), MS cal'd 495 (MH+), exp 495 (MH+).

Additional analogs were prepared in procedures similar to those described for the preparations of the above examples. Unless otherwise indicated, the following compounds were isolated as TFA salts.

| Cpd # | Name | MS |
|---|---|---|
| 8-1 | N-(2-aminophenyl)-4-[1-(benzoylamino)-2-(benzylamino)-2-oxoethyl]benzamide | cal'd 479 (MH+), exp 479 (MH+) |
| 8-2 | N-(2-aminophenyl)-4-[1,2-bis(benzylamino)-2-oxoethyl]benzamide | cal'd 493 (MH+), exp 493 (MH+) |
| 8-3 | N-(2-aminophenyl)-4-{2-(benzylamino)-2-oxo-1-[(2-phenylethyl)amino]ethyl benzamide | cal'd 507 (MH+), exp 507 (MH+) |
| 8-4 | N-(2-aminophenyl)-4-{1-(benzoylamino)-2-[(4-chlorophenyl)amino]-2-oxoethyl}benzamide | cal'd 499 (MH+), exp 499 (MH+) |

| Cpd # | | Name | MS |
|---|---|---|---|
| 8-5 | 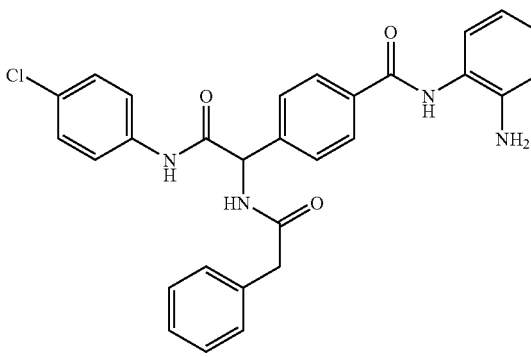 | N-(2-aminophenyl)-4-{2-[(4-chlorophenyl)amino]-2-oxo-1-[(phenylacetyl)amino]ethyl}benzamide | cal'd 513 (MH$^+$), exp 513 (MH$^+$) |
| 8-6 | 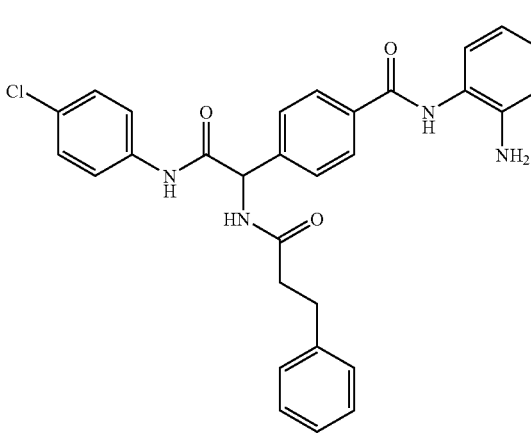 | N-(2-aminophenyl)-4-{2-[(4-chlorophenyl)amino]-2-oxo-1-[(3-phenylpropanoyl)amino]ethyl}benzamide (isolated as the free base and TFA salt) | cal'd 527 (MH$^+$), exp 527 (MH$^+$) |
| 8-7 | 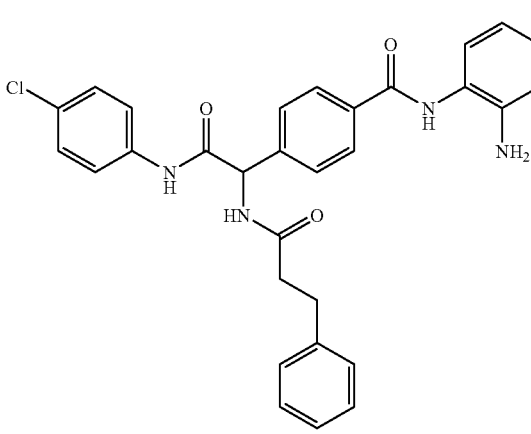 | N-(2-aminophenyl)-4-{1-(benzoylamino)-2-[(4-methylphenyl)amino]-2-oxoethyl}benzamide | cal'd 479 (MH$^+$), exp 479 (MH$^+$) |
| 8-8 | 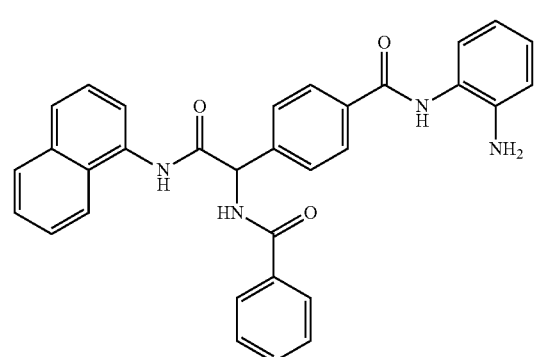 | N-(2-aminophenyl)-4-[1-(benzoylamino)-2-(2-naphthylamino)-2-oxoethyl]benzamide | cal'd 515 (MH$^+$), exp 515 (MH$^+$) |

| Cpd # | | Name | MS |
|---|---|---|---|
| 8-9 | 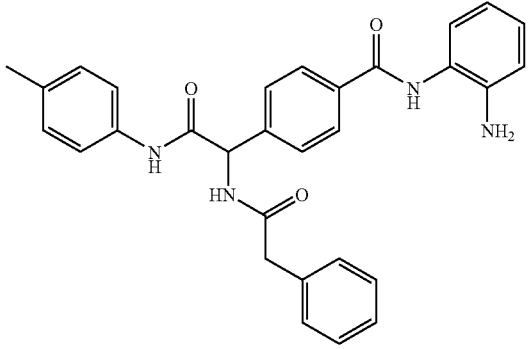 | N-(2-aminophenyl)-4-{2-[(4-methylphenyl)amino]-2-oxo-1-[(phenylacetyl)amino]ethyl}benzamide | cal'd 493 (MH+), exp 493 (MH+) |
| 8-10 | 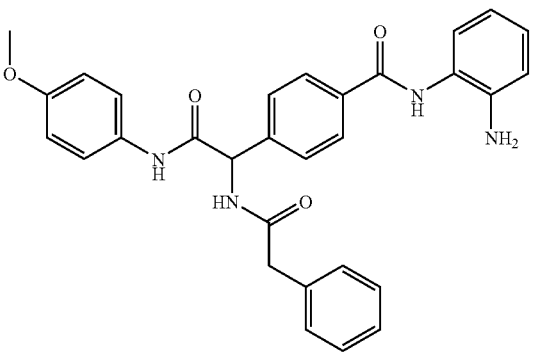 | N-(2-aminophenyl)-4-{2-[(4-methoxyphenyl)amino]-2-oxo-1-[(phenylacetyl)amino]ethyl}benzamide | cal'd 509 (MH+), exp 509 (MH+) |
| 8-11 | 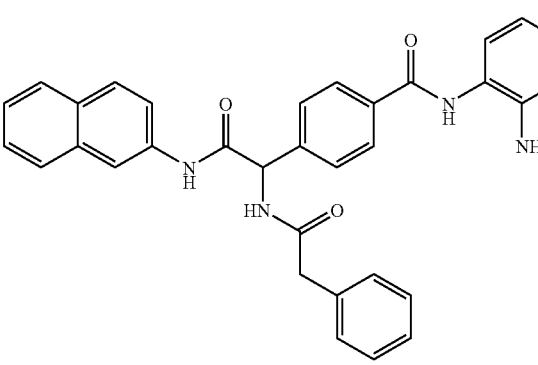 | N-(2-aminophenyl)-4-{2-(2-naphthylamino)-2-oxo-1-[(phenylacetyl)amino]-ethyl}benzamide | cal'd 529 (MH+), exp 529 (MH+) |
| 8-12 | 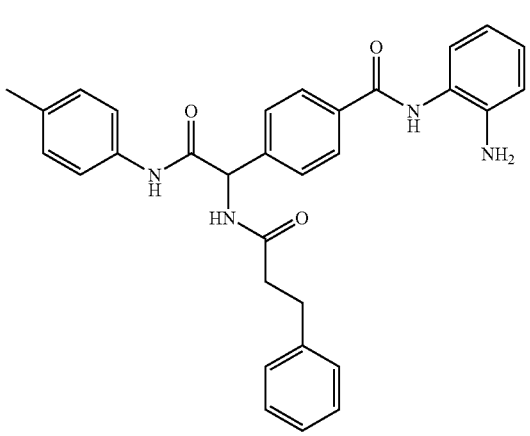 | N-(2-aminophenyl)-4-{2-[(4-methylphenyl)amino]-2-oxo-1-[(3-phenylpropanoyl)amino]ethyl}benzamide | cal'd 507 (MH+), exp 507 (MH+) |

| Cpd # | | Name | MS |
|---|---|---|---|
| 8-13 | | N-(2-aminophenyl)-4-{2-[(4-methoxyphenyl)amino]-2-oxo-1-[(3-phenylpropanoyl)amino]ethyl}benzamide | cal'd 523 (MH+), exp 523 (MH+) |
| 8-14 | | N-(2-aminophenyl)-4-{2-(2-naphthylamino)-2-oxo-1-[(3-phenylpropanoyl)amino]ethyl}benzamide | cal'd 543 (MH+), exp 543 (MH+) |

Example 9

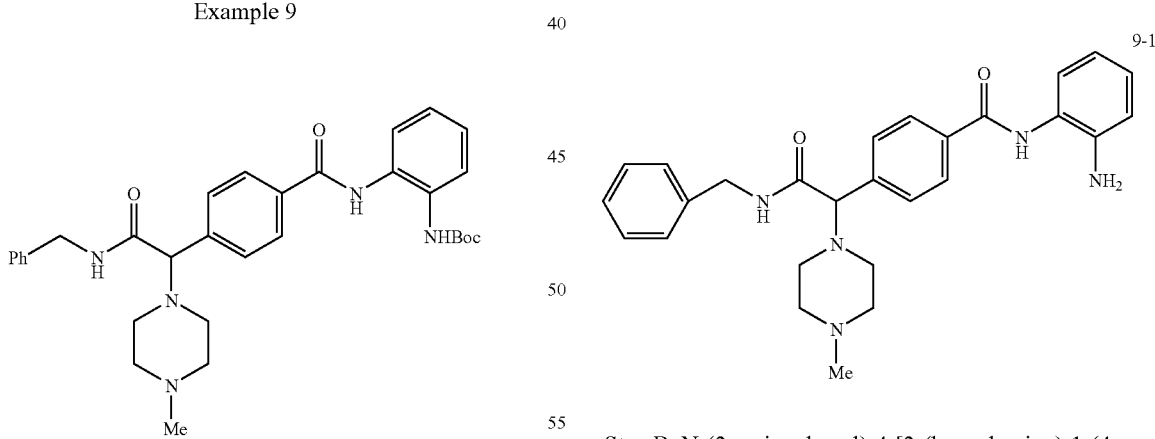

Step A: Tert-butyl [2-({4-[2-(benzylamino)-1-(4-methylpiperazin-1-yl)-2-oxoethyl]benzoyl}-amino)phenyl]carbamate. The compound described in Example 8, Step A, (50 mg, 0.147 mmol), acetic acid (10.1 µL, 0.176 mmol), N-methylpiperizine (19.5 µL, 0.176 mmol), and benzyl isocyanide (19.1 µL, 0.176 mmol) were dissolved in 100 µL of TFE. The solution was allowed to stir for 18 h at room temperature then purified by reverse phase HPLC to give the desired product. MS cal'd 558 (MH+), exp 558 (MH+).

Step B: N-(2-aminophenyl)-4-[2-(benzylamino)-1-(4-methylpiperazin-1-yl)-2-oxoethyl]-benzamide. The compound from Step C above was dissolved in 1 mL of CH₂Cl₂ then 1 mL of TFA was added. The solution was allowed to stir for 2 h at room temperature, the solvent was evaporated and the solid residue was triturated 2×10 mL Et₂O to give the desired product. MS cal'd 458 (MH+), exp 458 (MH+).

Additional analogs were prepared in procedures similar to those described for the preparations of the above examples. The following compounds were isolated as TFA salts.

| Cpd # | | Name | MS |
|---|---|---|---|
| 9-2 | | N-(2-aminophenyl)-4-[2-[(4-chlorophenyl)amino]-1-(4-ethylpiperazin-1-yl)-2-oxoethyl]benzamide | cal'd 492 (MH+), exp 492 (MH+) |
| 9-3 | | N-(2-aminophenyl)-4-[2-[(4-chlorophenyl)amino]-1-(4-methylpiperazin-1-yl)-2-oxoethyl]benzamide | cal'd 478 (MH+), exp 478 (MH+) |
| 9-4 | | N-(2-aminophenyl)-4-[1-(4-methylpiperazin-1-yl)-2-(2-naphthylamino)-2-oxoethyl]benzamide | cal'd 494 (MH+), exp 494 (MH+) |
| 9-5 | | N-(2-aminophenyl)-4-{2-[(4-chlorophenyl)amino]-1-[(3S)-3-methylpiperazin-1-yl]-2-oxoethyl}benzamide | cal'd 478 (MH+), exp 478 (MH+) |

| Cpd # | | Name | MS |
|---|---|---|---|
| 9-6 | 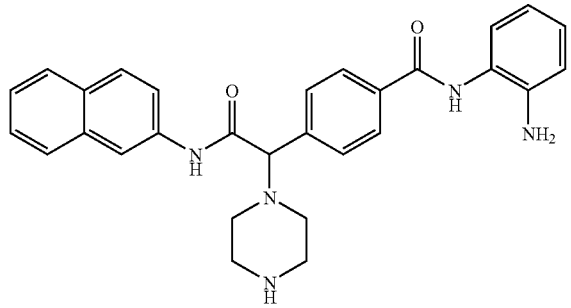 | N-(2-aminophenyl)-4-[2-(2-naphthylamino)-2-oxo-1-piperazin-1-ylethyl]benzamide | cal'd 480 (MH$^+$), exp 480 (MH$^+$) |
| 9-7 | 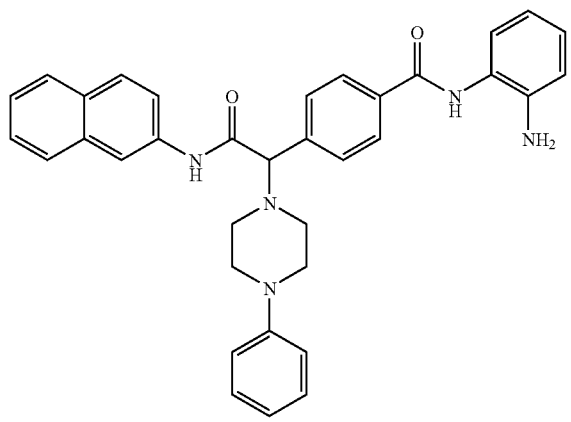 | N-(2-aminophenyl)-4-[2-(2-naphthylamino)-2-oxo-1-(4-phenylpiperazin-1-yl)ethyl]benzamide | cal'd 556 (MH$^+$), exp 556 (MH$^+$) |
| 9-8 | 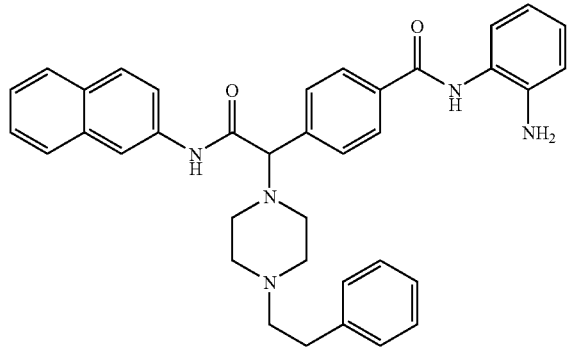 | N-(2-aminophenyl)-4-{2-(2-naphthylamino)-2-oxo-1-[4-(2-phenylethyl)piperazin-1-yl]ethyl}benzamide | cal'd 583 (MH$^+$), exp 583 (MH$^+$) |
| 9-9 | 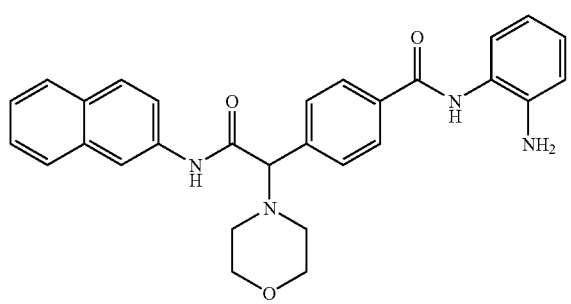 | N-(2-aminophenyl)-4-[1-morpholin-4-yl-2-(2-naphthylamino)-2-oxoethyl]benzamide | cal'd 481 (MH$^+$), exp 481 (MH$^+$) |

Example 9A

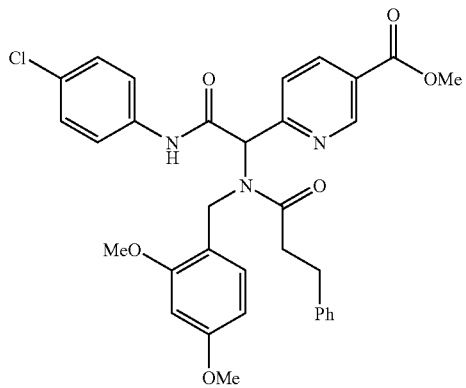

Step A: Methyl 6-{2-[(4-chlorophenyl)amino]-1-[(2,4-dimethoxybenzyl)(3-phenylpropanoyl)-amino]-2-oxoethyl}nicotinate Dihydrocinnamic acid (46 mg, 0.30 mmol), 4-chlorophenylisocyanide (42 mg, 0.30 mmol) and 2,4-dimethoxybenzylamine (61 mg, 0.36 mmol) were added to a solution of methyl 6-formylnicotinate (see Langlois, Y. et al, *Tetrahedron.* 1975, 31, 419-22) (50 mg, 0.30 mmol) in 400 μL of TFE. The solution was allowed to stir for 4 h at room temperature and then purified by flash chromatography (12-100% ethyl acetate in hexanes to give the desired product. MS cal'd 602 (MH+), exp 602 (MH+).

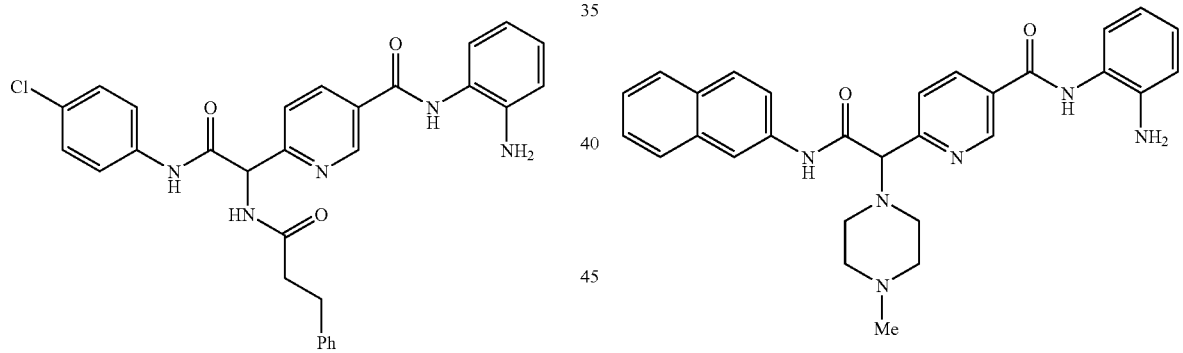

Step B: N-(2-aminophenyl)-6-{2-[(4-chlorophenyl)amino]-2-oxo-1-[(3-phenylpropanoyl)-amino]ethyl}nicotinamide. The compound from Step A above (83.3 mg, 0.138 mmol) was dissolved in 0.5 mL each of THF, methanol and water then 12.0 mg (0.5 mmol) of lithium hydroxide was added and the solution was heated at 50° C. for 4 h. The solution was allowed to cool to room temperature and 300 μL of 2 N HCl was added. The solvent was evaporated and the residue was dissolved in 300 μL of DMF. N-Boc-phenylenediamine (62.5 mg, 0.300 mmol), EDC (58.0 mg, 0.300 mmol), and HOBt (40.5 mg, 0.300 mmol) were added and the solution was allowed to stir for 18 h. The solution was diluted with 50 mL of CH$_2$Cl$_2$ and washed with 50 mL each of NaHCO$_3$ and brine. The solution was concentrated and the residue was dissolved in 1 mL of CH$_2$Cl$_2$ then 1 mL of TFA was added. The solution was heated at 40° C. for 4 h, then concentrated and purified by reverse phase HPLC to give the desired product. MS cal'd 528 (MH+), exp 528 (MH+).

Example 10

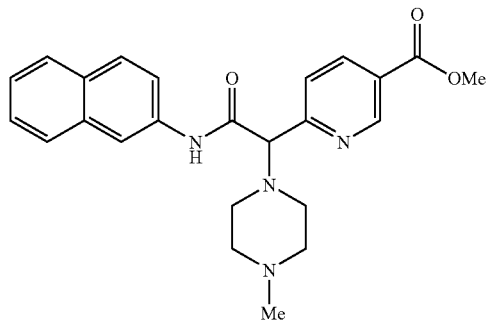

Step A: Methyl-6-[1-(4-methylpiperazin-1-yl)-2-(2-naphthylamino)-2-oxoethyl]nicotinate. Methyl 6-formylnicotinate (50.0 mg, 0.303 mmol), acetic acid (19.0 μL, 0.333 mmol), N-methylpiperizine (40.4 μL, 0.364 mmol), and 2-napthylisocyanide (51.0 mg, 0.333 mmol) were dissolved in 100 μL of TFE. The solution was allowed to stir for 2 h then purified by reverse phase HPLC to give the desired product MS cal'd 419 (MH+), exp 419 (MH+).

Step B: N-(2-aminophenyl)-6-[1-(4-methylpiperazin-1-yl)-2-(2-naphthylamino)-2-oxoethyl]nicotinamide. The compound from Step A above was dissolved in 0.5 mL each of THF, methanol and water then 12.0 mg (0.5 mmol) of lithium hydroxide was added and the solution was stirred for 18 h at rt. The solution was allowed to cool to room temperature and 300 μL of 2 N HCl was added. The solvent was evaporated and the residue was dissolved in 500 μL of DMF. Phenylenediamine (104 mg, 0.500 mmol), EDC (96.7 mg, 0.500 mmol), and HOBt (67.2 mg, 0.500 mmol) were added and the solution was allowed to stir for 18 h. The solution was diluted with 50 mL of CH$_2$Cl$_2$ and washed with 50 mL each of NaHCO$_3$ and brine. The solution was concentrated and purified by reverse phase HPLC to give the desired product. MS cal'd 495 (MH+), exp 495 (MH+).

Example 11

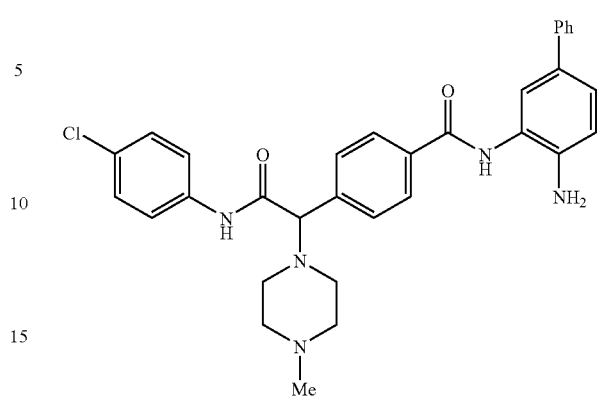

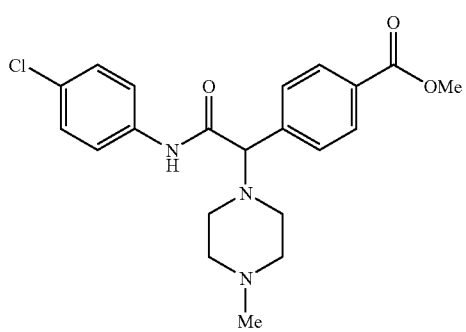

Step A: Methyl 4-[2-[(4-chlorophenyl)amino]-1-(4-methylpiperazin-1-yl)-2-oxoethyl]-benzoate Methyl 4-formylbenzoate (75.0 mg, 0.457 mmol), acetic acid (31.3 μL, 0.548 mmol), N-methylpiperizine (60.8 μL, 0.648 mmol), and 4-chlorophenylisocyanide (75.4 mg, 0.548 mmol) were dissolved in 200 μL of TFE. The solution was allowed to stir for 2 h the purified by reverse phase HPLC to give the desired product. MS cal'd 402 (MH+), exp 402 (MH+).

Step B: N-(4-aminobiphenyl-3-yl)-4-[2-[(4-chlorophenyl)amino]-1-(4-methylpiperazin-1-yl)-2-oxoethyl]benzamide. The compound from Step A above (50 mg, 0.12 mmol) was dissolved in 0.25 mL each of THF, methanol and water then 6.0 mg (0.25 mmol) of lithium hydroxide was added and the solution was allowed to stir at room temperature for 72 h. HCl (300 μL of a 1 N sol'n) was added. The solvent was evaporated and the residue was dissolved in 300 μL of DMF. 4-N-Boc-3-phenylphenylenediamine (50.0 mg, 0.180 mmol), EDC (34.5 mg, 0.180 mmol), and HOBt (24.3 mg, 0.180 mmol) were added and the solution was allowed to stir for 18 h. The solution was diluted with 50 mL of CH$_2$Cl$_2$ and washed with 50 mL of NaHCO$_3$. The solution was dried and concentrated then the residue was dissolved in 1 mL of CH$_2$Cl$_2$ then 1 mL of TFA was added. The solution was allowed to stir for 1 h then concentrated then purified by reverse phase HPLC to give the desired product. MS cal'd 554 (MH+), exp 554 (MH+).

Additional analogs were prepared in procedures similar to those described for the preparations of the above examples. The following compound was isolated as the free base.

| Cpd# | | Name | MS |
|---|---|---|---|
| 11-2 | | N-(4-aminobiphenyl-3-yl)-4-[2-[(4-chlorophenyl) amino]-1-(4-methylpiperazin-1-yl)-2-oxoethyl] benzamide | cal'd 570 (MH+), exp 570 (MH+) |

Example 12

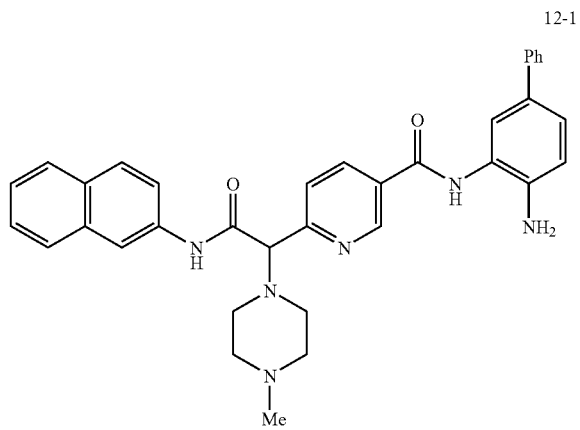

12-1

N-(4-aminobiphenyl-3-yl)-6-[1-(4-methylpiperazin-1-yl)-2-(2-naphthylamino)-2-oxoethyl]nicotinamide. The compound described in Example 10, Step A, (102 mg, 0.267 mmol) was dissolved in 0.75 mL each of THF, methanol and water then 18.0 mg (0.750 mmol) of lithium hydroxide was added and the solution was allowed to stir at room temperature for 2 h. HCl (300 μL of a 2 N sol'n) was added. The solvent was evaporated and the residue was dissolved in 500 μL of DMF. 4-N-Boc-3-phenylphenylenediamine (142 mg, 0.500 mmol), EDC (96.0 mg, 0.500 mmol), and HOBt (68.0 mg, 0.500 mmol) were added and the solution was allowed to stir for 18 h. The solution was diluted with 50 mL of $CH_2Cl_2$ and washed with 50 mL of $NaHCO_3$. The solution was dried and concentrated and the residue was dissolved in 1 mL of $CH_2Cl_2$ then 1 mL of TFA was added. The solution was allowed to stir for 1 h, then concentrated then purified by reverse phase HPLC to give the desired product. MS cal'd 570 ($MH^+$), exp 570 ($MH^+$).

Additional analogs were prepared in procedures similar to those described for the preparations of the above examples. The following compounds were isolated as the free base (parent) form.

| Cpd# | | Name | MS |
|---|---|---|---|
| 12-2 | | N-(4-aminobiphenyl-3-yl)-6-[2-(benzylamino)-1-(4-methylpiperazin-1-yl)-2-oxoethyl]nicotinamide | cal'd 535 ($MH^+$), exp 535 ($MH^+$) |
| 12-3 | | N-(4-aminobiphenyl-3-yl)-6-[2-[(4-methylphenyl)amino]-1-(4-methylpiperazin-1-yl)-2-oxoethyl]nicotinamide | cal'd 535 ($MH^+$), exp 535 ($MH^+$) |

| Cpd# | Name | MS |
|---|---|---|
| 12-4 | N-(4-aminobiphenyl-3-yl)-6-[2-[(4-chlorophenyl)amino]-1-(4-methylpiperazin-1-yl)-2-oxoethyl]nicotinamide | cal'd 555 (MH+), exp 555 (MH+) |

Example 13

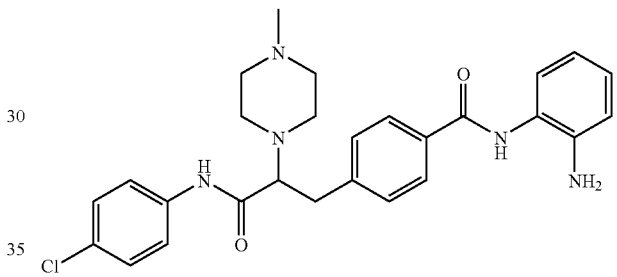

13-1

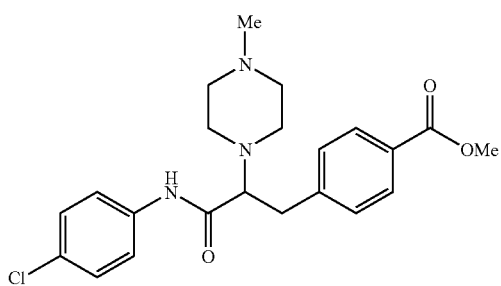

Step A: Methyl 4-[3-[(4-chlorophenyl)amino]-2-(4-methylpiperazin-1-yl)-3-oxopropyl]benzoate. Methyl 4-formylmethylbenzoate (52.3 mg, 0.294 mmol), 4-chlorophenyl isocyanide (40.4 mg, 0.294 mmol), N-methylpiperazine (39.1 μL, 0.352 mmol) and AcOH (16.6 μL, 0.294 mmol) were dissolved in 100 μL of trifluoroethanol and heated at 50° C. for 3 hours. The reaction mixture was diluted with 2 mL of methanol and purified by reverse phase HPLC to afford the desired product. MS cal'd 416.2 (MH+), exp 416.2 (MH+).

Step B: N-(2-aminophenyl)-4-[3-[(4-chlorophenyl)amino]-2-(4-methylpiperazin-1-yl)-3-oxopropyl]benzamide. The compound from Step A above (68.9 mg, 0.166 mmol) was dissolved in THF (1 mL) and methanol (0.2 mL). To this solution, was added LiOH solution in water (22.3 mg, 0.931 mmol/0.4 mL H$_2$O). The resulting solution was stirred at room temperature for 8 hours to give 100% conversion, then neutralized with HCl (conc., 77 μL). The solvent was evaporated to afford white solid, which included the acid and small amount of LiCl. The white solid (66.5 mg), benzene-1,2-diamine (26.9 mg, 0.249 mmol), EDCI (47.7 mg, 0.249 mmol) and HOBt (33.6 mg, 0.249 mmol) were dissolved in 0.6 mL DMF. The resulting solution was stirred at room temperature for 4 hours. The reaction mixture was diluted with 20 mL of CH$_2$Cl$_2$. The organic solution was washed with 10 mL of NaHCO$_3$ (sat'd), 10 mL of H$_2$O, and 10 mL of brine successively, dried over MgSO$_4$. The filtrate was concentrated to give crude product which was purified by reversed phase HPLC to give the desired product. $^1$H NMR (600 MHz, (CD$_3$)$_2$CO) δ 9.37 (d, J=11.1 Hz, 1H), 8.93 (br s, 1H), 7.81 (dm, 2H, J=8.0 Hz, 2H), 7.50-7.56 (m, 2H), 7.28-7.36 (m, 2H), 7.12-7.20 (m, 3H), 6.86 (tm, J=7.3 Hz, 1H), 6.73 (dd, J=1.1 and 8.0 Hz, 1H), 6.54 (tm, J=7.3 Hz, 1H), 3.46-3.54 (m, 1H), 3.12-3.20 (m, 1H), 2.92 (dd, J=5.7 and 13.6 Hz, 1H), 2.62-2.84 (m, 4H), 2.14-2.36 (m, 4H), 1.92 (s, 3H). MS cal'd 492.2 (MH+), exp 492.2 (MH+).

Additional analogs were prepared in procedures similar to those described for the preparations of the above examples. The following compound was isolated as the TFA salt.

| Cpd# | | Name | MS |
|---|---|---|---|
| 13-2 | (structure) | N-(2-aminophenyl)-4-[2-(4-methylpiperazin-1-yl)-3-(2-naphthylamino)-3-oxopropyl]benzamide | cal'd 508 (MH+), exp 508 (MH+) |

Example 14

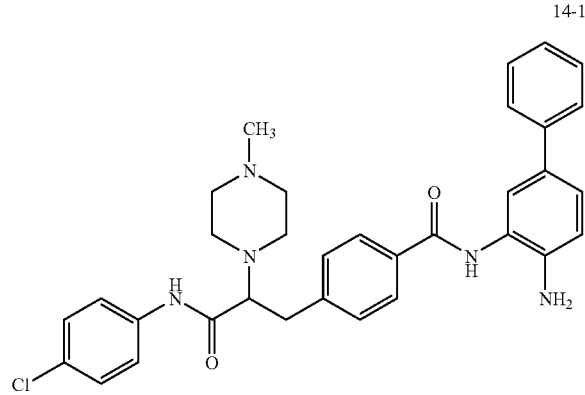

14-1

Step A: N-(4-aminobiphenyl-3-yl)-4-[3-[(4-chlorophenyl)amino]-2-(4-methylpiperazin-1-yl)-3-oxopropyl]benzamide. The compound described in Example 13, Step A, (77.3 mg, 0.1 mmol) was dissolved in THF (1 mL) and methanol (0.2 mL). To this solution, was added LiOH solution in water (20 mg, 0.835 mmol/0.4 mL H$_2$O). The resulting solution was stirred at room temperature for 4 hours to give 100% conversion, then neutralized with 0.2 mL of 6 N HCl. The solvent was evaporated to afford white solid, which included the acid and small amount of LiCl. The white solid, tert-butyl (3-aminobiphenyl-4-yl)carbamate (54.0 mg, 0.19 mmol), EDCI (36.0 ng, 0.19 mmol) and HOBT (25.7 mg, 0.19 mmol) were dissolved in 1.0 mL DMF. The resulting solution was stirred at room temperature overnight. The reaction mixture was diluted with 20 mL of CH$_2$Cl$_2$. The organic solution was washed with H$_2$O (10 mL×2) and 10 mL of brine successively, dried over MgSO$_4$. The filtrate was concentrated to give EDCI coupling product which was dissolved in 0.5 mL of CH$_2$Cl$_2$ and 0.5 mL of TFA was added. The solution was allowed to stir for 10 min. The reaction mixture was diluted with 20 mL of CH$_2$Cl$_2$. The organic solution was washed with 10 mL of NaHCO$_3$ (sat'd), 10 mL of H$_2$O, and 10 mL of brine successively, dried over MgSO$_4$. The filtrate was concentrated, diluted with methanol and purified by reversed phase HPLC to give the desired product. $^1$H NMR (600 MHz, CD$_3$OD) δ 7.98 (d, J=8.2 Hz, 2H), 7.60-7.66 (m, 4H), 7.42-7.50 (m, 7H), 7.36 (tm, J=7.6 Hz, 1H), 7.26 (dm, J=9.1 Hz, 2H), 3.67 (dd, J=5.3 and 10.0 Hz, 1H), 3.49 (br s, 2H), 3.24-3.32 (m, 4H), 3.10 (dd, J=5.6 and 13.2 Hz, 1H), 3.00-3.16 (m, 2H), 2.88 (s, 3H), 2.74-2.80 (m, 1H). MS cal'd 568.2 (MH+), exp 568.2 (MH+).

Additional analogs were prepared in procedures similar to those described for the preparations of the above examples. Unless otherwise indicated, the following compounds were isolated as TFA salts.

| Cpd# | | Name | MS |
|---|---|---|---|
| 14-2 | (structure) | N-(4-aminobiphenyl-3-yl)-4-[3-(benzylamino)-2-(4-methylpiprazin-1-yl)-3-oxopropyl]benzamide | cal'd 548 (MH+), exp 548 (MH+) |

| Cpd# | Name | MS |
|---|---|---|
| 14-3 | 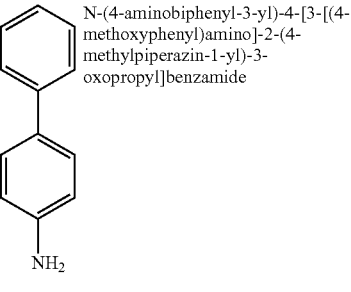 N-(4-aminobiphenyl-3-yl)-4-[3-[(4-methoxyphenyl)amino]-2-(4-methylpiperazin-1-yl)-3-oxopropyl]benzamide | cal'd 564 (MH$^+$), exp 564 (MH$^+$) |
| 14-4 | 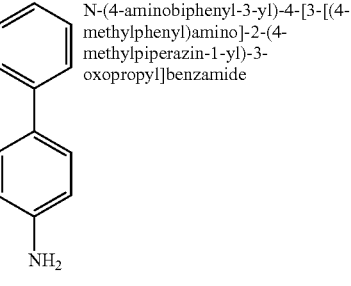 N-(4-aminobiphenyl-3-yl)-4-[3-[(4-methylphenyl)amino]-2-(4-methylpiperazin-1-yl)-3-oxopropyl]benzamide | cal'd 548 (MH$^+$), exp 548 (MH$^+$) |
| 14-5 | 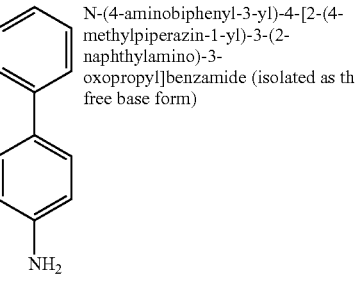 N-(4-aminobiphenyl-3-yl)-4-[2-(4-methylpiperazin-1-yl)-3-(2-naphthylamino)-3-oxopropyl]benzamide (isolated as the free base form) | cal'd 584 (MH$^+$), exp 584 (MH$^+$) |

Example 14A

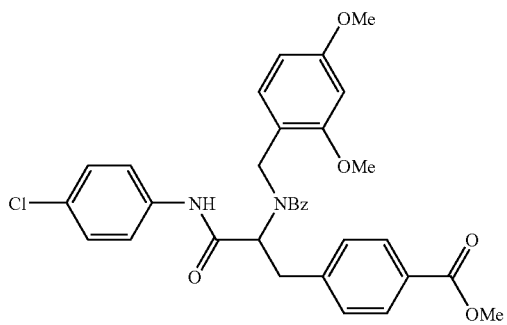

Step A: Methyl 4-{2-[benzoyl(2,4-dimethoxybenzyl)amino]-3-[(4-chlorophenyl)amino]-3-oxopropyl}benzoate. Methyl 4-formylmethylbenzoate (56.3 mg, 0.316 mmol, 4-chlorophenyl isocyanide (43.5 mg, 0.316 mmol), 1-(2,4-dimethoxyphenyl)methanamine (56.9 µL, 0.379 mmol) and benzoic acid (38.6 mg, 0.316 mmol) were dissolved in 100 µL of trifluoroethanol and heated at 50° C. for 2 hours. The reaction mixture was diluted with 2 mL of methanol and purified by reversed phase HPLC to afford the desired product. MS cal'd 587.2 (MH+), exp 587.2 (MH+).

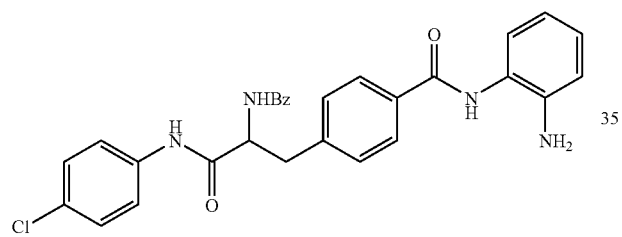

Step B: 4-{[(2-Aminophenyl)amino]carbonyl}-Nα-benzoyl-N-(4-chlorophenyl)phenyl-alaninamide. The compound from Step A above (41.6 mg, 0.071 mmol) was dissolved in THF (1 mL) and methanol (0.2 mL). To this solution, was added LiOH solution in water (23.9 mg, 1.0 mmol/0.4 mL H$_2$O). The resulting solution was stirred at room temperature for 7 hours to give 100% conversion, then neutralized with HCl (conc., 83 µL). The solvent was evaporated to afford yellow solid, which included the acid and a small amount of LiCl. The yellow solid (80.4 mg), tert-butyl (2-aminophenyl)carbamate (22.1 mg, 0.106 mmol), EDCI (20.3 mg, 0.106 mmol) and HOBT (14.3 mg, 0.106 mmol) were dissolved in 0.6 mL DMF. The resulting solution was stirred at room temperature for 1 hour. The reaction mixture was diluted with 20 mL of CH$_2$Cl$_2$. The organic solution was washed with 10 mL of NaHCO$_3$ (sat'd), 10 mL of H$_2$O, 10 mL of 0.5 N HCl, 10 mL of H$_2$O and 10 mL of brine successively, dried over MgSO$_4$. The filtrate was concentrated to give 48.7 mg (90%) of EDCI coupling product which was dissolved in 0.5 mL of CH$_2$Cl$_2$ and 0.5 mL of TFA was added. The solution was allowed to stir for 10 min. The reaction mixture was diluted with 20 mL of CH$_2$Cl$_2$. The organic solution was washed with 10 mL of NaHCO$_3$ (sat'd), 10 mL of H$_2$O, and 10 mL of brine successively, dried over MgSO$_4$. The filtrate was concentrated to give 21.7 mg of crude product as yellow solid which was recrystallized from methanol and CH$_2$Cl$_2$ to give the desired product as a white solid. MS cal'd 513.2 (MH+), exp 513.1 (MH+).

Example 15

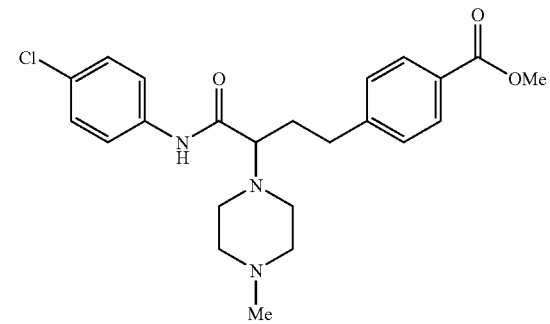

Step A: Methyl 4-[4-[(4-chlorophenyl)amino]-3-(4-methylpiperazin-1-yl)-4-oxobutyl]benzoate. Methyl 4-(3-oxopropyl)benzoate (43.5 mg, 0.226 mmol), 4-chlorophenyl isocyanide (43.5 mg, 0.316 mmol), N-methylpiperazine (40.0 µL, 0.36 mmol) and AcOH (20.0 µL, 0.36 mmol) were dissolved in 100 µL of trifluoroethanol and heated at 50° C. for 3 hours. The reaction mixture was diluted with 2 mL of methanol and purified by reversed phase HPLC to afford the desired product. MS cal'd 430.2 (MH+), exp 430.1 (MH+).

15-1

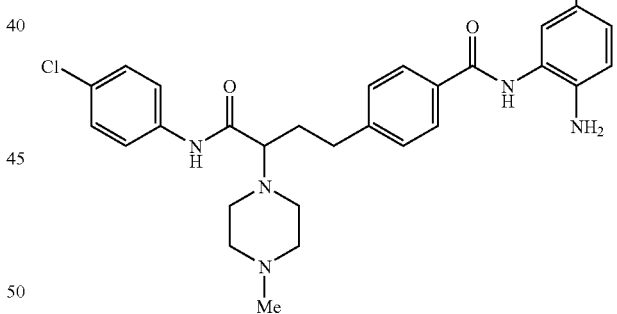

Step B: N-(4-aminobiphenyl-3-yl)-4-[4-[(4-chlorophenyl)amino]-3-(4-methylpiperazin-1-yl)-4-oxobutyl]benzamide. The compound from Step A above (45.0 mg, 0.10 mmol) was dissolved in THF (1 mL) and methanol (0.2 mL). To this solution, was added LiOH solution in water (40 mg, 1.67 mmol/0.8 mL H$_2$O). The resulting solution was stirred at room temperature for 4 hours to give 100% conversion, then neutralized with 0.27 mL of 6N HCl. The solvent was evaporated to afford white solid, which included the acid and small amount of LiCl. The white solid, tert-butyl (3-aminobiphenyl-4-yl)carbamate (42.6 mg, 0.15 mmol), EDCI (28.7 mg, 0.15 mmol) and HOBt (20.3 mg, 0.15 mmol) were dissolved in 1.0 mL DMF. The resulting solution was stirred at room temperature overnight. The reaction mixture was diluted with 20 mL of CH$_2$Cl$_2$. The organic solution was washed with H$_2$O (10 mL×2) and 10 mL of brine successively, dried over MgSO$_4$. The filtrate was concentrated to give EDCI coupling product which was dissolved in 0.5 mL of CH$_2$Cl$_2$ and 0.5 mL of TFA was added. The solution was allowed to stir for 10 ml. The reaction mixture was diluted with 20 mL of CH$_2$Cl$_2$. The organic solution was washed with 10 mL of NaHCO$_3$ (sat'd), 10 mL of H$_2$O, and 10 mL of brine successively, dried over MgSO$_4$. The filtrate was concentrated, diluted with methanol and purified by reversed phase HPLC to give the desired product. $^1$H NMR (600 MHz, CD$_3$OD) δ 7.93 (d, J=8.2 Hz, 2H), 7.59 (dm, J=8.9 Hz, 2H), 7.54 (dm, J=7.3 Hz, 2H), 7.47 (d, J=2.0 Hz, 1H), 7.33-7.40 (m, 5H), 7.30 (dm, J=8.9 Hz, 2H), 7.23 (tm, J=7.4 Hz, 1H), 6.98 (d, J=8.3 Hz, 1H), 3.20 (dd, J=8.2 and 5.9 Hz, 1H), 2.77 (t, J=7.6 Hz, 1H), 2.62-2.76 (m, 5H), 2.40-2.60 (m, 3H), 2.26 (s, 3H), 2.04-2.14 (m, 2H). MS cal'd 582.3 (MH$^+$), exp 582.3 (MH$^+$).

Additional analogs were prepared in procedures similar to those described for the preparations of the above examples. The following compounds were isolated as free base (parent) forms.

| Cpd # | Structure | Name | MS |
|---|---|---|---|
| 15-2 | | N-(4-aminobiphenyl-3-yl)-4-[4-(benzylamino)-3-(4-methylpiperazin-1-yl)-4-oxobutyl]benzamide | cal'd 562 (MH$^+$), exp 562 (MH$^+$) |
| 15-3 | | N-(4-aminobiphenyl-3-yl)-4-[3-(4-methylpiperazin-1-yl)-4-(2-naphthylamino)-4-oxobutyl]benzamide | cal'd 598 (MH$^+$), exp 598 (MH$^+$) |
| 15-4 | | N-(4-aminobiphenyl-3-yl)-4-[4-[(4-methylphenyl)amino]-3-(4-methylpiperazin-1-yl)-4-oxobutyl]benzamide | cal'd 562 (MH$^+$), exp 562 (MH$^+$) |

| Cpd # | | Name | MS |
|---|---|---|---|
| 15-5 | 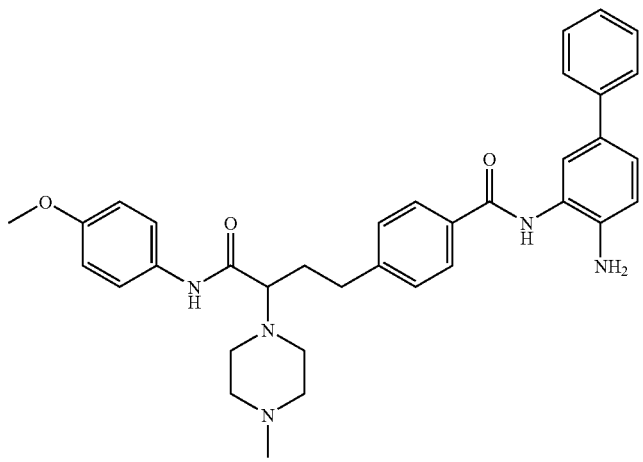 | N-(4-aminobiphenyl-3-yl)-4-[4-[(4-methoxyphenyl)amino]-3-(4-methylpiperazin-1-yl)-4-oxobutyl]benzamide | cal'd 578 (MH+), exp 578 (MH+) |

Example 16

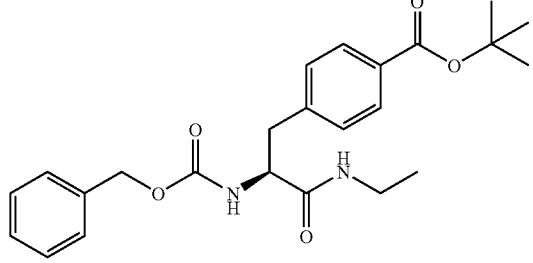

Step A: Tert-butyl 4-[(2S)-2-{[(benzyloxycarbonyl) amino}-3-(ethylamino)-3-oxopropyl]-benzoate. (2S)-2-{[(benzyloxy)carbonyl]amino}-3-[4-(tert-butoxycarbonyl) phenyl]propanoic acid (2 g, 5 mmol) was dissolved in DMF (50 mL). EDC (2.88 g, 15.05 mmol) and HOBT (2.05, 15.17 mmol) were added and allowed to stir for about 20 minutes at room temperature. Ethylamine (4 mL, 8 mmol, 2M in THF) was added. The reaction was allowed to stir overnight at 60° C. DMF was removed under reduced pressure. The resulting oil was dissolved in ethyl acetate and washed with saturated sodium bicarbonate. The water layer was extracted three additional times with ethyl acetate. The combined organic layer was dried over sodium sulfate, filtered, and concentrated. The resulting material was purified by column chromatography. $^1$H NMR 600 MHz (CDCl$_3$) δ 7.90 (d, 2H, J=8.1 Hz), 7.32 (m, 5H), 7.23 (d, 2H, J=8.1 Hz), 5.56 (s, 1H), 5.31 (s, 1H), 5.06 (AB quartet, 2H, J=13.8 Hz), 4.32 (m, 1H), 3.19 (m, 2H), 3.09 (m, 2H), 1.56 (s, 9H), 1.00 (t, 3H, J=7.3 Hz). MS: cal'd 427 (MH+), exp 427 (MH+).

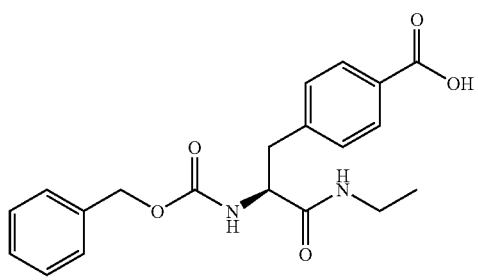

Step B: 4-[(2S)-2-{[(benzyloxy)carbonyl]amino-3-(ethylamino)-3-oxopropyl]benzoic acid. Tert-butyl 4-[(2S)-2-{[(benzyloxycarbonyl]amino}-3-(ethylamino)-3-oxopropyl] benzoate (2.2713 g, 5.33 mmol) was dissolved in dichloromethane and trifluoroacetic acid (2:1 mix) and allowed to stir until the ester was hydrolyzed completely as indicated by LCMS. The reaction was then concentrated. The resulting material was carried through to the next step unpurified. MS: cal'd 371 (MH+), exp 371 (MH+).

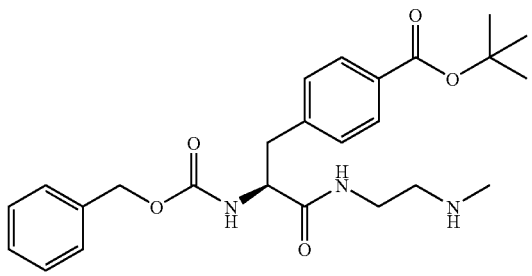

Step C: 4-((2S)-2-{[(benzyloxy)carbonyl]amino}-3-{[2-(methylamino)ethyl]amino}-3-oxopropyl)benzoic acid. Prepared from (2S)-2-{[(benzyloxy)carbonyl]amino}-3-[4-(tert-butoxycarbonyl)phenyl]propanoic acid via the procedure described in Step A. MS: cal'd 456 (MH+), exp 456 (MH+).

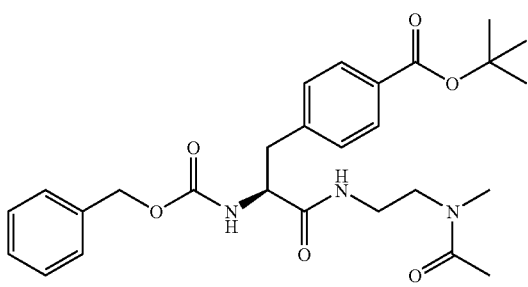

Step D: Tert-butyl-4-((2S)-3-({2-[acetyl(methyl)amino]ethyl}amino)-2-{[(benzyloxy)-carbonyl]amino}-3-oxopropyl)benzoate. Tert-butyl-4-((2S)-2-{[(benzyloxy)carbonyl]amino}-3-{[2-(methylamino)ethyl]amino}-3-oxopropyl)benzolate (0.3050 g, 0.670 mmol) was dissolved in dichloromethane. Pyridine (0.1 ml, 1.236 mmol) and acetic anhydride (0.1 ml, 1.060 mmol) were added. The reaction was allowed to stir overnight at room temperature. The reaction was transferred to a separatory funnel and washed with saturated sodium bicarbonate. The aqueous layer was extracted three times with dichloromethane. The combined organic layer was dried over sodium sulfate, filtered, and concentrated. The resulting material was purified by column chromatography. MS cal'd 498 (MH$^+$), exp 498 (MH$^+$).

Additional analogs were prepared in procedures similar to those described for the preparations above and Example 4. The following compounds were isolated as TFA salts.

| Cpd # | Name | MS |
|---|---|---|
| 16-1 | Benzyl [(1S)-1-[4-({[2-amino-5-(2-thienyl)phenyl]amino}carbonyl)benzyl]-2-(ethylamino)-2-oxoethyl} carbamate | cal'd 543 (MH$^+$), exp 543 (MH$^+$) |
| 16-2 | Benzyl [(1S)-1-[4-({[2-amino-5-(3-thienyl)phenyl]amino}carbonyl)benzyl]-2-(ethylamino)-2-oxoethyl} carbamate | cal'd 543 (MH$^+$), exp 543 (MH$^+$) |
| 16-3 | Benzyl [(1S)-1-[4-({[2-amino-5-(2-thienyl)phenyl]amino}carbonyl)benzyl]-2-(methylamino)-2-oxoethyl} carbamate | cal'd 529 (MH$^+$), exp 529 (MH$^+$) |

-continued
| Cpd # | | Name | MS |
|---|---|---|---|
| 16-4 | 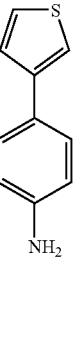 | Benzyl [(1S)-1-[4-({[2-amino-5-(3-thienyl)phenyl]amino} carbonyl)benzyl]-2-(methylamino)-2-oxoethyl]carbamate | cal'd 529 (MH+), exp 529 (MH+) |
| 16-5 | 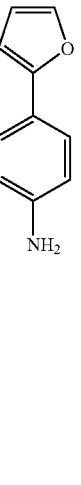 | Benzyl [(1S)-1-[4-({[2-amino-5-(2-thienyl)phenyl]amino} carbonyl)benzyl]-2-(4-methylpiperazin-1-1yl)-2-oxoethyl]carbamate | cal'd 598 (MH+), exp 598 (MH+) |
| 16-6 | 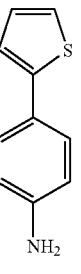 | Benzyl [(1S)-1-[4-({[2-amino-5-(2-thienyl)phenyl]amino} carbonyl)benzyl]-2-morpholin-4-yl-2-oxoethyl]carbamate | cal'd 585 (MH+), exp 585 (MH+) |

-continued
| Cpd # | | Name | MS |
|---|---|---|---|
| 16-7 | 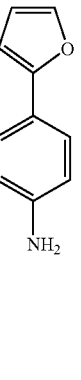 | Benzyl [(1S)-1-[4-({[2-amino-5-(2-thienyl)phenyl]amino} carbonyl)benzyl]-2-{[2-(dimethylamino)ethyl]amino}-2-oxoethyl]carbamate | cal'd 586 (MH$^+$), exp 586 (MH$^+$) |
| 16-8 | 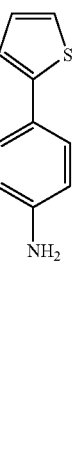 | Benzyl [(1S)-1-[4-({[2-amino-5-(2-thienyl)phenyl]amino} carbonyl)benzyl]-2-(benzylamino)-2-oxoethyl]carbamate | cal'd 605 (MH$^+$), exp 605 (MH$^+$) |
| 16-9 | 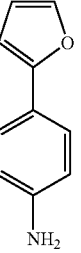 | Benzyl {(1S)-2-amino-1-[4-({[2-amino-5-(2-thienyl)phenyl]amino}carbonyl)benzyl]-2-oxoethyl}carbamate | cal'd 515 (MH+), exp 515 (MH+) |

-continued
| Cpd # | | Name | MS |
|---|---|---|---|
| 16-10 | 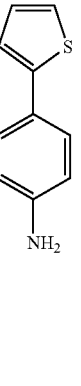 | (2S)-3-[4-({[2-amino-5-(2-thienyl)phenyl]amino}carbonyl)phenyl]-2-{[(benzyloxy)carbonyl]amino}propanoic acid | cal'd 516 (MH+), exp 516 (MH+) |
| 16-11 | 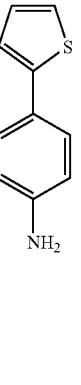 | Benzyl [(1S)-1-[4-({[2-amino-5-(2-thienyl)phenyl]amino}carbonyl)benzyl]-2-(dimethylamino)-2-oxoethyl]carbamate | cal'd 543 (MH+), exp 543 (MH+) |
| 16-12 | 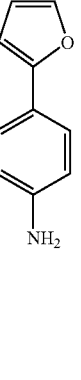 | Benzyl [(1S)-1-[4-({[2-amino-5-(2-thienyl)phenyl]amino}carbonyl)benzyl]-2-(isopropylamino)-2-oxoethyl]carbamate | cal'd 557 (MH+), exp 557 (MH+) |

-continued
| Cpd # | | Name | MS |
|---|---|---|---|
| 16-13 | 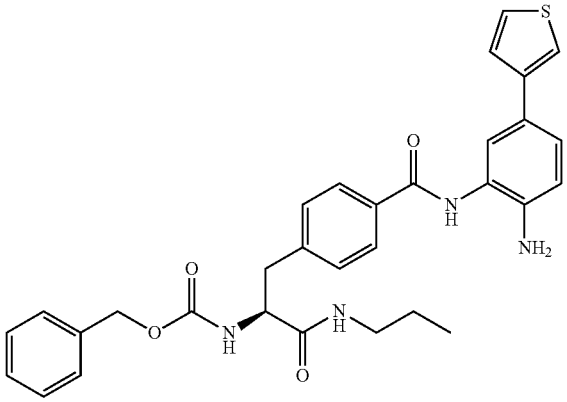 | Benzyl [(1S)-1-[4-({[2-amino-5-(3-thienyl)phenyl]amino}carbonyl)benzyl]-2-oxo-2-(propylamino)ethyl]carbamate | cal'd 557 (MH+), exp 557 (MH+) |
| 16-14 | 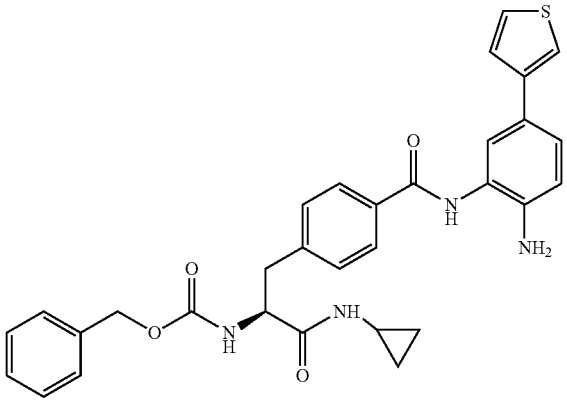 | Benzyl [(1S)-1-[4-({[2-amino-5-(3-thienyl)phenyl]amino}carbonyl)benzyl]-2-(cyclopropylamino)-2-oxoethyl]carbamate | cal'd 555 (MH+), exp 555 (MH+) |
| 16-15 | 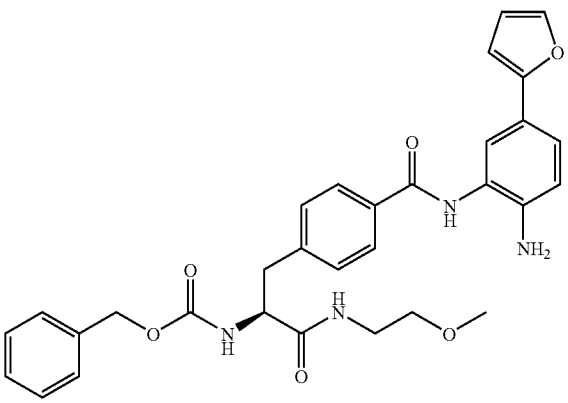 | Benzyl {(1S)-1-[4-({[2-amino-5-(2-thienyl)phenyl]amino}carbonyl)benzyl]-2-[(2-methoxyethyl)amino)-2-oxoethyl}carbamate | cal'd 573 (MH+), exp 573 (MH+) |

| Cpd # | | Name | MS |
|---|---|---|---|
| 16-16 | 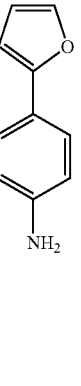 | Benzyl ((1S)-1-[4-({[2-amino-5-(2-thienyl)phenyl]amino}carbonyl)benzyl]-2-{[2-(dimethylamino)-2-oxoethyl]amino}-2-oxoethyl)carbamate | cal'd 600 (MH+), exp 600 (MH+) |
| 16-17 | 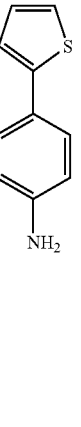 | Benzyl {(1S)-1-[4-({[2-amino-5-(2-thienyl)phenyl]amino}carbonyl)benzyl]-2-[[2-(dimethylamino)-2-oxoethyl](methyl)amino]-2-oxoethyl}carbamate | cal'd 614 (MH+), exp 614 (MH+) |
| 16-18 | 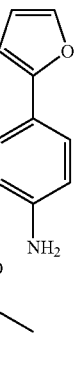 | Benzyl {(1S)-2-{[2-(acetylamino)ethyl]amino}-1-[4-({[2-amino-5-(2-thienyl)phenyl]amino}carbonyl)benzyl]-2-oxoethyl}carbamate | cal'd 600 (MH+), exp 600 (MH+) |

| Cpd # | | Name | MS |
|---|---|---|---|
| 16-19 | 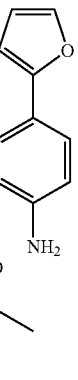 | Benzyl {(1S)-2-({2-[acetyl(methyl)amino]ethyl}amino)-1-[4-({[2-amino-5-(2-thienyl)phenyl]amino}carbonyl)benzyl]-2-oxoethyl}carbamate | cal'd 614 (MH+), exp 614 (MH+) |
| 16-20 | 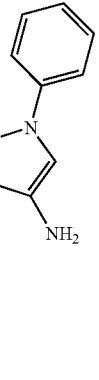 | Benzyl [1(S)-(4-{[4-amino-1-phenyl-1H-pyrazol-3-yl)amino] carbonyl}benzyl)-2-(methylamino)-2-oxoethyl]carbamate | cal'd 513 (MH+), exp 513 (MH+) |

Example 17

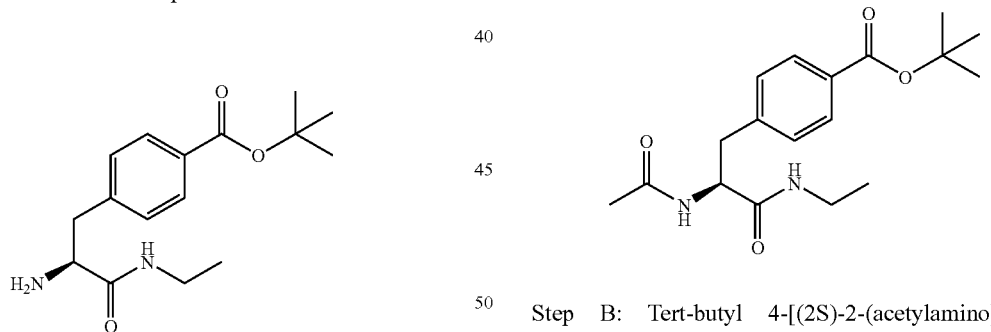

Step A: Tert-butyl 4-[(2S)-2-amino-3-(ethylamino)-3-oxopropyl]benzoate. Tert-butyl 4-[(2S)-2-{[(benzyloxycarbonyl]amino}-3-(ethylamino)-3-oxopropyl]benzoate (0.9455 g, 2.22 mmol) was dissolved in methanol. Palladium on carbon (10%) was added. The reaction was allowed to stir under nitrogen at atmospheric pressure and room temperature overnight. The reaction mixture was filtered over celite. The celite was washed several times with methanol. The methanol solution was concentrated. The resulting material was carried on unpurified. MS: cal'd 293 (MH+), exp 293 (MH+).

Step B: Tert-butyl 4-[(2S)-2-(acetylamino)-3-(ethylamino)-3-oxopropyl]benzoate. Tert-butyl 4-[(2S)-2-amino-3-(ethylamino)-3-oxopropyl]benzoate was dissolved in dichloromethane (3.5 mL). Pyridine (0.05 mL) and acetic anhydride (0.05 mL) were added. The reaction was allowed to stir overnight at room temperature under nitrogen. The reaction was transferred to a separatory funnel and washed with saturated sodium bicarbonate. The aqueous layer was extracted three additional times with dichloromethane. The combined organic layer was dried over sodium sulfate, filtered, and concentrated. The resulting material was purified by column chromatography. $^1$H NMR 600 MHz (CDCl$_3$) δ 7.86 (d, 2H, J=8.4 Hz), 7.23 (d, 2H, J=8.4 Hz), 6.89 (s, 1H), 6.47 (s, 1H), 4.68 (m, 1H), 3.15 (m, 2H), 3.06 (m, 2H), 1.93 (s, 3H), 1.55 (s, 9H), 0.99 (m, 3H). MS: cal'd 335 (MH+), exp 335 (MH+).

Additional analogs were prepared in procedures similar to those described for the preparations above and Example 4. The following compounds were isolated as TFA salts.

| Cpd # | | Name | MS |
|---|---|---|---|
| 17-1 | 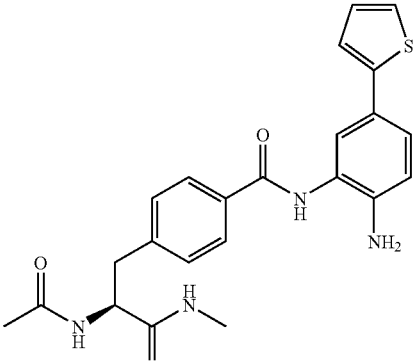 | 4-[(2S)-2-(acetylamino)-3-(methylamino)-3-oxopropyl]-N-2-amino-5-(2-thienyl)phenyl]benzamide | cal'd 437 (MH⁺), exp 437 (MH⁺) |
| 17-2 | 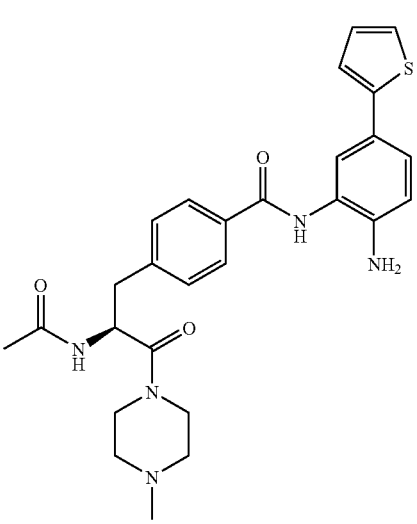 | 4-[(2S)-2-(acetylamino)-3-(4-methylpiperzin-1-yl)-3-oxopropyl]-N-2-amino-5-(2-thienyl)phenyl]benzamide | cal'd 506 (MH⁺), exp 506 (MH⁺) |
| 17-3 | 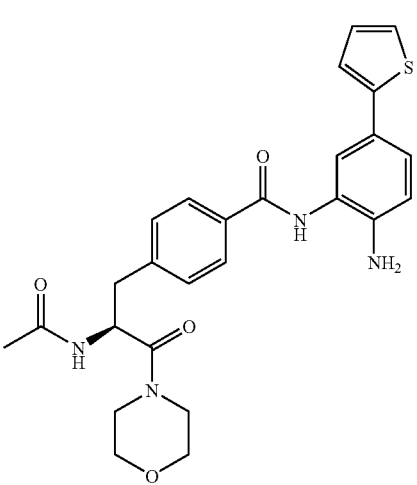 | 4-[(2S)-2-(acetylamino)-3-morpholin-4-yl-3-oxopropyl]-N-2-amino-5-(2-thienyl)phenyl]benzamide | cal'd 493 (MH⁺), exp 493 (MH⁺) |

| Cpd # | | Name | MS |
|---|---|---|---|
| 17-4 | 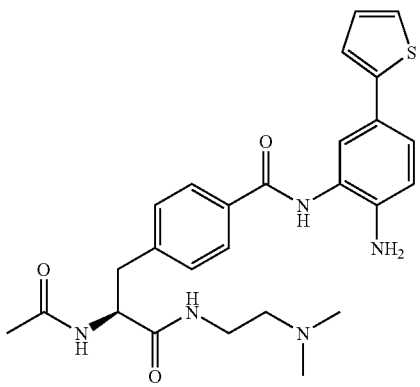 | 4-[(2S)-2-(acetylamino)-3-{(2-(dimethylamino)ethyl]amino)-3-oxopropyl]-N-2-amino-5-(2-thienyl)phenyl]benzamide | cal'd 494 (MH+), exp 494 (MH+) |
| 17-5 | 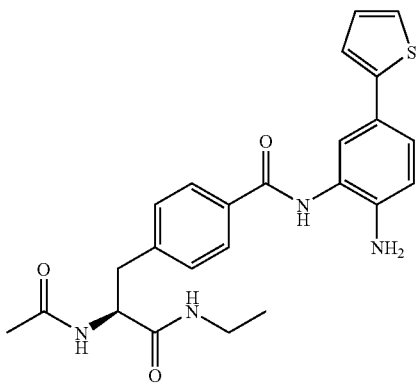 | 4-[(2S)-2-(acetylamino)-3-(ethylamino)-3-oxopropyl]-N-[2-amino-5-(2-thienyl)phenyl]benzamide | cal'd 451 (MH+), exp 451 (MH+) |
| 17-6 | 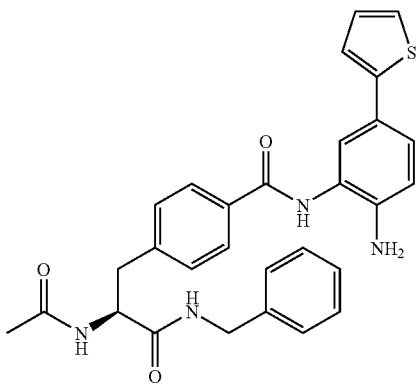 | 4-[(2S)-2-(acetylamino)-3-(benzylamino)-3-oxopropyl]-N-[2-amino-5-(2-thienyl)phenyl]benzamide | cal'd 513 (MH+), exp 513 (MH+) |

| Cpd # | | Name | MS |
|---|---|---|---|
| 17-7 | 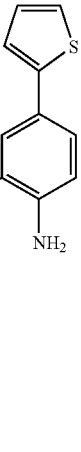 | N-[2-amino-5-(2-thienyl)phenyl]-4-{(2S)-2-[(methylsulfonyl)amino]-3-morpholin-4-yl-3-oxopropyl}benzamide | cal'd 529 (MH+), exp 529 (MH+) |
| 17-8 | 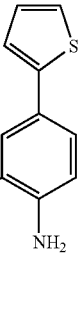 | N-[2-amino-5-(2-thienyl)phenyl]-4-{(2S)-3-(ethylamino)-2-[(methylsulfonyl)amino]-3-oxopropyl}benzamide | cal'd 487 (MH+), exp 487 (MH+) |
| 17-9 | 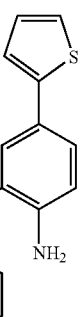 | N-[2-amino-5-(2-thienyl)phenyl]-4-{(2S)-3-(benzylamino)-2-[(methylsulfonyl)amino]-3-oxopropyl}benzamide | cal'd 549 (MH+), exp 549 (MH+) |

| Cpd # | | Name | MS |
|---|---|---|---|
| 17-10 | 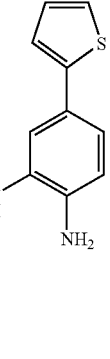 | pyridin-3-ylmethyl[(1S)-1-[4-({[2-amino-5-(2-thienyl)phenyl]amino}carbonyl)benzyl]-2-(ethylamino)-2-oxoethyl]carbamate | cal'd 544 (MH+), exp 544 (MH+) |
| 17-11 | 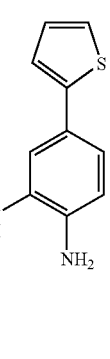 | pyridin-3-ylmethyl[(1S)-1-[4-({[2-amino-5-(2-thienyl)phenyl]amino}carbonyl)benzyl]-2-(methylamino)-2-oxoethyl]carbamate | cal'd 530 (MH+), exp 530 (MH+) |
| 17-12 | 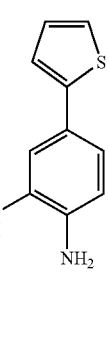 | N-[(1S)-1-[4-({[2-amino-5-(3-thienyl)phenyl]amino}carbonyl)benzyl]-2-oxo-2-(propylamino)ethyl]thiophene-2-carboxamide | cal'd 533 (MH+), exp 533 (MH+) |

Example 18

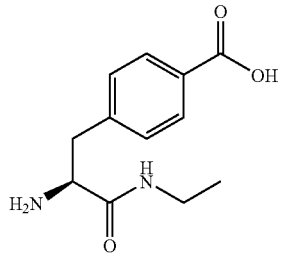

Step A: 4-[(2S)-2-amino-3-(ethylamino)-3-oxopropyl]benzoic acid. Prepared from 4-[(2S)-2-{[(benzyloxy)carbonyl]amino-3-(ethylamino)-3-oxopropyl]benzoic acid (Example 16, Step B) via the procedure described in Example 17, Step A. MS: cal'd 237 (MH+), exp 237 (MH+).

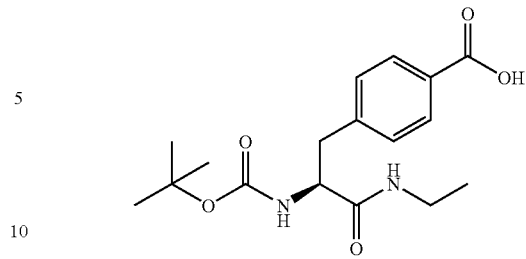

Step B: 4-[(2S)-2-[(tert-butoxycarbonyl)amino]-3-(ethylamino)-3-oxopropyl]benzoic acid. Prepared from 4-[(2S)-2-amino-3-(ethylamino)-3-oxopropyl]benzoic acid via the procedure described in Example 4, Step A. MS: cal'd 337 (MH+), exp 359 (MH+).

Additional analogs were prepared in procedures similar to those described for the preparations above and Example 4. The following compounds were isolated as TFA salts.

| Cpd # | | Name | MS |
|---|---|---|---|
| 18-1 | | 4-[(2S)-2-amino-3-(ethylamino)-3-oxopropyl]-N-[2-amino-5-(2-thienyl)phenyl]benzamide | cal'd 409 (MH+), exp 409 (MH+) |
| 18-2 | | 4-[(2S)-2-amino-3-(methylamino)-3-oxopropyl]-N-[2-amino-5-(2-thienyl)phenyl]benzamide | cal'd 395 (MH+), exp 395 (MH+) |

| Cpd # | | Name | MS |
|---|---|---|---|
| 18-3 | 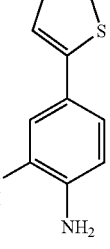 | 4-((2S)-2-amino-3-{[2-(dimethylaminoethyl)amino}-3-oxopropyl)-N-[2-amino-5-(2-thienyl)phenyl]benzamide | cal'd 452 (MH+), exp 452 (MH+) |
| 18-4 |  | 4-{(2S)-2-amino-3-[(2-methoxyethyl)amino]-3-oxopropyl}-N-[2-amino-5-(2-thienyl)phenyl]benzamide | cal'd 439 (MH+), exp 439 (MH+) |

Example 19

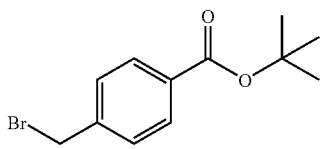

Step A: Tert-butyl 4-(bromomethyl)benzoate. Magnesium sulfate (7.8494 g, 65.21 mmol) was suspended in dichloromethane (65 mL). Concentrated sulfuric acid (0.9 mL) was added and allowed to stir for 15 minutes. 4-(bromomethyl) benzoic acid (3.4851 g, 16.21 mmol) and tert-butanol (7.8 mL) were added. The reaction was allowed to stir overnight at room temperature. Saturated sodium bicarbonate (15 ml) was added and the reaction was allowed to stir. Magnesium sulfate was filtered off. The reaction was washed with saturated sodium bicarbonate. The aqueous layer was extracted three times with dichloromethane. The combined organic layer was dried over sodium sulfate, filtered, and concentrated. The resulting material was dissolved in ethyl acetate and the product was partially recrystallized. To optimize the yield, the product remaining in the ethyl acetate was purified by column chromatography. $^1$H NMR 600 MHz (CD$_3$OD) δ 7.91 (d, 2H, J=8.2 Hz), 7.48 (d, 2H, J=8.2 Hz), 4.58 (s, 2H), 1.60 (s, 9H).

Step B: Tert-butyl 4-[2-(dimethylamino)-3-ethoxy-3-oxopropyl]benzoate. Ethyl (dimethylamino)acetate (0.16 mL, 1.11 mmol) was dissolved in THF (10 mL) and cooled to −78° C. LiHMDS (1.2 mL, 1M solution in THF) was added. The reaction was allowed to stir about 30 minutes. Tert-butyl 4-(bromomethyl)benzoate (0.3063 g, 1.13 mmol) in THF (3 mL) was slowly added to the reaction. The reaction was allowed to stir overnight under nitrogen, slowly warming to room temperature. The reaction was quenched with saturated ammonium chloride and diluted with ethyl acetate. The resulting mixture was separated. The aqueous layer was extracted three times with ethyl acetate. The combined organic layer was dried with sodium sulfate, filtered, and concentrated. The resulting residue was purified by column chromatography. $^1$H NMR 600 MHz (CDCl$_3$) δ 7.87 (m, 2H), 7.24 (m, 2H), 4.08 (m, 1H), 4.06 (m, 1H), 3.41 (dd, 1H, J=9.2, 6.0), 3.07 (dd, 1H, J=13.5, 9.3), 2.97 (dd, 1H, J=13.4, 5.8), 2.39 (s, 6H), 1.56 (s, 9H), 1.16 (m, 3H). MS: cal'd 322 (MH+), exp 322 (MH+).

131

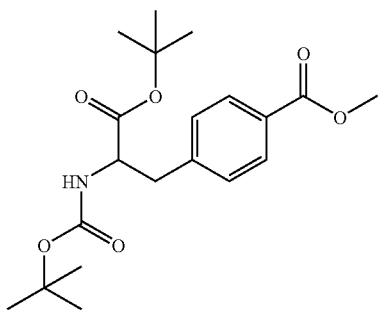

132

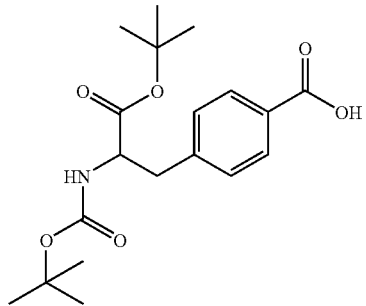

Step C: Methyl 4-{3-tert-butoxy-2-[(tert-butoxycarbonyl)amino]-3-oxopropyl}benzoate. Tert-butyl[(tert-butoxycarbonyl)amino]acetate (1.01 g, 4.37 mmol) was dissolved in THF (10 mL) and cooled to −78° C. LiHMDS (6.5 mL, 1M solution in THF) was slowly added and allowed to stir for 30 minutes. Methyl 4-(bromomethyl)benzoate (1.98 g, 8.64 mmol) in THF (6 mL) was added to the mixture and allowed to stir overnight, slowly warming to room temperature. The reaction was diluted with ethyl acetate and quenched with saturated ammonium chloride. The aqueous layer was extracted three times with ethyl acetate. The combined organic layer was dried over sodium sulfate, filtered, and concentrated. The resulting residue was purified by column chromatography. MS: cal'd 379 (MH+), exp 402 (MH+).

Step D: 4-{3-tert-butoxy-2-[(tert-butoxycarbonyl)amino]-3-oxopropyl}benzoic acid. Methyl 4-{3-tert-butoxy-2-[(tert-butoxycarbonyl)amino]-3-oxopropyl}benzoate (0.40 g, 1.05 mmol) was dissolved in THF (10 mL). KOSiMe$_3$ (0.27 g, 2.10 mmol) was added to the solution and allowed to stir overnight at room temperature under nitrogen. Saturated ammonium chloride was added and allowed to stir. Hydrochloric acid (2 mL, 1M solution) was added. The reaction was diluted with ethyl acetate and separated. The aqueous layer was extracted three times with ethyl acetate. The combined organic layer was dried with sodium sulfate, filtered, and concentrated. The resulting material was purified by HPLC. MS: cal'd 365 (MH+), exp 388 (MH+).

Additional analogs were prepared in procedures similar to those described for the preparations above and in Example 4. The following compounds were isolated as TFA salts.

| Cpd # | | Name | MS |
|---|---|---|---|
| 19-1 | | 2-amino-3-[4-({[2-amino-5-(3-thienyl)phenyl]amino}carbonyl)phenyl]propanoic acid | cal'd 382 (MH$^+$), exp 382 (MH$^+$) |
| 19-2 | | Ethyl 3-[4-({[2-amino-5-(2-thienyl)phenyl]amino}carbonyl)phenyl]-2-(dimethylamino)propanoate | cal'd 438 (MH$^+$), exp 438 (MH$^+$) |

Example 20

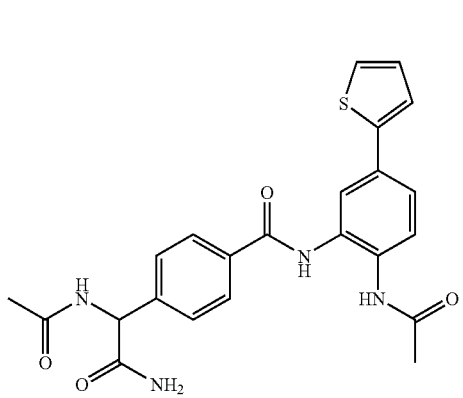

4-[1-(acetylamino)-2-amino-2-oxoethyl]-N-[2-(acetylamino)-5-(2-thienyl)phenyl]benzamide. N-[2-amino-5-(2-thienyl)phenyl]-4-(1,2-diamino-2-oxoethyl)benzamide (51 mg, 0.086 mmol) and DIPEA (52.4 μL, 0.300 mmol) were suspended in THF (1 mL) and acetic anyhdride (13 μL, 0.138 mmol) was added. The mixture was stirred at room temperature overnight. 2N HCl was added and the products extracted into EtOAc. The combined organic extracts were washed with brine, dried over MgSO$_4$ and concentrated in vacuo. The residue was purified by prep-HPLC to give the desired product as a blue-green solid. $^1$H NMR (DMSO-d$_6$, 600 MHz) δ 9.89 (s, 1H), 9.71 (s, 1H), 8.55 (d, J=7.8 Hz, 1H), 7.91 (m, 3H), 7.75 (s, 1H), 7.55 (m, 3H), 7.51 (d, J=5.4 Hz, 1H), 7.49 (m, 1H), 7.44 (m, 1H), 7.19 (s, 1H), 7.11 (m, 1H), 5.48 (d, J=7.8 Hz, 1H), 2.07 (s, 3H), 1.89 (s, 3H). MS: cal'd 451 (MH+), exp 451 (MH+).

Example 21

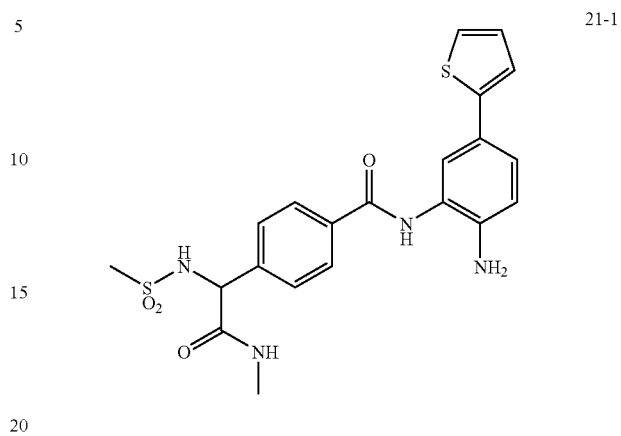

21-1

N-[2-amino-5-(2-thienyl)phenyl]-4-{2-(methylamino)-1-[(methylsulfonyl)amino]-2-oxoethyl}benzamide. 4-[1-amino-2-(methylamino)-2-oxoethyl]-N-[2-amino-5-(2-thienyl)phenyl]benzamide (20 mg, 0.053 mmol) and DIPEA (0.014 mL, 0.079 mmol) were suspended in THF (1 mL) and methanesulfonyl chloride (4.10 μL, 0.053 mmol) in THF (0.2 mL) was added. The mixture was stirred at room temperature overnight. Water was added and the products extracted into EtOAc. The combined organic extracts were washed with brine, dried over MgSO$_4$ and concentrated in vacuo. The residue was purified by prep-HPLC to give the TFA salt of the desired product as a blue-green solid. $^1$H NMR (CD$_3$OD, 600 MHz) δ 8.31 (d, J=4.8 Hz, 1H), 8.07 (d, J=8.4 Hz, 2H), 7.66 (s, 1H), 7.63 (m, 3H), 7.42 (m, 2H), 7.34 (d, J=8.4 Hz, 1H), 7.10 (t, J=4.2 Hz, 1H), 5.14 (s, 1H), 2.85 (s, 3H), 2.76 (d, J=4.8 Hz, 3H). MS: cal'd 459 (MH+), exp 459 (MH+).

Additional analogs were prepared in procedures similar to those described for the preparations of the above examples. The following compound was isolated as the TFA salt.

| Cpd # | | Name | MS |
|---|---|---|---|
| 21-2 | (structure) | N-[2-amino-5-(2-thienyl)phenyl]-4-(2-(methylamino)-1-{[(methylamino)carbonyl]amino}-2-oxoethyl)benzamide | cal'd 438 (MH+), exp 438 (MH+) |

Example 22

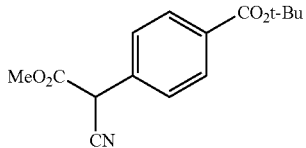

Step A: tert-Butyl 4-(1-cyano-2-methoxy-2-oxoethyl)benzoate. To a mixture of Na₃PO₄ (9.84 g, 60.0 mmol), methyl cyanoacetate (2.38 g, 24.0 mmol), and tert-butyl 4-bromobenzoate (5.14 g, 20.0 mmol) were added Pd(dba)2 (575 mg, 1.00 mmol), toluene (60 mL), and P(t-Bu)3 (10% wt in hexanes, 11.56 mL, 3.89 mmol). After degassing for 20 minutes, the reaction was stirred at 80° C. for 16 h. The resulting mixture was diluted with EtOAc, washed with H₂O and brine, dried (MgSO4), and concentrated. Flash chromatography on silica gel (0-15% EtOAc/hexanes) gave tert-butyl 4-(1-cyano-2-methoxy-2-oxoethyl)benzoate as a white solid. 1H NMR (CDCl3) δ8.02 (d, J=7.9 Hz, 2H), 7.51 (d, J=8.2 Hz, 2H), 4.79 (s, 1H), 3.79 (s, 3H), 1.58 (s, 9H). MS (ESI) calcd [M+H]+ 276.1, found 276.1.

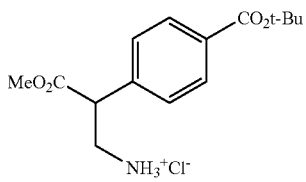

Step B: tert-Butyl 4-[1-(aminomethyl)-2-methoxy-2-oxoethyl]benzoate hydrochloride. To a solution of tert-butyl 4-(1-cyano-2-methoxy-2-oxoethyl)benzoate (3.51 g, 12.8 mmol) in MeOH (120 mL) were added concentrated HCl (2.0 mL) and Pd/C (10% wt, 850 mg). An H2 balloon was attached, and after evacuating and filling with H2 three times, the reaction was stirred at room temperature for 24 h. The black solution was then filtered through Celite and evaporated to give tert-butyl 4-[1-(aminomethyl)-2-methoxy-2-oxoethyl]benzoate hydrochloride as an off-white powder that was carried on without further purification. MS (ESI) calcd [M+H]+ 280.1, found 280.1.

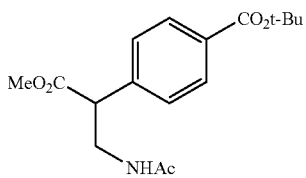

Step C: tert-Butyl 4-{1-[(acetylamino)methyl]-2-methoxy-2-oxoethyl}benzoate. To a mixture of tert-butyl 4-[1-(aminomethyl)-2-methoxy-2-oxoethyl]benzoate hydrochloride (600 mg, 1.90 mmol) in CH2Cl2 were added pyridine (0.38 mL, 4.75 mmol) and acetyl chloride (0.20 mL, 2.85 mmol). After stirring for 2 h at room temperature, the reaction mixture was diluted with EtOAc, washed (sat. CuSO4, sat. NaHCO3, brine), dried (MgSO4), and concentrated. Flash chromatography on silica gel (50-100% EtOAc/hexanes) afforded tert-butyl 4-{1-[(acetylamino)methyl]-2-methoxy-2-oxoethyl}benzoate as a thick, colorless oil. 1H NMR (CDCl3) δ7.94 (d, J=8.2 Hz, 2H), 7.28 (d, J=8.2 Hz, 2H), 5.87 (t, J=5.5 Hz, 1H), 3.96 (dd, J=8.8, 5.9 Hz, 1H), 3.71-3.60 (m, 2H), 3.67 (s, 3H), 1.93 (s, 3H), 1.57 (s, 9H). MS (ESI) calcd [M+H]+ 322.1, found 322.1.

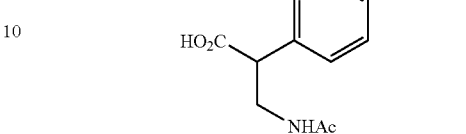

Step D: 3-(Acetylamino)-2-[4-(tert-butoxycarbonyl)phenyl]propanoic acid. To a solution of tert-butyl 4-{1-[(acetylamino)methyl]-2-methoxy-2-oxoethyl}benzoate (530 mg, 1.65 mmol) in THF (9 mL) and MeOH (3 mL) was added KOH (1N, 1.98 mL, 1.98 mmol). After stirring at room temperature for 1 h, the mixture was diluted with 0.5 M citric acid and extracted with EtOAc. The organic layer was washed with water and brine, dried (MgSO4), and concentrated to yield 3-(acetylamino)-2-[4-(tert-butoxycarbonyl)phenyl]propanoic acid as a white powder. MS (ESI) calcd [M+Na]+ 330.1, found 330.1.

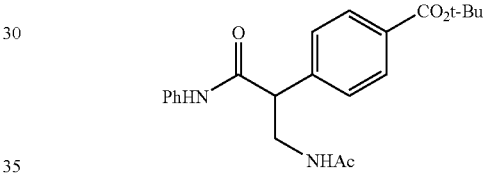

Step E: tert-Butyl 4-{1-[(acetylamino)methyl]-2-amino-2-oxoethyl}benzoate. 3-(Acetylamino)-2-[4-(tert-butoxycarbonyl)phenyl]propanoic acid (222 mg, 0.72 mmol), EDCI (207 mg, 1.08 mmol), and HOBT (127 mg, 0.94 mmol) were dissolved in DMF (7 mL) and stirred for 5 minutes before adding aniline (99 μL, 1.08 mmol). After stirring at room temperature for 18 h, the solution was concentrated. The resulting residue was taken up in EtOAc, washed (water, sat. NaHCO3, brine), dried (MgSO4), and concentrated. Flash chromatography on silica (0-4% MeOH/DCM) afforded tert-butyl 4-{1-[(acetylamino)methyl]-2-anilino-2-oxoethyl}benzoate as an off-white solid. ¹H NMR (DMSO-d6) δ10.18 (s, 1H), 8.08 (t, J=5.9 Hz, 1H), 7.84 (d, J=8.5 Hz, 2H), 7.56 (d, J=7.6 Hz, 2H), 7.46 (d, j=8.2 Hz, 2H), 7.25 (t, J=7.9 Hz, 2H), 7.00 (t, J=7.5 Hz, 1H), 4.03 (dd, J=8.2, 6.3 Hz, 1H), 3.51 (ddd, J=13.2, 8.4, 5.0 Hz, 1H), 3.42 (dt, J=12.9, 6.5 Hz, 1H), 1.74 (s, 3H), 1.50 (s, 9H). MS (ESI) calcd [M+H]+ 383.2, found 383.1.

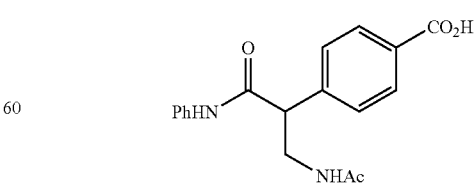

Step F: 4-{1-[(Acetylamino)methyl]-2-anilino-2-oxoethyl}benzoic acid. To a solution of tert-butyl 4-{1-[(acetylamino)methyl]-2-anilino-2-oxoethyl}benzoate (273 mg, 0.71 mmol) in CH2Cl2 (8 mL) was added trifluoroacetic acid (2 mL), and the reaction was stirred at room temperature for 2 h. The solution was evaporated to dryness to yield 4-{1-[(acetylamino)methyl]-2-anilino-2-oxoethyl}benzoic acid as an off-white powder that was carried on without further purification. MS (ESI) calcd [M+H]+ 327.1, found 327.1.

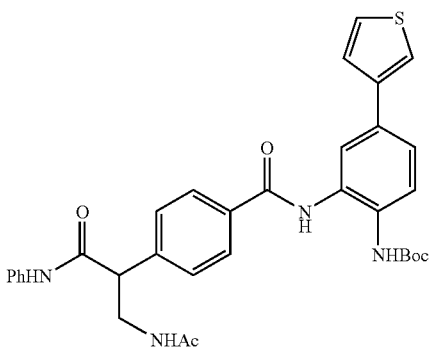

Step G: tert-Butyl [2-[(4-{1-[(acetylamino)methyl]-2-anilino-2-oxoethyl}benzoyl)amino]-4-(3-thienyl)-phenyl]carbamate. 4-{1-[(Acetylamino)methyl]-2-anilino-2-oxoethyl}benzoic acid (232 mg, 0.71 mmol), EDCI (176 mg, 0.92 mmol), and HOBT (124 mg, 0.92 mmol) were combined in DMF (8 mL) and stirred for 10 minutes before adding tert-butyl [2-amino-4-(3-thienyl)phenyl]carbamate (227 mg, 0.78 mmol). The reaction was then stirred at 60° C. for 24 h. The solution was cooled to room temperature, poured into water (40 mL), and filtered to collect an orange solid. The crude solid was dissolved in CH2Cl2 (25 mL) and hexanes (20 mL), concentrated to half volume, and filtered to give tert-butyl[2-[(4-{1-[(acetylamino)methyl]-2-anilino-2-oxoethyl}benzoyl)amino]-4-(3-thienyl)phenyl]carbamate as a white solid. MS (ESI) calcd [M+H]+ 599.2, found 599.1.

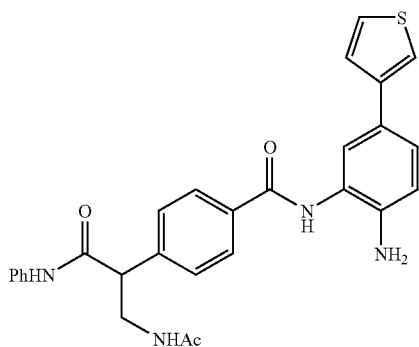

Step H: 4-{1-[(Acetylamino)methyl]-2-anilino-2-oxoethyl}-N-[2-amino-5-(3-thienyl)-phenyl]benzamide. To a solution of tert-butyl [2-[(4-{1 [(acetylamino)methyl]-2-anilino-2-oxoethyl}benzoyl)amino]-4-(3-thienyl)phenyl]carbamate (164 mg, 0.27 mmol) in CH2Cl2 (8 mL) was added trifluoroacetic acid (2 mL), and the reaction was stirred at room temperature for 2 h. Concentration yielded a yellow residue that was dissolved in EtOAc, neutralized with sat. NaHCO3, washed with brine, dried (MgSO4), and evaporated. The resulting solid was dissolved in CH2Cl2 (15 mL) and MeOH (0.5 mL). Hexanes (5 mL) were added, and upon concentration to half-volume, the mixture was filtered to isolate 4-{1-[(acetylamino)methyl]-2-anilino-2-oxoethyl}-N-[2-amino-5-(3-thienyl)phenyl]benzamide as a white solid. 1H NMR (DMSO-d6) δ10.19 (s, 1H), 9.66 (s, 1H), 8.12 (t, J=5.7 Hz, 1H), 7.95 (d, J=8.2 Hz, 2H), 7.58 (d, J=7.6 Hz, 2H), 7.54-7.52 (m, 2H), 7.49-7.47 (m, 3H), 7.38 (dd, J=4.7, 1.5 Hz, 1H), 7.33 (dd, J=8.2, 2.1 Hz, 1H), 7.26 (t, J=7.9 Hz, 2H), 7.01 (t, J=7.5 Hz, 1H), 6.78 (d, J=8.5 Hz, 1H), 4.99 (s, 2H), 4.06 (dd, J=8.5, 6.2 Hz, 1H), 3.54 (ddd, J=13.3, 8.5, 5.0 Hz, 1H), 3.47 (dt, J=12.9, 6.2 Hz, 1H), 1.76 (s, 3H). MS (ESI) calcd [M+H]+ 499.1, found 499.1.

Example 23

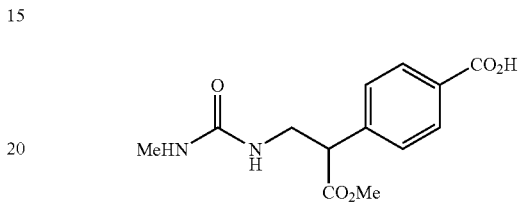

Step A: 4-[2-Methoxy-1-({[(methylamino)carbonyl]amino}methyl)-2-oxoethyl]benzoic acid. To a solution of tert-butyl 4-[2-methoxy-1-({[(methylamino)carbonyl]amino}methyl)-2-oxoethyl]benzoate (760 mg, 2.26 mmol) in CH2Cl2 (20 mL) was added trifluoroacetic acid (5 mL), and the reaction was stirred at room temperature for 2 h. The solution was evaporated to dryness to yield 4-[2-methoxy-1-({[(methylamino)carbonyl]amino}methyl)-2-oxoethyl]benzoic acid as an off-white powder that was carried on without further purification. MS (ESI) calcd [M+H]+281.1, found 281.1.

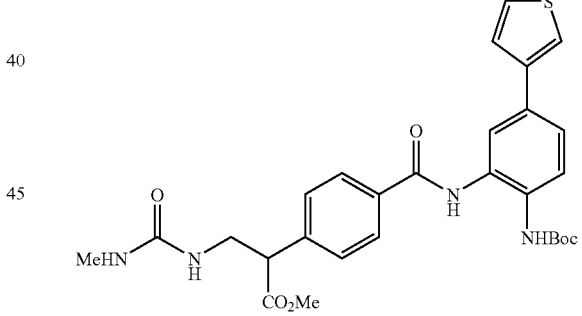

Step B: Methyl 2-[4-({[2-[(tert-butoxycarbonyl)amino]-5-(3-thienyl)phenyl]amino}carbonyl)phenyl]-3-{[(methylamino)carbonyl]amino}propanoate. 4-[2-Methoxy-1-({[(methylamino)carbonyl]amino}-methyl)-2-oxoethyl]benzoic acid (350 mg, 1.25 mmol), EDCI (312 mg, 1.63 mmol), and HOBT (220 mg, 1.63 mmol) were combined in DMF (15 mL) and stirred for 10 minutes before adding tert-butyl [2-amino-4-(3-thienyl)phenyl]carbamate (398 mg, 1.37 mmol). The reaction was then stirred at 55° C. for 24 h. The solvent was evaporated, and the resulting residue was dissolved in EtOAc, washed (water, brine), dried (MgSO$_4$), and concentrated. Flash chromatography on silica (0-5% MeOH/CH$_2$Cl$_2$) afforded methyl 2-[4-({[2-[(tert-butoxycarbonyl)amino]-5-(3-thienyl)phenyl]amino}carbonyl)phenyl]-3-{[(methylamino)carbonyl]amino}propanoate as a white solid. MS (ESI) calcd [M+H]$^+$ 553.2, found 553.2.

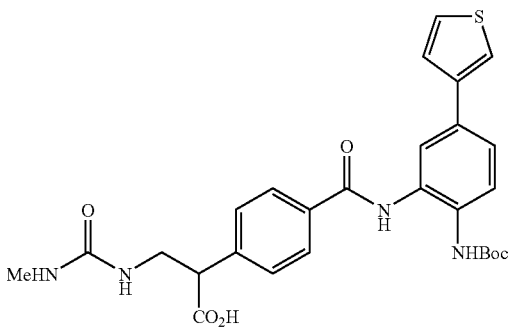

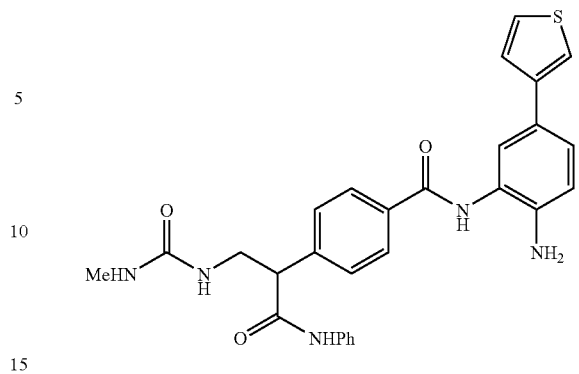

Step C: 2-[4-({[2-[(tert-Butoxycarbonyl)amino]-5-(3-thienyl)phenyl]amino}carbonyl)-phenyl]-3-{[(methylamino)carbonyl]amino}propanoic acid. To a solution of methyl 2-[4-({[2-[(tert-butoxycarbonyl)amino]-5-(3-thienyl)phenyl]amino}carbonyl)phenyl]-3-{[(methylamino)carbonyl]-amino}propanoate (420 mg, 0.76 mmol) in THF (4 mL) and MeOH (1.5 mL) was added KOH (1N, 0.91 mL, 0.91 mmol). After stirring at room temperature for 1 h, the mixture was diluted with 1 M citric acid and extracted with EtOAc. The organic layer was washed with water and brine, dried (MgSO$_4$), and concentrated to yield 2-[4-({[2-[(tert-butoxycarbonyl)amino]-5-(3-thienyl)phenyl]amino}carbonyl)-phenyl]-3-{[(methylamino)carbonyl]amino}propanoic acid as an off-white powder. MS (ESI) calcd [M+H]$^+$ 539.2, found 539.1.

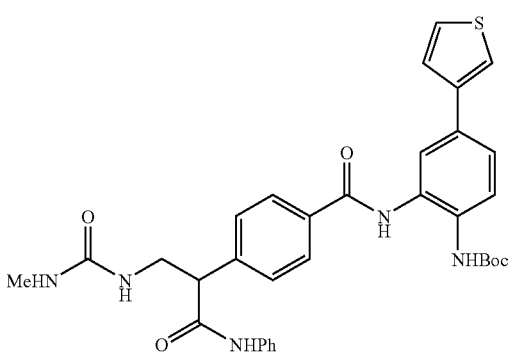

Step D: tert-Butyl [2-({4-[2-anilino-1-({[(methylamino)carbonyl]amino}methyl)-2-oxoethyl]-benzoyl}amino)-4-(3-thienyl)phenyl]carbamate. 2-[4-({[2-[(tert-Butoxycarbonyl)amino]-5-(3-thienyl)phenyl]amino}-carbonyl)phenyl]-3-{[(methylamino)carbonyl]amino}propanoic acid (104 mg, 0.19 mmol), EDCI (54 mg, 0.28 mmol), and HOBT (34 mg, 0.25 mmol) were combined in DMF (3 mL) and stirred for 10 minutes before adding aniline (26 µL, 0.28 mmol). The reaction was then stirred at room temperature for 2 h. The mixture was directly purified by reverse phase HPLC (45-95% MeCN/water) to give the title compound as a white solid. MS (ESI) calcd [M+H]$^+$ 614.2, found 614.1.

Step E: N-[2-Amino-5-(3-thienyl)phenyl]-4-[2-anilino-1-({[(methylamino)carbonyl]amino}methyl)-2-oxo-ethyl]benzamide. To a solution of tert-butyl [2-({4-[2-anilino-1-({[(methylamino)-carbonyl]-amino}methyl)-2-oxoethyl]benzoyl}amino)-4-(3-thienyl)phenyl]carbamate (49 mg, 0.08 mmol) in CH$_2$Cl$_2$ (4 mL) was added trifluoroacetic acid (1 mL), and the reaction was stirred at room temperature for 3 h. Concentration yielded a yellow residue that was dissolved in EtOAc, neutralized with sat. NaHCO$_3$, washed with brine, dried (MgSO$_4$), and evaporated to give N-[2-amino-5-(3-thienyl)-phenyl]-4-[2-anilino-1-({[(methylamino)carbonyl]amino}methyl)-2-oxoethyl]benzamide as a white solid. $^1$H NMR (DMSO-d$_6$) δ 10.19 (s, 1H), 9.66 (s, 1H), 7.95 (d, J=8.2 Hz, 2H), 7.58 (d, J=7.6 Hz, 2H), 7.54-7.52 (m, 2H), 7.49-7.47 (m, 3H), 7.38 (dd, J=4.8, 1.3 Hz, 1H), 7.33 (dd, J=8.2, 2.1 Hz, 1H), 7.26 (t, J=7.9 Hz, 2H), 7.01 (t, J=7.5 Hz, 1H), 6.78 (d, J=8.5 Hz, 1H), 6.08 (t, J=6.0 Hz, 1H), 5.77 (q, J=4.4 Hz, 1H), 5.00 (s, 2H), 4.01 (dd, J=9.1, 5.6 Hz, 1H), 3.52 (ddd, J=13.5, 8.8, 5.0 Hz, 1H), 3.42 (dt, J=12.8, 6.4 Hz, 1H), 2.51 (d, J=4.7 Hz, 3H). MS (ESI) calcd [M+H]$^+$ 514.1, found 514.1.

Example 24

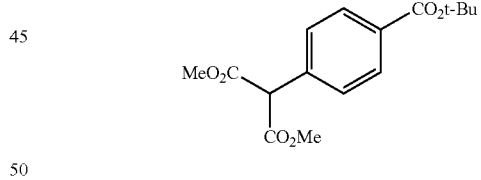

Step A; Dimethyl [4-(tert-butoxycarbonyl)phenyl]malonate. To a mixture of K$_3$PO$_4$ (12.74 g, 60.0 mmol), dimethyl malonate (2.91 g, 22.0 mmol), and tert-butyl 4-bromobenzoate (5.14 g, 20.0 mmol) were added Pd(dba)$_2$ (575 mg, 1.00 mmol), toluene (60 mL), and P(t-Bu)$_3$ (10% wt in hexanes, 11.56 mL, 3.89 mmol). After degassing for 20 minutes, the reaction was stirred at 80° C. for 16 h. The resulting mixture was diluted with EtOAc, washed with H$_2$O and brine, dried (MgSO$_4$), and concentrated. Flash chromatography on silica gel (0-25% EtOAc/hexanes) gave dimethyl [4-(tert-butoxycarbonyl)phenyl]malonate as a white solid. $^1$H NMR (CDCl$_3$) δ 7.97 (d, J=8.5 Hz, 2H), 7.44 (d, J=8.5 Hz, 2H), 4.69 (s, 1H), 3.75 (s, 6H), 1.57 (s, 9H). MS (ESI) calcd [M+Na]$^+$ 331.1, found 331.1.

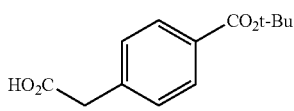

Step B: [4-(tert-Butoxycarbonyl)phenyl]acetic acid. To a solution of dimethyl [4-(tert-butoxycarbonyl)phenyl]malonate (4.00 g, 13.0 mmol) in THF (30 mL) and MeOH (10 mL) was added NaOH (2N, 19.5 mL, 38.9 mmol). After stirring the reaction for 45 minutes at room temperature, it was diluted with 1 M citric acid and extracted with EtOAc. The organic layer was washed (water, brine), dried (MgSO$_4$), and concentrated to a yellow residue. The residue was redissolved in EtOAc (50 mL) and H$_2$O (50 mL) and stirred for 2 h at 80° C. The mixture was extracted with EtOAc, washed with water and brine, dried (MgSO$_4$), and concentrated to give [4-tert-butoxycarbonyl)phenyl]acetic acid as an off-white solid. MS (ESI) calcd [M+Na]$^+$ 259.1, found 259.1.

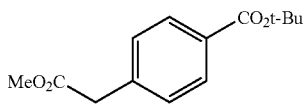

Step C: tert-Butyl 4-(2-methoxy-2-oxoethyl)benzoate. [4-(tert-Butoxycarbonyl)phenyl]acetic acid (2.94 g, 12.4 mmol) and DMAP (152 mg, 1.24 mmol) were dissolved in CH$_2$Cl$_2$ (50 mL) and cooled to 0° C. EDCI (3.10 g, 16.2 mmol) and MeOH (660 µL, 16.2 mmol) were added. After stirring for 30 min at 0° C., the reaction was allowed to warm to room temperature and stirred 2 h. The mixture was then diluted with CH$_2$Cl$_2$, washed (sat. NaHCO$_3$, brine), dried (MgSO$_4$), and concentrated. Flash chromatography on silica gel (0-10% EtOAc/hexanes) afforded tert-butyl 4-(2-methoxy-2-oxoethyl)benzoate as a colorless oil. $^1$H NMR (CDCl$_3$) δ 7.93 (d, J=8.2 Hz, 2H), 7.31 (d, J=8.5 Hz, 2H), 3.68 (s, 3H), 3.66 (s, 2H), 1.57 (s, 9H). MS (ESI) calcd [M+Na]$^+$ 273.1, found 273.1.

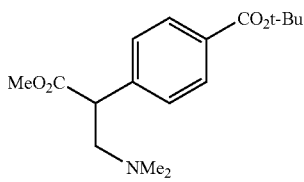

Step D: tert-Butyl 4-{1-[(dimethylamino)methyl]-2-methoxy-2-oxoethyl}benzoate. A solution of tert-butyl 4-(2-methoxy-2-oxoethyl)benzoate (800 mg, 3.20 mmol) in THF (15 mL) was cooled to −78° C. before adding lithium hexamethyldisilazide (1M in THF, 4.16 mL, 4.16 mmol) dropwise. After 15 minutes, Eschenmoser's salt (1.18 g, 6.40 mmol) was added in one portion. The reaction was stirred at −78° C. for 5 minutes, warmed to room temperature, and stirred an additional 1 h. The mixture was diluted with water and extracted with EtOAc. The organic layer was then extracted with 1N HCl. The acidic aqueous layer was neutralized with sat. NaHCO$_3$ and extracted with EtOAc. The new organic extracts were dried over MgSO$_4$ and evaporated to yield tert-butyl 4-{1-[(dimethylamino)methyl]-2-methoxy-2-oxoethyl}benzoate as a white solid. $^1$H NMR (CDCl$_3$) δ 7.91 (d, J=8.5 Hz, 2H), 7.35 (d, J=8.2 Hz, 2H), 3.84 (dd, J=9.7, 5.6 Hz, 1H), 3.65 (s, 3H), 3.10 (dd, J=12.3, 9.7 Hz, 1H), 2.47 (dd, J=12.3, 5.6 Hz, 1H), 2.24 (s, 6H), 1.55 (s, 9H). MS (ESI) calcd [M+H]$^+$ 308.1, found 308.1.

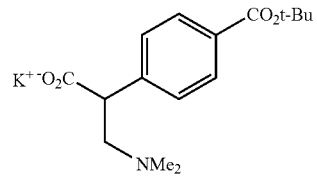

Step E: Potassium 2-[4-(tert-butoxycarbonyl)phenyl]-3-(dimethylamino)propanoate. To a solution of tert-butyl 4-{1-[(dimethylamino)methyl]-2-methoxy-2-oxoethyl}benzoate (859 mg, 2.79 mmol) in THF (9 mL) and MeOH (3 mL) was added KOH (1N, 2.93 mL, 2.93 mmol). The reaction was stirred at room temperature for 30 minutes. An additional 100 µL of 1N KOH was added, and the solution was stirred for another 30 minutes. Concentration of the reaction mixture to dryness yielded potassium 2-[4-(tert-butoxycarbonyl)phenyl]-3-(dimethylamino)propanoate as a white solid that was carried on without purification. MS (EST) calcd [M+H]$^+$ 294.1, found 294.1.

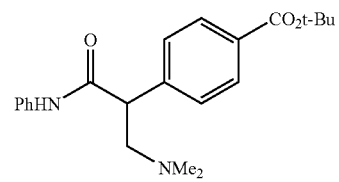

Step F: tert-Butyl 4-{2-anilino-1-[(dimethylamino)methyl]-2-oxoethyl}benzoate. Crude potassium 2-[4-(tert-butoxycarbonyl)phenyl]-3-(dimethylamino)propanoate (925 mg, ~2.79 mmol), EDCI (803 mg, 4.19 mmol), and HOBT (491 mg, 3.63 mg) were combined in DMF (15 mL) and stirred for 5 minutes before adding aniline (331 µL, 3.63 mmol). The reaction was stirred at room temperature for 3 h. Additional EDCI (200 mg) was added, and the reaction was stirred for another 3 h. The mixture was concentrated and purified by reverse phase HPLC (50-95% MeCN/water). The resulting residue was dissolved in EtOAc, neutralized with sat. NaHCO$_3$, washed with brine, dried (MgSO$_4$), and concentrated to give tert-butyl 4-{2-anilino-1-[(dimethylamino)methyl]-2-oxoethyl}benzoate as a white solid. $^1$H NMR (CDCl$_3$) δ 7.97 (d, J=8.5 Hz, 2H), 7.33 (d, J=8.5 Hz, 2H), 7.21 (dd, J=8.5, 7.3 Hz, 2H), 6.77 (t, J=7.3 Hz, 1H), 6.72 (d, J=7.9 Hz, 2H), 4.22 (dd, J=8.8, 5.0 Hz, 1H), 3.80 (dd, J=13.8, 9.1 Hz, 1H), 3.40 (dd, J=13.6, 4.8 Hz, 1H), 2.95 (s, 3H), 2.74 (s, 3H), 1.58 (s, 9H). MS (ESI) calcd [M+H]$^+$ 369.2, found 369.2.

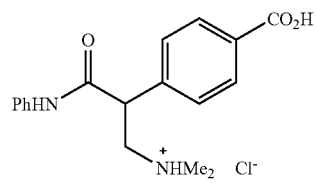

Step G: 4-{2-Anilino-1-[(dimethylamino)methyl]-2-oxoethyl}benzoic acid hydrochloride. tert-Butyl 4-{2- anilino-1-[(dimethylamino)methyl]-2-oxoethyl}benzoate (350 mg, 0.95 mmol) was taken up in 4 M HCl/dioxane (10 mL) and stirred at room temperature for 16 h. The solution was concentrated to dryness to give 4-{2-anilino-1-[(dimethylamino)methyl]-2-oxoethyl}benzoic acid hydrochloride as a white, flaky solid. MS (ESI) calcd [M+H]$^+$ 313.1, found 313.1.

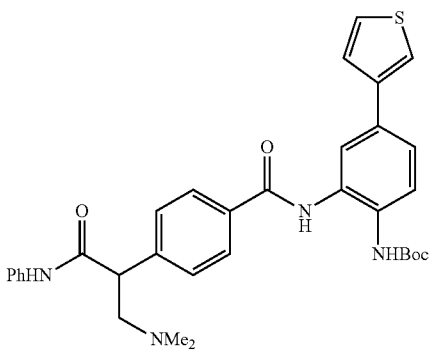

Step H: tert-Butyl [2-[(4-{2-anilino-1-[(dimethylamino)methyl]-2-oxoethyl}benzoyl)amino]-4-(3-thienyl)-phenyl]carbamate. Crude 4-{2-anilino-1-[(dimethylamino)methyl]-2-oxoethyl}benzoic acid hydrochloride (331 mg, ~0.95 mmol), EDCI (364 mg, 1.90 mmol), and HOBT (168 mg, 1.24 mmol) were combined in DMF (10 mL) and stirred for 5 minutes before adding tert-butyl [2-amino-4-(3-thienyl)phenyl]carbamate (303 mg, 1.05 mmol). The reaction was stirred at room temperature for 48 h. Additional tert-butyl [2-amino-4-(3-thienyl)phenyl]carbamate (80 mg) was added, and the reaction was stirred for another 24 h at room temperature. The mixture was directly purified by reverse phase HPLC (50-95% MeCN/water) to give the trifluoroacetic acid salt of the title compound as a yellow solid. MS (ESI) calcd [M+H]$^+$ 585.2, found 585.1.

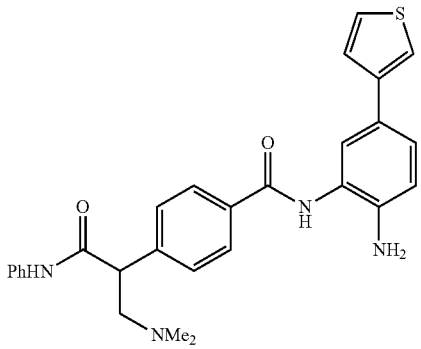

Step I: N-[2-Amino-5-(3-thienyl)phenyl]-4-{2-anilino-1-[(dimethylamino)methyl]-2-oxoethyl}benzamide. To a solution of the trifluoroacetic acid salt of tert-butyl [2-[(4-{2-anilino-1-[(dimethylamino)methyl]-2-oxoethyl}benzoyl)amino]-4-(3-thienyl)phenyl]carbamate (374 mg, 0.54 mmol) in CH$_2$Cl$_2$ (8 mL) was added trifluoroacetic acid (2 mL), and the reaction was stirred at room temperature for 1 h. Concentration yielded a yellow residue that was purified by reverse phase HPLC (10-70% MeCN/water). The resulting solid was dissolved in CH$_2$Cl$_2$ (with a small amount of MeOH), neutralized with sat. NaHCO$_3$, washed with brine, dried (MgSO$_4$), and evaporated to yield N-[2-amino-5-(3-thienyl)phenyl]-4-{2-anilino-1-[(dimethylamino)methyl]-2-oxoethyl}benzamide as an off-white solid.

$^1$H NMR (DMSO-d$_6$) δ 9.69 (s, 1H), 7.96 (d, J=8.2 Hz, 2H), 7.54-7.52 (m, 2H), 7.48-7.45 (m, 3H), 7.39 (dd, J=4.4, 1.8 Hz, 1H), 7.33 (dd, J=8.5, 2.1 Hz, 1H), 7.05 (dd, J=8.5, 7.3 Hz, 2H), 6.79 (d, J=8.2 Hz, 1H), 6.58 (d, J=7.6 Hz, 2H), 6.51 (t, J=7.2 Hz, 1H), 5.54 (t, J=6.2 Hz, 1H), 5.01 (s, 2H), 4.28 (dd, J=8.2, 5.6 Hz, 1H), 3.66 (ddd, J=13.2, 8.1, 5.4 Hz, 1H), 3.18 (dt, J=12.5, 6.2 Hz, 1H), 2.85 (s, 3H), 2.83 (s, 3H). MS (ESI) calcd [M+H]$^+$ 485.2, found 485.1.

The compounds described in the following table were prepared by methods analogous to those synthetic methods described above, but using the appropriate starting reagents.

| Cpd # | | Name | Form | MS |
|---|---|---|---|---|
| 24-2 | | 4-{1-[(acetylamino)methyl]-2-anilino-2-oxoethyl}-N-[2-amino-5-(3-thienyl)phenyl]benzamide | free base; TFA salt | calcd [M + H]$^+$ 499.1, found 499.1 |

| Cpd # | | Name | Form | MS |
|---|---|---|---|---|
| 24-3 | 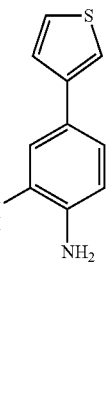 | 4-[1-[(acetylamino)methyl]-2-(methylamino)-2-oxoethyl]-N-[2-amino-5-(3-thienyl)phenyl]benzamide | TFA salt | calcd [M + H]$^+$ 437.1, found 437.1 |
| 24-4 | 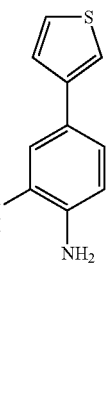 | 4-[1-[(acetylamino)methyl]-2-(dimethylamino)-2-oxoethyl]-N-[2-amino-5-(3-thienyl)phenyl]benzamide | TFA salt | calcd [M + H]$^+$ 451.1, found 451.1 |
| 24-5 | 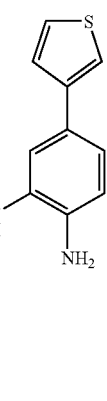 | 4-{1-[(acetylamino)methyl]-2-morpholin-4-yl-2-oxoethyl}-N-[2-amino-5-(3-thienyl)phenyl]benzamide | free base | calcd [M + H]$^+$ 493.1, found 493.1 |

| Cpd # | | Name | Form | MS |
|---|---|---|---|---|
| 24-6 | 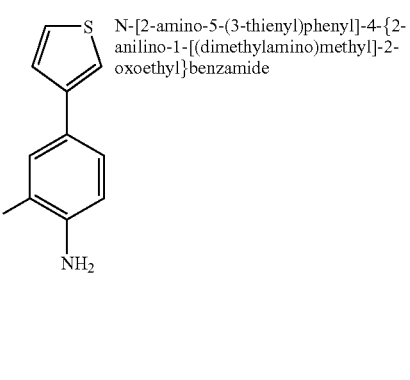 | N-[2-amino-5-(3-thienyl)phenyl]-4-{2-anilino-1-[(dimethylamino)methyl]-2-oxoethyl}benzamide | free base; bis-TFA salt | calcd [M + H]+ 485.2, found 485.1 |
| 24-7 | 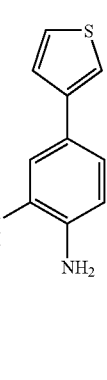 | N-[2-amino-5-(3-thienyl)phenyl]-4-[1-[(dimethylamino)methyl]-2-(methylamino)-2-oxoethyl]benzamide | free base; bis-TFA salt | calcd [M + H]+ 423.1, found 423.1 |
| 24-8 | 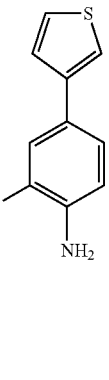 | N-[2-amino-5-(3-thienyl)phenyl]-4-(2-anilino-1-{[(methylsulfonyl)amino]methyl}-2-oxoethyl)benzamide | TFA salt | calcd [M + H]+ 535.1, found 535.0 |

-continued

| Cpd # | | Name | Form | MS |
|---|---|---|---|---|
| 24-9 | 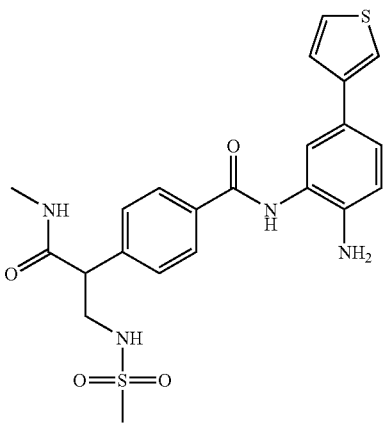 | N-[2-amino-5-(3-thienyl)phenyl]-4-(2-(methylamino)-1-{[(methylsulfonyl)amino]methyl}-2-oxoethyl)benzamide | TFA salt | calcd [M + H]$^+$ 473.1, found 473.1 |
| 24-10 | 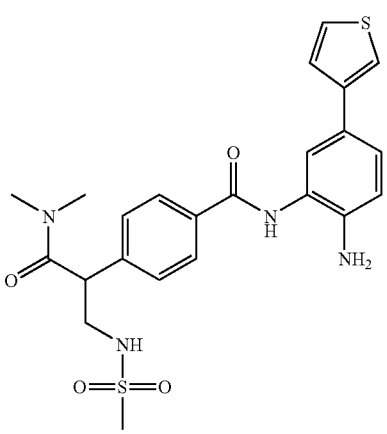 | N-[2-amino-5-(3-thienyl)phenyl]-4-(2-(dimethylamino)-1-{[(methylsulfonyl)amino]methyl}-2-oxoethyl)benzamide | TFA salt | calcd [M + H]$^+$ 487.1, found 487.1 |
| 24-11 | 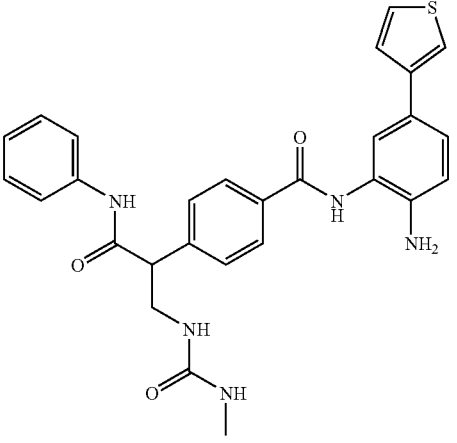 | N-[2-amino-5-(3-thienyl)phenyl]-4-[2-anilino-1-({[(methylamino)carbonyl]amino}methyl)-2-oxoethyl]benzamide | free base | calcd [M + H]$^+$ 514.1, found 514.1 |

| Cpd # | Name | Form | MS |
|---|---|---|---|
| 24-12 | N-[2-amino-5-(3-thienyl)phenyl]-4-[2-(methylamino)-1-({[(methylamino)carbonyl]amino}methyl)-2-oxoethyl)benzamide | free base | calcd [M + H]+ 452.1, found 452.1 |
| 24-13 | N-[2-amino-5-(3-thienyl)phenyl]-4-[2-(dimethylamino)-1-({[(methylamino)carbonyl]amino}methyl)-2-oxoethyl)benzamide | free base | calcd [M + H]+ 466.1, found 466.1 |

Example 25

HDAC Inhibition by Novel Compounds—HDAC1—Flag Assay

Novel compounds were tested for their ability to inhibit histone deacetylase, subtype 1 (HDAC1) using an in vitro deacetylation assay. The enzyme source for this assay was an epitope-tagged human HDAC1 complex immuno-purified from stably expressing mammalian cells. The substrate consisted of a commercial product containing an acetylated lysine side chain (BIOMOL Research Laboratories, Inc., Plymouth Meeting, Pa.). Upon deacetylation of the substrate by incubation with the purified HDAC1 complex, a fluorophore is produced that is directly proportional to the level of deacetylation. Using a substrate concentration at the Km for the enzyme preparation, the deacetylation assay was performed in the presence of increasing concentrations of novel compounds to semi-quantitatively determine the concentration of compound required for 50% inhibition (IC50) of the deacetylation reaction. The compounds of the instant invention described in the Examples and Tables above exhibit histone deacetylase inhibitory activity at concentrations of less than about 5 µM.

Example 26

HDAC Inhibition in Cell Lines—ATP Assay

The novel compounds of the present invention were tested for their ability to inhibit proliferation of the human cervical cancer (HeLa) and colon carcinoma (HCT116) cells.

In this assay, also referred to as the Vialight Assay, cellular ATP levels are measured as a means of quantifying cellular proliferation. This assay makes use of a bioluminescent method from Cambrex (ViaLight PLUS, cat. #LT07-121). In the presence of ATP, luciferase converts luciferin to oxyluciferin and light. The amount of light produced (emission at 565 nM) is measured and correlates with a relative amount of proliferation. Human cervical cancer (HeLa) or colon carcinoma (HCT116) cells were incubated with vehicle or increasing concentrations of compound for 48, 72 or 96 hours. Cell proliferation was quantified by adding the cell lysis reagent (provided in the Vialight assay kit) directly to culture wells, followed by addition of the ATP-monitoring reagent (containing luciferase/luciferin). The amount of light produced is then measured (emission at 565 nM). The quantity of light produced, as measured by 565 nM absorbance, is directly proportional to the number of living cells in culture.

While this invention has been particularly shown and described with references to embodiments thereof, it will be understood by those skilled in the art that various changes in form and details may be made therein without departing from the meaning of the invention described. Rather, the scope of the invention is defined by the claims that follow.

What is claimed is:

1. A compound represented by Formula I:

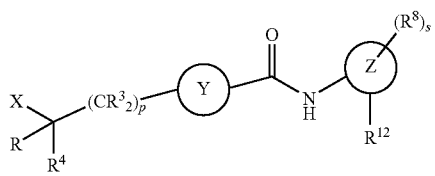

I wherein

X is 1) —$(CR^2_2)_nC(O)OR^1$,
2) —$(CR^2_2)_nC(O)NR^1_2$,
3) —$(CR^2_2)_nC(O)R^1$,
4) —$(CR^2_2)_nOC(O)NR^1_2$,
5) —$(CR^2_2)_n$aryl, wherein aryl is optionally substituted with one or more substituents,
6) —$(CR^2_2)_nC(O)NR^1(CR^2_2)_mNR^1_2$,
7) —$(CR^2_2)_nC(O)NR^1(CR^2_2)_mNR^1C(O)R^1$,
8) —$(CR^2_2)_nC(O)NR^1(CR^2_2)_nOR^1$, or
9) —$(CR^2_2)_nC(O)NR^1(CR^2_2)_nC(O)NR^1_2$;

Y is unsubstituted or substituted aryl or unsubstituted or substituted thienyl or pyridinyl;

Z is aryl or heteroaryl;

R is H or unsubstituted or substituted $C_1$-$C_6$ alkyl;

$R^1$ is independently selected from H, $C_1$-$C_6$ alkyl, —$(CR^2_2)_n$aryl, and —$(CR^2_2)_n$heterocyclyl; wherein said alkyl, aryl or heterocyclyl is optionally substituted with one or more substituents;

$R^2$ and $R^3$ are independently selected from H, unsubstituted or substituted $C_1$-$C_6$ alkyl, and $(CR^2_2)_n$aryl;

$R^4$ is
1) —$(CR^2_2)_nNR^5_2$,
2) —$(CR^2_2)_nNR^5C(O)R^5$,
3) —$(CR^2_2)_nNR^5C(O)OR^5$,
4) —$(CR^2_2)_n$heterocyclyl,
5) —$(CR^2_2)_nNR^5S(O)_2R^5$, or
6) —$(CR^2_2)_nNR^5C(O)NR^5_2$;
wherein heterocyclyl is optionally substituted with one or more substituents;

optionally, when R is unsubstituted or substituted $C_1$-$C_6$ alkyl and $R^4$ is not —$(CR^2_2)_n$heterocyclyl, R and $R^4$ may be cyclized to form a ring system;

$R^5$ is independently selected from H, $C_1$-$C_6$ alkyl, —$(CR^2_2)_n$aryl, and —$(CR^2_2)_n$heterocyclyl, wherein alkyl, aryl or heterocyclyl may be optionally substituted with one or more substituents;

$R^8$ is unsubstituted or substituted aryl or unsubstituted or substituted heteroaryl;

$R^{12}$ is $NH_2$, $NR^5C(O)R^5$, $NR^5C(O)OR^5$, OH, or NH-Boc;

m is 1, 2 or 3;

n is independently 0, 1, 2, 3 or 4;

p is 0, 1, 2, 3, or 4;

s is 0, 1 or 2;

or a stereoisomer or a pharmaceutically acceptable salt thereof.

2. The compound according to claim 1, wherein

Y is phenyl, thienyl, or pyridinyl, wherein phenyl, thienyl or pyridinyl is optionally substituted with one or two substituents selected from $R^7$;

Z is phenyl, pyrazolyl, thienyl or pyridinyl;

$R^2$ and $R^3$ are independently selected from H and unsubstituted or substituted $C_1$-$C_6$ alkyl;

$R^7$ is independently selected from unsubstituted or substituted $C_1$-$C_6$ alkyl, $OR^5$, —$(CR^2_2)_n$aryl, CN, $CF_3$ and halo;

or a stereoisomer or a pharmaceutically acceptable salt thereof.

3. The compound according to claim 1, represented by Formula II

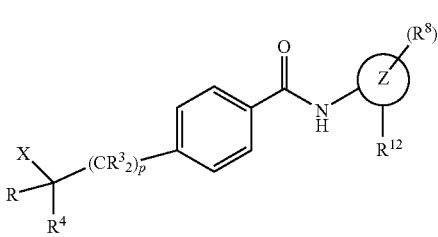

II wherein

X is 1) —$(CR^2_2)_nC(O)OR^1$,
2) —$(CR^2_2)_nC(O)NR^1_2$,
3) —$(CR^2_2)_nC(O)R^1$,
4) —$(CR^2_2)_nOC(O)NR^1_2$,
5) —$(CR^2_2)_n$aryl, wherein aryl is optionally substituted with one to three substituent selected from $R^7$,
6) —$(CR^2_2)_nC(O)NR^1(CR^2_2)_mNR^1_2$,
7) —$(CR^2_2)_nC(O)NR^1(CR^2_2)_mNR^1C(O)R^1$,
8) —$(CR^2_2)_nC(O)NR^1(CR^2_2)_nOR^1$, or
9) —$(CR^2_2)_nC(O)NR^1(CR^2_2)_nC(O)NR^1_2$;

Z is phenyl or pyrazolyl;

R is H or unsubstituted or substituted $C_1$-$C_6$ alkyl;

$R^1$ is independently selected from H, $C_1$-$C_6$ alkyl, —$(CR^2_2)_n$aryl, and —$(CR^2_2)_n$heterocyclyl; wherein said alkyl, aryl or heterocyclyl is optionally substituted with one to three substituent selected from $R^7$;

$R^2$ and $R^3$ are independently selected from H, unsubstituted or substituted $C_1$-$C_6$ alkyl, and $(CR^2_2)_n$aryl;

$R^4$ is
1) —$(CR^2_2)_nNR^5_2$,
2) —$(CR^2_2)_nNR^5C(O)R^5$,
3) —$(CR^2_2)_nNR^5C(O)OR^5$,
4) —$(CR^2_2)_n$heterocyclyl,
5) —$(CR^2_2)_nNR^5S(O)_2R^5$, or
6) —$(CR^2_2)_nNR^5C(O)NR^5_2$;
wherein heterocyclyl is optionally substituted with one to three substituent selected from $R^7$;

$R^5$ is independently selected from H, $C_1$-$C_6$ alkyl, —$(CR^2_2)_n$aryl, and —$(CR^2_2)_n$heterocyclyl, wherein alkyl, aryl or heterocyclyl may be optionally substituted with one to three substituent selected from $R^7$;

$R^7$ is independently selected from unsubstituted or substituted $C_1$-$C_6$ alkyl, $OR^5$, —$(CR^2_2)_n$aryl, CN, $CF_3$ and halo;

$R^8$ is unsubstituted or substituted phenyl or unsubstituted or substituted thienyl;

$R^{12}$ is $NH_2$, OH, or NH-Boc;

m is 1, 2 or 3;

n is independently 0, 1, 2, 3 or 4;

p is 0, 1, 2, or 3;

s is 0, or 1;

or a stereoisomer or a pharmaceutically acceptable salt thereof.

4. The compound according to claim 1, represented by Formula III

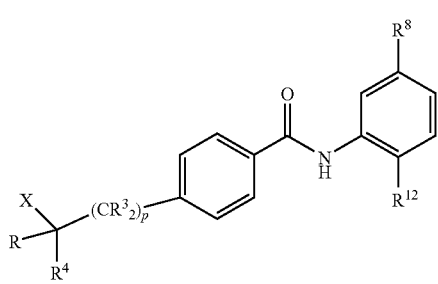

wherein
X is 1) —(CR²₂)ₙC(O)OR¹,
2) —(CR²₂)ₙC(O)NR¹₂,
3) —(CR²₂)ₙC(O)R⁵, or
4) —(CR²₂)ₙaryl, wherein aryl is optionally substituted with one to three substituent selected from R⁷;
R is H or unsubstituted or substituted C₁-C₆ alkyl;
R¹ is independently selected from H, C₁-C₆ alkyl, —(CR²₂)ₙaryl, and —(CR²₂)ₙheterocyclyl;
wherein said alkyl, aryl or heterocyclyl is optionally substituted with one to three substituent selected from R⁷;
R² and R³ are independently selected from H, unsubstituted or substituted C₁-C₆ alkyl, and (CR²₂)ₙaryl;
R⁴ is
1) —(CR²₂)ₙNR⁵₂,
2) —(CR²₂)ₙNR⁵C(O)R⁵,
3) —(CR²₂)ₙNR⁵C(O)OR⁵,
4) —(CR²₂)ₙheterocyclyl,
5) —(CR²₂)ₙNR⁵S(O)₂R⁵, or
6) —(CR²₂)ₙNR⁵C(O)NR⁵₂;
wherein heterocyclyl is optionally substituted with one to three substituent selected from R⁷;
R⁵ is independently selected from H, C₁-C₆ alkyl, —(CR²₂)ₙaryl, and —(CR²₂)ₙheterocyclyl, wherein alkyl, aryl or heterocyclyl may be optionally substituted with one to three substituent selected from R⁷;
R⁷ is independently selected from unsubstituted or substituted C₁-C₆ alkyl, OR⁵, —(CR²₂)ₙaryl, CN, CF₃ and halo;
R⁸ is phenyl or thienyl;
R¹² is NH₂;
n is independently 0, 1, 2, 3 or 4;
p is 0, 1, 2, or 3;
or a stereoisomer or a pharmaceutically acceptable salt thereof.

5. The compound of claim 1 selected from
amino[4-({[2-amino-5-(2-thienyl)phenyl]amino}carbonyl)phenyl]acetic acid;
ethyl amino[4-({[2-amino-5-(2-thienyl)phenyl]amino}carbonyl)phenyl]acetate;
4-[1-amino-2-(methylamino)-2-oxoethyl]-N-[2-amino-5-(2-thienyl)phenyl]benzamide;
N-[2-amino-5-(2-thienyl)phenyl]-4-(1,2-diamino-2-oxoethyl)benzamide;
4-{1-amino-2-oxo-2-[(2,2,2-trifluoroethyl)amino]ethyl}-N-[2-amino-5-(2-thienyl)phenyl]benzamide;
4-{1-amino-2-[(2-methoxyphenyl)amino]-2-oxoethyl}-N-(4-amino-1-phenyl-1H-pyrazol-3-yl)benzamide;
4-[1-amino-2-(isoxazol-3-ylamino)-2-oxoethyl]-N-(4-amino-1-phenyl-1H-pyrazol-3-yl)benzamide;
4-[1-amino-2-oxo-2-(pyridin-2-ylamino)ethyl]-N-(4-amino-1-phenyl-1H-pyrazol-3-yl)benzamide;
4-{1-amino-2-[(4-methyl-1,3-thiazol-2-yl)amino]-2-oxoethyl}-N-(4-amino-1-phenyl-1H-pyrazol-3-yl)benzamide;
4-{1-amino-2-[(3-methoxyphenyl)amino]-2-oxoethyl}-N-(4-amino-1-phenyl-1H-pyrazol-3-yl)benzamide;
4-{1-amino-2-[(4-cyanopyridin-2-yl)amino]-2-oxoethyl}-N-(4-amino-1-phenyl-1H-pyrazol-3-yl)benzamide;
4-[1-amino-2-(2,3-dihydro-1,4-benzodioxin-6-ylamino)-2-oxoethyl]-N-(4-amino-1-phenyl-1H-pyrazol-3-yl)benzamide;
ethyl [4-({[2-amino-5-(2-thienyl)phenyl]amino}carbonyl)phenyl]{[(pyridin-3-ylmethoxy)carbonyl]amino}acetate;
[4-({[2-amino-5-(2-thienyl)phenyl]amino}carbonyl)phenyl]{[(pyridin-3-ylmethoxy)carbonyl]amino}acetic acid;
pyridin-3-ylmethyl [1-[4-({[2-amino-5-(2-thienyl)phenyl]amino}carbonyl)phenyl]-2-(methylamino)-2-oxoethyl]carbamate;
pyridin-3-ylmethyl {2-amino-1-[4-({[2-amino-5-(2-thienyl)phenyl]amino} carbonyl)phenyl]-2-oxoethyl}carbamate;
pyridin-3-ylmethyl [1-[4-({[2-amino-5-(2-thienyl)phenyl]amino}carbonyl)phenyl]-2-(ethylamino)-2-oxoethyl]carbamate;
pyridin-3-ylmethyl [1-[4-({[2-amino-5-(2-thienyl)phenyl]amino}carbonyl)phenyl]-2-(isopropylamino)-2-oxoethyl]carbamate;
pyridin-3-ylmethyl [1-[4-({[2-amino-5-(2-thienyl)phenyl]amino}carbonyl)phenyl]-2-(dimethylamino)-2-oxoethyl]carbamate;
(acetylamino)[4-({[2-amino-5-(2-thienyl)phenyl]amino}carbonyl)phenyl]acetic acid;
4-[1-(acetylamino)-2-oxo-2-pyrrolidin-1-ylethyl]-N-[2-amino-5-(2-thienyl)phenyl]benzamide;
4-[1-(acetylamino)-2-amino-2-oxoethyl]-N-[2-amino-5-(2-thienyl)phenyl]benzamide;
4-[1-(acetylamino)-2-(methylamino)-2-oxoethyl]-N-[2-amino-5-(2-thienyl)phenyl]benzamide;
4-[1-(acetylamino)-2-(dimethylamino)-2-oxoethyl]-N-[2-amino-5-(2-thienyl)phenyl]benzamide;
4-[1-(acetylamino)-2-(isopropylamino)-2-oxoethyl]-N-[2-amino-5-(2-thienyl)phenyl]benzamide;
4-[1-(acetylamino)-2-(ethylamino)-2-oxoethyl]-N-[2-amino-5-(2-thienyl)phenyl]benzamide;
Tert-butyl [2-({4-[1-(acetylamino)-2-(methylamino)-2-oxoethyl]benzoyl}amino)-4-(2-thienyl)phenyl]carbamate;
N-[2-amino-5-(2-thienyl)phenyl]-4-[2-(methylamino)-2-oxo-1-pyrrolidin-1-ylethyl]benzamide;
[4-({[2-amino-5-(2-thienyl)phenyl] amino}carbonyl)phenyl](pyrrolidin-1-yl)acetic acid;
N-[2-amino-5-(2-thienyl)phenyl]-4-[2-(isopropylamino)-1-(4-methylpiperidin-1-yl)-2-oxoethyl]benzamide;
N-(2-amino-5-thien-2-ylphenyl)-4-{1-azetidin-1-yl-2-[(4-methylphenyl)amino]-2-oxoethyl}benzamide;
N-(2-amino-5-thien-2-ylphenyl)-4-[1-(diethylamino)-2-(isopropylamino)-2-oxoethyl]benzamide;
N-(2-amino-5-thien-2-ylphenyl)-4-[1-azetidin-1-yl-2-(isopropylamino)-2-oxoethyl]benzamide;

N-(2-amino-5-thien-3-ylphenyl)-5-[2-[(4-chlorophenyl)amino]-1-(4-methylpiperazin-1-yl)-2-oxoethyl]thiophene-2-carboxamide;
N-(2-amino-5-thien-2-ylphenyl)-5-[2-[(4-chlorophenyl)amino]-1-(4-methylpiperazin-1-yl)-2-oxoethyl]thiophene-2-carboxamide;
N-(2-aminophenyl)-4-[1-(benzoylamino)-2-(benzylamino)-2-oxoethyl]benzamide;
N-(2-aminophenyl)-4-[1,2-bis(benzylamino)-2-oxoethyl]benzamide;
N-(2-aminophenyl)-4-{2-(benzylamino)-2-oxo-1-[(2-phenylethyl)amino]ethyl Benzamide;
N-(2-aminophenyl)-4-{1-(benzoylamino)-2-[(4-chlorophenyl)amino]-2-oxoethyl}benzamide;
N-(2-aminophenyl)-4-{2-[(4-chlorophenyl)amino]-2-oxo-1-[(phenylacetyl)amino]ethyl}benzamide;
N-(2-aminophenyl)-4-{2-[(4-chlorophenyl)amino]-2-oxo-1-[(3-phenylpropanoyl)amino]ethyl}benzamide;
N-(2-aminophenyl)-4-{1-(benzoylamino)-2-[(4-methylphenyl)amino]-2-oxoethyl}benzamide;
N-(2-aminophenyl)-4-[1-(benzoylamino)-2-(2-naphthylamino)-2-oxoethyl]benzamide;
N-(2-aminophenyl)-4-{2-[(4-methylphenyl)amino]-2-oxo-1-[(phenylacetyl)amino]ethyl}benzamide;
N-(2-aminophenyl)-4-{2-[(4-methoxyphenyl)amino]-2-oxo-1-[(phenylacetyl)amino]ethyl}benzamide;
N-(2-aminophenyl)-4-{2-(2-naphthylamino)-2-oxo-1-[(phenylacetyl)amino]ethyl}benzamide;
N-(2-aminophenyl)-4-{2-[(4-methylphenyl)amino]-2-oxo-1-[(3-phenylpropanoyl)amino]ethyl}benzamide;
N-(2-aminophenyl)-4-{2-[(4-methoxyphenyl)amino]-2-oxo-1-[(3-phenylpropanoyl)amino]ethyl}benzamide;
N-(2-aminophenyl)-4-{2-(2-naphthylamino)-2-oxo-1-[(3-phenylpropanoyl)amino]ethyl}benzamide;
N-(2-aminophenyl)-4-[2-(benzylamino)-1-(4-methylpiperazin-1-yl)-2-oxoethyl]-benzamide;
N-(2-aminophenyl)-4-[2-[(4-chlorophenyl)amino]-1-(4-ethylpiperazin-1-yl)-2-oxoethyl]benzamide;
N-(2-aminophenyl)-4-[2-[(4-chlorophenyl)amino]-1-(4-methylpiperazin-1-yl)-2-oxoethyl]benzamide;
N-(2-aminophenyl)-4-[1-(4-methylpiperazin-1-yl)-2-(2-naphthylamino)-2-oxoethyl]benzamide;
N-(2-aminophenyl)-4-{2-[(4-chlorophenyl)amino]-1-[(3S)-3-methylpiperazin-1-yl]-2-oxoethyl}benzamide;
N-(2-aminophenyl)-4-[2-(2-naphthylamino)-2-oxo-1-piperazin-1-ylethyl]benzamide;
N-(2-aminophenyl)-4-[2-(2-naphthylamino)-2-oxo-1-(4-phenylpiperazin-1-yl)ethyl]benzamide;
N-(2-aminophenyl)-4-{2-(2-naphthylamino)-2-oxo-1-[4-(2-phenylethyl)piperazin-1-yl]ethyl}benzamide;
N-(2-aminophenyl)-4-[1-morpholin-4-yl-2-(2-naphthylamino)-2-oxoethyl]benzamide;
N-(2-aminophenyl)-6-{2-[(4-chlorophenyl)amino]-2-oxo-1-[(3-phenylpropanoyl)-amino]ethyl}nicotinamide;
N-(2-aminophenyl)-6-[1-(4-methylpiperazin-1-yl)-2-(2-naphthylamino)-2-oxoethyl]nicotinamide;
N-(4-aminobiphenyl-3-yl)-4-[2-[(4-chlorophenyl)amino]-1-(4-methylpiperazin-1-yl)-2-oxoethyl]benzamide;
N-(4-aminobiphenyl-3-yl)-4-[2-[(4-chlorophenyl)amino]-1-(4-methylpiperazin-1-yl)-2-oxoethyl]benzamide;
N-(4-aminobiphenyl-3-yl)-6-[1-(4-methylpiperazin-1-yl)-2-(2-naphthylamino)-2-oxoethyl]nicotinamide;
N-(4-aminobiphenyl-3-yl)-6-[2-(benzylamino)-1-(4-methylpiperazin-1-yl)-2-oxoethyl]nicotinamide;
N-(4-aminobiphenyl-3-yl)-6-[2-[(4-methylphenyl)amino]-1-(4-methylpiperazin-1-yl)-2-oxoethyl]nicotinamide;
N-(4-aminobiphenyl-3-yl)-6-[2-[(4-chlorophenyl)amino]-1-(4-methylpiperazin-1-yl)-2-oxoethyl]nicotinamide;
N-(2-aminophenyl)-4-[3-[(4-chlorophenyl)amino]-2-(4-methylpiperazin-1-yl)-3-oxopropyl]benzamide;
N-(2-aminophenyl)-4-[2-(4-methylpiperazin-1-yl)-3-(2-naphthylamino)-3-oxopropyl]benzamide;
N-(4-aminobiphenyl-3-yl)-4-[3-[(4-chlorophenyl)amino]-2-(4-methylpiperazin-1-yl)-3-oxopropyl]benzamide;
N-(4-aminobiphenyl-3-yl)-4-[3-(benzylamino)-2-(4-methylpiperazin-1-yl)-3-oxopropyl]benzamide;
N-(4-aminobiphenyl-3-yl)-4-[3-[(4-methoxyphenyl)amino]-2-(4-methylpiperazin-1-yl)-3-oxopropyl]benzamide;
N-(4-aminobiphenyl-3-yl)-4-[3-[(4-methylphenyl)amino]-2-(4-methylpiperazin-1-yl)-3-oxopropyl]benzamide;
N-(4-aminobiphenyl-3-yl)-4-[2-(4-methylpiperazin-1-yl)-3-(2-naphthylamino)-3-oxopropyl]benzamide;
4-{[(2-Aminophenyl)amino]carbonyl}-Nα-benzoyl-N-(4-chlorophenyl)phenyl-alaninamide;
N-(4-aminobiphenyl-3-yl)-4-[4-[(4-chlorophenyl)amino]-3-(4-methylpiperazin-1-yl)-4-oxobutyl]benzamide;
N-(4-aminobiphenyl-3-yl)-4-[4-(benzylamino)-3-(4-methylpiperazin-1-yl)-4-oxobutyl]benzamide;
N-(4-aminobiphenyl-3-yl)-4-[3-(4-methylpiperazin-1-yl)-4-(2-naphthylamino)-4-oxobutyl]benzamide;
N-(4-aminobiphenyl-3-yl)-4-[4-[(4-methylphenyl)amino]-3-(4-methylpiperazin-1-yl)-4-oxobutyl]benzamide;
N-(4-aminobiphenyl-3-yl)-4-[4-[(4-methoxyphenyl)amino]-3-(4-methylpiperazin-1-yl)-4-oxobutyl]benzamide;
Benzyl [(1S)-1-[4-({[2-amino-5-(2-thienyl)phenyl]amino}carbonyl)benzyl]-2-(ethylamino)-2-oxoethyl}carbamate;
Benzyl [(1S)-1-[4-({[2-amino-5-(3-thienyl)phenyl]amino}carbonyl)benzyl]-2-(ethylamino)-2-oxoethyl}carbamate;
Benzyl [(1S)-1-[4-({[2-amino-5-(2-thienyl)phenyl]amino}carbonyl)benzyl]-2-(methylamino)-2-oxoethyl] carbamate;
Benzyl [(1S)-1-[4-({[2-amino-5-(3-thienyl)phenyl]amino}carbonyl)benzyl]-2-(methylamino)-2-oxoethyl] carbamate;
Benzyl [(1S)-1-[4-({[2-amino-5-(2-thienyl)phenyl]amino} carbonyl)benzyl]-2-(4-methylpiperazin-1-1yl)-2-oxoethyl]carbamate;
Benzyl [(1S)-1-[4-({[2-amino-5-(2-thienyl)phenyl]amino} carbonyl)benzyl]-2-morpholin-4-yl-2-oxoethyl]carbamate;
Benzyl [(1S)-1-[4-({[2-amino-5-(2-thienyl)phenyl]amino} carbonyl)benzyl]-2-{[2-(dimethylamino)ethyl]amino}-2-oxoethyl]carbamate;
Benzyl [(1S)-1-[4-({[2-amino-5-(2-thienyl)phenyl]amino} carbonyl)benzyl]-2-(benzylamino)-2-oxoethyl] carbamate;
Benzyl {(1S)-2-amino-1-[4-({[2-amino-5-(2-thienyl)phenyl]amino}carbonyl)benzyl]-2-oxoethyl}carbamate;
(2S)-3-[4-({[2-amino-5-(2-thienyl)phenyl]amino}carbonyl)phenyl]-2-{[(benzyloxy)carbonyl]amino}propanoic acid;

Benzyl [(1S)-1-[4-({[2-amino-5-(2-thienyl)phenyl]amino}carbonyl)benzyl]-2-(dimethylamino)-2-oxoethyl]carbamate;
Benzyl [(1S)-1-[4-({[2-amino-5-(2-thienyl)phenyl]amino}carbonyl)benzyl]-2-(isopropylamino)-2-oxoethyl]carbamate;
Benzyl [(1S)-1-[4-({[2-amino-5-(3-thienyl)phenyl]amino}carbonyl)benzyl]-2-oxo-2-(propylamino)ethyl]carbamate;
Benzyl [(1S)-1-[4-({[2-amino-5-(3-thienyl)phenyl]amino}carbonyl)benzyl]-2-(cyclopropylamino)-2-oxoethyl]carbamate;
Benzyl {(1S)-1-[4-({[2-amino-5-(2-thienyl)phenyl]amino}carbonyl)benzyl]-2-[(2-methoxylethyl)amino]-2-oxoethyl}carbamate;
Benzyl ((1S)-1-[4-({[2-amino-5-(2-thienyl)phenyl]amino}carbonyl)benzyl]-2-{[2-(dimethylamino)-2-oxoethyl]amino}-2-oxoethyl)carbamate;
Benzyl {(1S)-1-[4-({[2-amino-5-(2-thienyl)phenyl]amino}carbonyl)benzyl]-2-[[2-(dimethylamino)-2-oxoethyl](methyl)amino]-2-oxoethyl}carbamate;
Benzyl {(1S)-2-{[2-(acetylamino)ethyl]amino}-1-[4-({[2-amino-5-(2-thienyl)phenyl]amino}carbonyl)benzyl]-2-oxoethyl}carbamate;
Benzyl {(1S)-2-({2-[acetyl(methyl)amino]ethyl}amino)-1-[4-({[2-amino-5-(2-thienyl)phenyl]amino}carbonyl)benzyl]-2-oxoethyl}carbamate;
Benzyl [1(S)-(4-{[4-amino-1-phenyl-1H-pyrazol-3-yl)amino] carbonyl}benzyl)-2-(methylamino)-2-oxoethyl]carbamate;
4-[(2S)-2-(acetylamino)-3-(methylamino)-3-oxopropyl]-N-2-amino-5-(2-thienyl)phenyl]benzamide;
4-[(2S)-2-(acetylamino)-3-(4-methylpiperzin-1-yl)-3-oxopropyl]-N-2-amino-5-(2-thienyl)phenyl]benzamide;
4-[(2S)-2-(acetylamino)-3-morpholin-4-yl-3-oxopropyl]-N-2-amino-5-(2-thienyl)phenyl]benzamide;
4-[(2S)-2-(acetylamino)-3-{[2-(dimethylamino)ethyl]amino}-3-oxopropyl]-N-2-amino-5-(2-thienyl)phenyl]benzamide;
4-[(2S)-2-(acetylamino)-3-(ethylamino)-3-oxopropyl]-N-[2-amino-5-(2-thienyl)phenyl]benzamide;
4-[(2S)-2-(acetylamino)-3-(benzylamino)-3-oxopropyl]-N-[2-amino-5-(2-thienyl)phenyl]benzamide;
N-[2-amino-5-(2-thienyl)phenyl]-4-{(2S)-2-[(methylsulfonyl)amino]-3-morpholin-4-yl-3-oxopropyl}benzamide;
N-[2-amino-5-(2-thienyl)phenyl]-4-{(2S)-3-(ethylamino)-2-[(methylsulfonyl)amino]-3-oxopropyl}benzamide;
N-[2-amino-5-(2-thienyl)phenyl]-4-{(2S)-3-(benzylamino)-2-[(methylsulfonyl)amino]-3-oxopropyl}benzamide;
pyridin-3-ylmethyl[(1S)-1-[4-({[2-amino-5-(2-thienyl)phenyl]amino}carbonyl)benzyl]-2-(ethylamino)-2-oxoethyl]carbamate;
pyridin-3-ylmethyl[(1S)-1-[4-({[2-amino-5-(2-thienyl)phenyl]amino}carbonyl)benzyl]-2-(methylamino)-2-oxoethyl]carbamate;
N-[(1S)-1-[4-({[2-amino-5-(3-thienyl)phenyl]amino}carbonyl)benzyl]-2-oxo-2-(propylamino)ethyl]thiophene-2-carboxamide;
4-[(2S)-2-amino-3-(ethylamino)-3-oxopropyl]-N-[2-amino-5-(2-thienyl)phenyl]benzamide;
4-[(2S)-2-amino-3-(methylamino)-3-oxopropyl]-N-[2-amino-5-(2-thienyl)phenyl]benzamide;
4-((2S)-2-amino-3-{[2-(dimethylaminoethyl]amino}-3-oxopropyl)-N-[2-amino-5-(2-thienyl)phenyl]benzamide;
4-{(2S)-2-amino-3-[(2-methoxyethyl)amino]-3-oxopropyl}-N-[2-amino-5-(2-thienyl)phenyl]benzamide;
2-amino-3-[4-({[2-amino-5-(3-thienyl)phenyl]amino}carbonyl)phenyl]propanoic acid;
Ethyl 3-[4-({[2-amino-5-(2-thienyl)phenyl]amino}carbonyl)phenyl]-2-(dimethylamino)propanoate;
4-[1-(acetylamino)-2-amino-2-oxoethyl]-N-[2-(acetylamino)-5-(2-thienyl)phenyl]benzamide;
N-[2-amino-5-(2-thienyl)phenyl]-4-{2-(methylamino)-1-[(methylsulfonyl)amino]-2-oxoethyl}benzamide;
N-[2-amino-5-(2-thienyl)phenyl]-4-(2-(methylamino)-1-{[(methylamino)carbonyl]amino}-2-oxoethyl)benzamide;
4-{1-[(Acetylamino)methyl]-2-anilino-2-oxoethyl}-N-[2-amino-5-(3-thienyl)phenyl]benzamide;
N-[2-Amino-5-(3-thienyl)phenyl]-4-[2-anilino-1-({[(methylamino)carbonyl]amino} methyl)-2-oxo-ethyl]benzamide;
N-[2-Amino-5-(3-thienyl)phenyl]-4-{2-anilino-1-[(dimethylamino)methyl]-2-oxoethyl}benzamide;
4-{1-[(acetylamino)methyl]-2-anilino-2-oxoethyl}-N-[2-amino-5-(3-thienyl)phenyl]benzamide;
4-[1-[(acetylamino)methyl]-2-(methylamino)-2-oxoethyl]-N-[2-amino-5-(3-thienyl)phenyl]benzamide;
4-[1-[(acetylamino)methyl]-2-(dimethylamino)-2-oxoethyl]-N-[2-amino-5-(3-thienyl)phenyl]benzamide;
4-{1-[(acetylamino)methyl]-2-morpholin-4-yl-2-oxoethyl}-N-[2-amino-5-(3-thienyl)phenyl]benzamide;
N-[2-amino-5-(3-thienyl)phenyl]-4-{2-anilino-1-[(dimethylamino)methyl]-2-oxoethyl}benzamide;
N-[2-amino-5-(3-thienyl)phenyl]-4-[1-[(dimethylamino)methyl]-2-(methylamino)-2-oxoethyl]benzamide;
N-[2-amino-5-(3-thienyl)phenyl]-4-(2-anilino-1-{[(methylsulfonyl)amino]methyl}-2-oxoethyl)benzamide;
N-[2-amino-5-(3-thienyl)phenyl]-4-(2-(methylamino)-1-{[(methylsulfonyl)amino]methyl}-2-oxoethyl)benzamide;
N-[2-amino-5-(3-thienyl)phenyl]-4-(2-(dimethylamino)-1-{[(methylsulfonyl)amino]methyl}-2-oxoethyl)benzamide;
N-[2-amino-5-(3-thienyl)phenyl]-4-[2-anilino-1-({[(methylamino)carbonyl]amino}methyl)-2-oxoethyl]benzamide;
N-[2-amino-5-(3-thienyl)phenyl]-4-[2-(methylamino)-1-({[(methylamino)carbonyl]amino}methyl)-2-oxoethyl]benzamide;
N-[2-amino-5-(3-thienyl)phenyl]-4-[2-(dimethylamino)-1-({[(methylamino)carbonyl]amino}methyl)-2-oxoethyl]benzamide; and
[4-({[2-[(tert-butoxycarbonyl)amino]-5-(2-thienyl)phenyl]amino}carbonyl)phenyl] (pyrrolidin-1-yl)acetic acid;
or a stereoisomer or a pharmaceutically acceptable salt thereof.

6. A pharmaceutical composition comprising a pharmaceutically effective amount of the compound according to claim 1, and a pharmaceutically acceptable carrier.

7. A method of treating neoplastic cancer or tumor in a mammal comprising the step of administering a therapeutically effective amount of the compound of claim 1 in the mammal.

* * * * *